(12) United States Patent
Tour et al.

(10) Patent No.: US 9,572,834 B2
(45) Date of Patent: Feb. 21, 2017

(54) USE OF CARBON NANOMATERIALS WITH ANTIOXIDANT PROPERTIES TO TREAT OXIDATIVE STRESS

(75) Inventors: James M. Tour, Bellaire, TX (US);
Jacob Berlin, Monrovia, CA (US);
Daniela Marcano, Houston, TX (US);
Ashley Leonard, Houston, TX (US);
Thomas A. Kent, Houston, TX (US);
Robia G. Pautler, Pearland, TX (US);
Brittany Bitner, Dallas Center, IA (US); Taeko Inoue, Pasadena, TX (US)

(73) Assignees: WILLIAM MARSH RICE UNIVERSITY, Houston, TX (US);
BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 14/114,007

(22) PCT Filed: Apr. 26, 2012

(86) PCT No.: PCT/US2012/035244
§ 371 (c)(1),
(2), (4) Date: Jan. 13, 2014

(87) PCT Pub. No.: WO2013/066398
PCT Pub. Date: May 10, 2013

(65) Prior Publication Data
US 2014/0120081 A1    May 1, 2014

Related U.S. Application Data

(60) Provisional application No. 61/479,293, filed on Apr. 26, 2011.

(51) Int. Cl.
| | | |
|---|---|---|
| *A61K 31/335* | (2006.01) | |
| *A61K 9/00* | (2006.01) | |
| *A61K 38/00* | (2006.01) | |
| *A61K 47/00* | (2006.01) | |
| *A61K 33/44* | (2006.01) | |
| *B82Y 5/00* | (2011.01) | |
| *A61K 45/06* | (2006.01) | |
| *A61K 47/48* | (2006.01) | |
| *A61K 31/713* | (2006.01) | |

(52) U.S. Cl.
CPC ........... *A61K 33/44* (2013.01); *A61K 9/0019* (2013.01); *A61K 31/713* (2013.01); *A61K 45/06* (2013.01); *A61K 47/48215* (2013.01); *A61K 47/48869* (2013.01); *B82Y 5/00* (2013.01)

(58) Field of Classification Search
CPC .. A61K 2300/00; A61K 33/44; A61K 31/713; A61K 45/06; A61K 47/48215; A61K 47/48953; A61K 9/0019; A61K 9/14; B82Y 5/00

USPC .... 424/130.1; 514/1.1, 44 A, 44 R, 454, 563
See application file for complete search history.

(56) References Cited

U.S. PATENT DOCUMENTS

| | | | | |
|---|---|---|---|---|
| 7,163,956 | B2 * | 1/2007 | Wilson ..................... | A61K 8/19 514/410 |
| 2003/0124122 | A1 * | 7/2003 | Berenson et al. ......... | 424/144.1 |
| 2004/0076681 | A1 | 4/2004 | Dennis et al. | |
| 2006/0275281 | A1 * | 12/2006 | Sullivan ....................... | 424/125 |

(Continued)

FOREIGN PATENT DOCUMENTS

WO   WO9853852 A1 * 12/1998
WO   WO2008118960 A2 * 10/2008

(Continued)

OTHER PUBLICATIONS

Berlin, JM et al. Effective Drug Delivery, in Vitro and in Vivo, by Carbon-Based Nanovectors Noncovalently Loaded with Unmodified Paclitaxel. ACS nano: American Chemical Society. 2010, vol. 4, No. 9; DOI: 10.1021/nn1019994.*

(Continued)

*Primary Examiner* — Janet Epps-Smith
(74) *Attorney, Agent, or Firm* — Winstead PC

(57) ABSTRACT

In some embodiments, the present invention provides methods of treating oxidative stress in a subject by administering a therapeutic composition to the subject. In some embodiments, the therapeutic composition comprises a carbon nanomaterial with anti-oxidant activity. In some embodiments, the anti-oxidant activity of the carbon nanomaterial corresponds to ORAC values between about 200 to about 15,000. In some embodiments, the administered carbon nanomaterials include at least one of single-walled nanotubes, double-walled nanotubes, triple-walled nanotubes, multi-walled nanotubes, ultra-short nanotubes, graphene, graphene nanoribbons, graphite, graphite oxide nanoribbons, carbon black, oxidized carbon black, hydrophilic carbon clusters, and combinations thereof. In some embodiments, the carbon nanomaterial is an ultra-short single-walled nanotube that is functionalized with a plurality of solubilizing groups. In some embodiments, the carbon nanomaterial is a polyethylene glycol functionalized hydrophilic carbon cluster (PEG-HCC). In some embodiments, the administered therapeutic compositions of the present invention may also include an active agent or targeting agent associated with the carbon nanomaterial. Additional embodiments of the present invention pertain to the aforementioned carbon nanomaterial compositions for treating oxidative stress.

28 Claims, 38 Drawing Sheets

(56) References Cited

U.S. PATENT DOCUMENTS

| | | | |
|---|---|---|---|
| 2007/0060636 A1* | 3/2007 | Aviv et al. | 514/453 |
| 2009/0170768 A1 | 7/2009 | Tour et al. | |
| 2009/0215953 A1 | 8/2009 | Hwang et al. | |
| 2010/0144868 A1 | 6/2010 | Gozin et al. | |
| 2010/0197783 A1 | 8/2010 | Tour et al. | |

FOREIGN PATENT DOCUMENTS

| | | |
|---|---|---|
| WO | WO-2009/070380 A2 | 6/2009 |
| WO | WO-2011/087548 A2 | 7/2011 |

OTHER PUBLICATIONS

Bhat, NR. Linking Cardiometabolic Disorders to Sporadic Alzheimer's Disease: a Perspective on Potential Mechanisms and Mediators. Journal of Nuerochemistry. 2010, vol. 115, pp. 551-562; DOI: 10.1111/j.1471-4159.2010.06978.x; p. 552, col. 1, paragraph 1; p. 553, co umn 2, paragraph 2; figure 2.*

Gharbi et al. Nano Lett., vol. 5, No. 12, 2005, 2578-2585.*

Chen et al. American journal of physiology. Regulatory, integrative and comparative physiology (2004), 287(1), R21-6.*

Taylor (2004) Am J Physiol Regul Integr Comp Physiol 287: R1-R2.*

Kaser S, et al. "Pharmacological and non-pharmacological treatment of non-alcoholic fatty liver disease." Int. J. Clin. Pract Jun. 2010;64(7):968-983.

Dumont M, et al. "Mitochondria and antioxidant targeted therapeutic strategies for Alzheimer's disease." J. Alzheimers Dis 2010;20 Suppl 2:S633-643.

Shi X et al., "In vitro cytotoxicity of single-walled carbon nanotube/biodegradable polymer nanocomposites." J Biomed Mater Res A Sep. 2008;86(3):813-823.

Drezek RA et al., "Is nanotechnology too broad to practise?" Nat Nanotechnol Mar. 2010;5(3):168-169.

Liu Z et al., "Circulation and long-term fate of functionalized, biocompatible single-walled carbon nanotubes in mice probed by Raman spectroscopy." Proc. Natl. Acad. Sci. U.S.A Feb. 2008;105(5):1410-1415.

Schipper ML et al., "A pilot toxicology study of single-walled carbon nanotubes in a small sample of mice." Nat Nanotechnol Apr. 2008;3(4):216-221.

Mutlu GM et al., "Biocompatible nanoscale dispersion of single-walled carbon nanotubes minimizes in vivo pulmonary toxicity." Nano Lett May 2010;10(5):1664-1670.

Kolosnjaj-Tabi J et al., "In vivo behavior of large doses of ultrashort and full-length single-walled carbon nanotubes after oral and intraperitoneal administration to Swiss mice." ACS Nano Mar. 2010;4(3):1481-1492.

Kagan VE et al., "Carbon nanotubes degraded by neutrophil myeloperoxidase induce less pulmonary inflammation." Nat Nanotechnol May 2010;5(5):354-359.

Hurt RH et al., "Toxicology of carbon nanomaterials: Status, trends, and perspectives on the special issue." Carbon May 2006;44(6):1028-1033.

Rigg et al., "A review of the effectiveness of antioxidant therapy to reduce neuronal damage in acute traumatic brain injury." J. Head Trauma Rehabil. 20:389-391; 2005.

Marshall et al. "A multicenter trial on the efficacy of using tirilazad mesylate in cases of head injury." J. Neurosurg. 89:519-525; 1998.

Muizelaar et al., "Improving the outcome of severe head injury with the oxygen radical scavenger polyethylene glycol-conjugated superoxide dismutase: a phase II trial." J. Neurosurg. 78:375-382; 1993.

Berlin et al. "Noncovalent functionalization of carbon nanovectors with an antibody enables targeted drug delivery." ACS Nano 5, 6643-6650 (2011).

Hall et al. "Antioxidant therapies for traumatic brain injury." Neurotherapeutics. 7:51-61; 2010.

Ali et al., "SOD activity of carboxyfullerenes predicts their neuroprotective efficacy: a structure-activity study." Nanomedicine. 4:283-294; 2008.

Dugan et al., "Carboxyfullerenes as neuroprotective agents." Proc. Natl. Acad. Sci. USA. 94:9434-9439; 1997.

Ali et al., "A biologically effective fullerene (C60) derivative with superoxide dismutase mimetic properties." Free Radic. Biol. Med. 37:1191-1202; 2004.

Quick, K. L. et al., "A carboxyfullerene SOD mimetic improves cognition and extends the lifespan of mice." Neurobiol. Aging. 29:117-128; 2008.

Dugan et al., "Fullerene-based antioxidants and neurodegenerative disorders." Parkinsonism Relat. Disord. 7:243-246; 2001.

Hirst et al., "Anti-inflammatory properties of cerium oxide nanoparticles." Small. 5:2848-2856; 2009.

Galano et al., "Carbon nanotubes: promising agents against free radicals", 2010, Nanoscale, 2, 373-380.

Das et al., "Auto-catalytic ceria nanoparticles offer neuroprotection to adult rat spinal cord neurons." Biomaterials. 28:1918-1925; 2007.

Tarnuzzer et al."Vacancy engineered ceria nanostructures for protection from radiation-induced cellular damage." Nano Lett. 5:2573-2577; 2005.

Martin et al. "Nano-Jewels in Biology. Gold and Platinum on Diamond Nanoparticles as Antioxidant Systems Against Cellular Oxidative Stress." ACS Nano. 4:6957-6965;2010.

Wu et al., "Chemistry of carbon nanotubes in biomedical applications." J. Mater. Chem. 20:1036-1052; 2010.

Kostarelos et al., "Promises, facts and challenges for carbon nanotubes in imaging and therapeutics." Nat. Nanotechnol. 4:627-633; 2009.

Riehemann et al. "Nanomedicine—challenge and perspectives." Angew. Chem. Int. Ed. Engl. 48:872-897; 2009.

Stephenson et al., "Repetitive Functionalization of Water-Soluble Single-Walled Carbon Nanotubes. Addition of Acid-Sensitive Addends." Chem. Mat. 19:3491-3498; 2007.

Chang et al., "Therapy of NAFLD: antioxidants and cytoprotective agents." J. Clin. Gastroenterol. 40 Suppl 1, S51-60 (2006).

Tasis et al., "Chemistry of Carbon Nanotubes", Chem. Rev. 106, 1105-1136 (2006).

Nahar et al., "Functional polymeric nanoparticles: an efficient and promising tool for active delivery of bioactives", Crit Rev Ther Drug Carrier Syst, 2006, 23(4):259-318.

Khopde et al., "Free radical scavenging ability and antioxidant efficiency of curcumin and its substituted analogue", Biophys Chem, 1999, 80(2), 85-91.

Zlokovic BV, "New therapeutic targets in the neurovascular pathway in Alzheimer's Disease" Neurotherapeutics. Jul. 2008;5(3):409-14 (review).

Constantino, L et al., "Nanoparticulate drug carriers based on hybrid poly(d,l-lactide-co-glycolide)-dendron structures", Biomaterials, 2006, 27, 4635-4645.

Klumpp et al., "Functionalized Carbon Nanotubes as Emerging Nanovectors for the Delivery of Therapeutics." Biochim. Biophys. Acta. 2006;1758:404-412.

Koob et al., 2005, "Intravenous Polyethylene Glycol Inhibits the Loss of Cerebral Cells after Brain Injury." J. Neurotrauma, 22, 1092-1111.

Liu-Snyder et al., 2007, "Neuroprotection from secondary injury by polyethylene glycol requires its internalization", J Exp Biol., 210, 1455-1462.

Malhotra et al., 2011, "High-molecular-weight polyethylene glycol protects cardiac myocytes from hypoxia and reoxygenation-induced cell death and preserves ventricular function." Am. J. Physiol. Hearth Circ. Physiol., 300, H1733-H1742.

Bar-Shir et al., 2005., "Synthesis and Water Solubility of Adamantyl-OEG-fullerene Hybrids." J. Org. Chem., 70, 2660-266.

Giacino et al., "Placebo-controlled trial of amantadine for severe traumatic brain injury." N Engl J Med., 3669, 819-26.

Williams et al., 2007, "Amantadine treatment following traumatic brain injury in children", Brain Inj., 9, 885-889.

(56) References Cited

OTHER PUBLICATIONS

Dugan, L.L. et al., "Buckminsterfullerenol free radical scavengers reduce excitotoxic and apoptotic death of cultured cortical neurons." Neurobiol. Dis. 3, 129-135.
Ou et al., Novel Fluorometric Assay for Hydroxyl Radical Prevention Capacity Using Fluorescein as the Probe, J. Agric. Food Chem., 2002, 50, 2772-2777.
Lucente-Schultz et al., "Antioxidant single-walled carbon nanotubes." J. Am. Chem. Soc Mar. 2009;131(11):3934-3941.
Chen et al., "Soluble ultra-short single-walled carbon nanotubes." *J. Am. Chem. Soc.* 128:10568-10571; 2006.
Price et al. "Aggressively Oxidized Ultra-Short Single-Walled Carbon Nanotubes Having Oxidized Sidewalls." *Chem. Mat.* 21:3917-3923; 2009.
Wörle-Knirsch et al., "They Did It Again! Carbon Nanotubes Hoax Scientists in Viability Assays." *Nano Lett.* 6:1261-1268; 2006.
International Search Report and Written Opinion for PCT/US2012/035244, Mailed on Apr. 10, 2013.
International Preliminary Report on patentability for PCT/US2012/035244, Mailed on Nov. 7, 2013.
Amantadine—Wikipedia, the free encyclopedia, https://en.wikipedia.org/wiki/Amantadine, Sep. 16, 2016.
Crosby, NJ et al., Amantadine in Parkinson's Disease (Review), Cochrane Database of Systematic Reviews, 2003, Issue 1, Art. No. CD003648, www.cochranelibrary.com.

\* cited by examiner

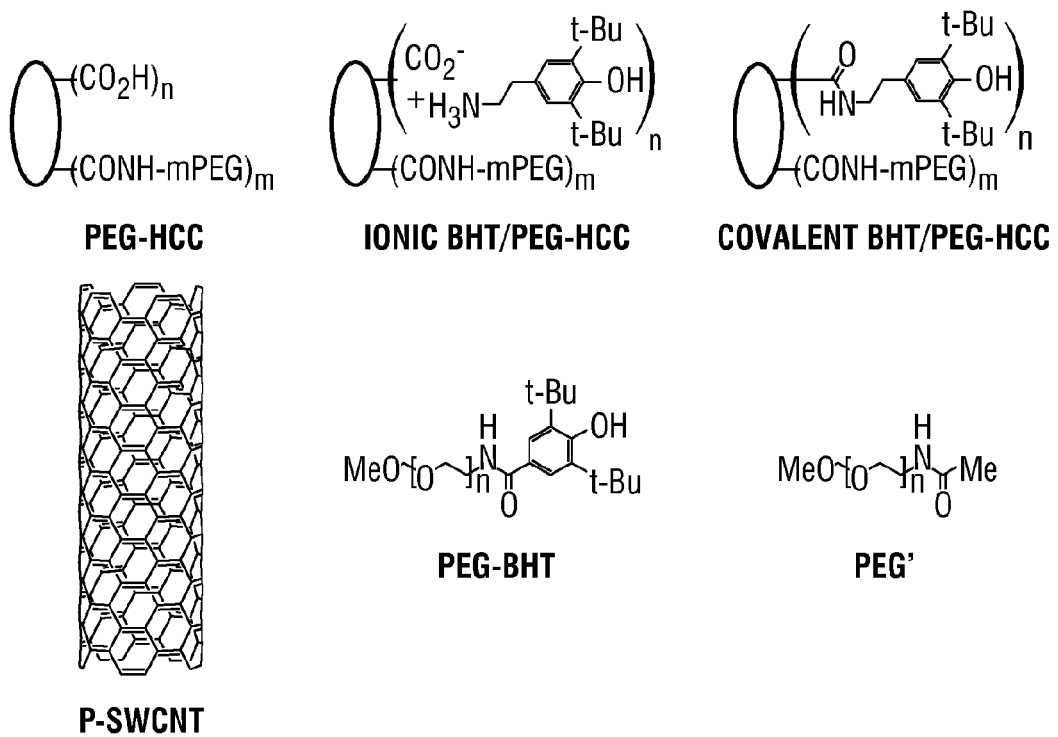
*FIG. 1A*
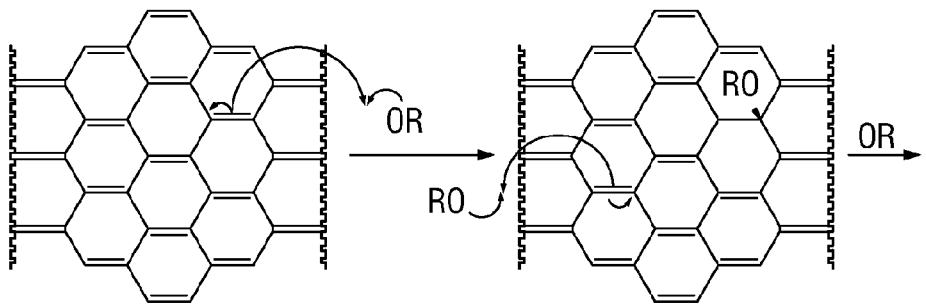
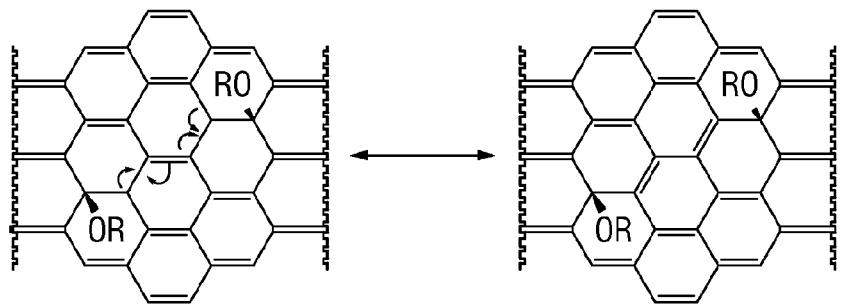
*FIG. 1B*

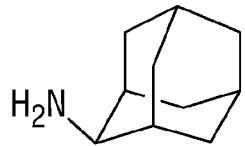
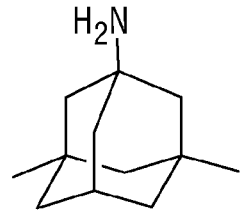
ADAMANTANE  AMANTADINE  MEMANTINE
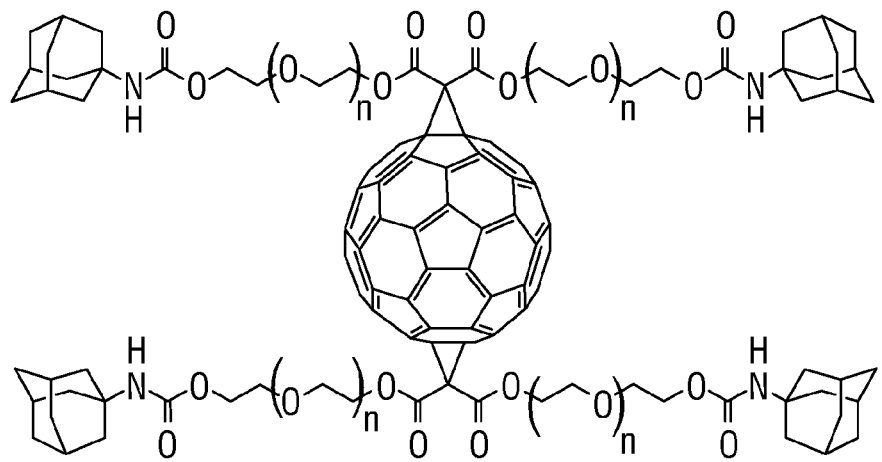
ABS-75
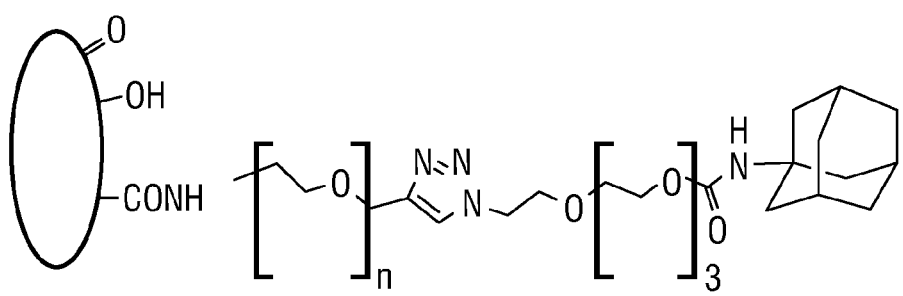
ADA-PEG-HCCs
*FIG. 1E*

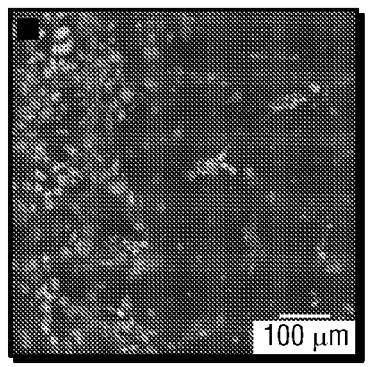 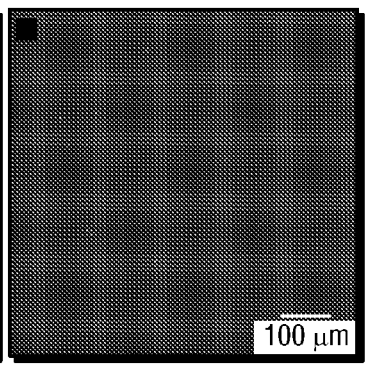 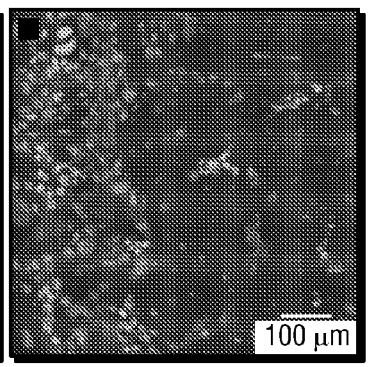
FIG. 10A  FIG. 10B  FIG. 10C
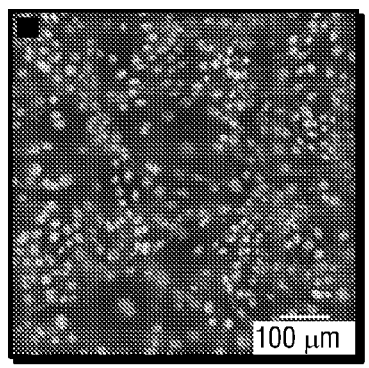 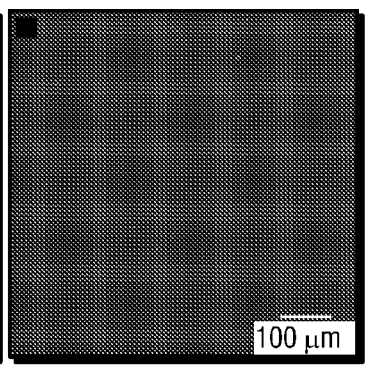 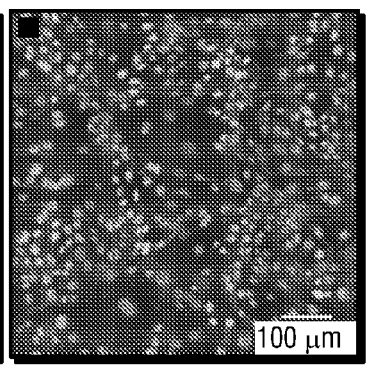
FIG. 10D  FIG. 10E  FIG. 10F
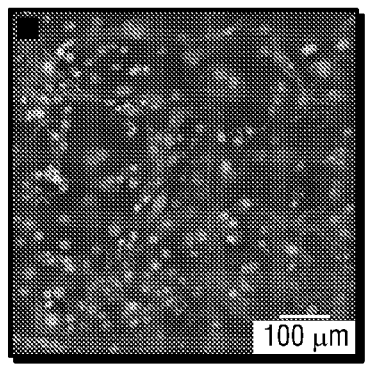 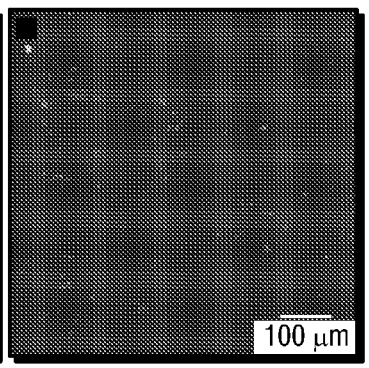 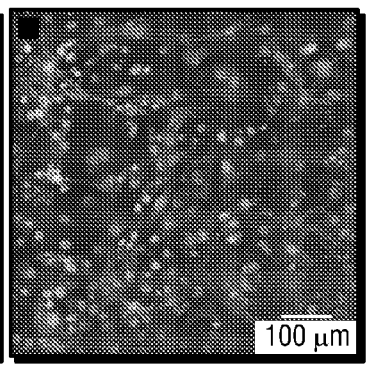
FIG. 10G  FIG. 10H  FIG. 10I

| COMPOUND | IC$_{50}$ FOR CYTOCHROME c OXIDATION [mg/L OF CARBON CORE] ($\pm$SD) |
|---|---|
| pl/SWNT | 0.61 $\pm$ 0.11 |
| PEG-HCCs | 200 $\pm$ 11 |
| PLURONIC | NO EFFECT |
| PEG (CONTROL) | NO EFFECT |

| TREATMENT | TIME | CELL SURVIVAL RELATIVE TO CONTROL [%] | p-VALUE[b] |
|---|---|---|---|
| PEG-HCCs[25 mg/L] | 6 H | 103 | 0.62 |
| PEG-HCCs[50 mg/L] | 6 H | 103 | 0.67 |
| PEG-HCCs[100 mg/L] | 6 H | 106 | 0.29 |
| PEG-HCCs[200 mg/L] | 6 H | 99 | 0.84 |
| PEG-HCCs[25 mg/L] | 24 H | 101 | 0.42 |
| PEG-HCCs[50 mg/L] | 24 H | 93 | 0.69 |
| PEG-HCCs[100 mg/L] | 24 H | 90 | 0.87 |
| PEG-HCCs[200 mg/L] | 24 H | 92 | 0.93 |
| PLURONIC ONLY | 6 H | 93 | 0.34 |
| pl/SWNTs [4 mg/L] | 6 H | 92 | 0.25 |
| pl/SWNTs [8 mg/L] | 6 H | 92 | 0.33 |
| pl/SWNTs [10 mg/L] | 6 H | 88 | 0.14 |
| PLURONIC ONLY | 24 H | 86 | 0.20 |
| pl/SWNTs [4 mg/L] | 24 H | 82 | 0.061 |
| pl/SWNTs [8 mg/L] | 24 H | 67 | 0.0062 |
| pl/SWNTs [10 mg/L] | 24 H | 52 | 0.0012 |

| TREATMENT | CELL SURVIVAL RELATIVE TO CONTROL [%] | p-VALUE[b] |
|---|---|---|
| PEG-HCCs[25 mg/L] | 130 | 0.0045 |
| PEG-HCCs[50 mg/L] | 104 | 0.28 |
| PEG-HCCs[100 mg/L] | 131 | 0.17 |
| PEG-HCCs[200 mg/L] | 141 | 0.0024 |
| PLURONIC ONLY | 9 | 0.0011 |
| pl/SWNTs [4 mg/L] | 4 | 0.00046 |
| pl/SWNTs [8 mg/L] | 0 | 0.00035 |
| pl/SWNTs [10 mg/L] | 0 | 0.00035 |

*FIG. 26C*

| TREATMENTS | ANTIMYCIN A | DHE MEAN FLOURESCENT INTENSITY(% CONTROL) | ±SD | P-VALUE COMPARED TO PBS + ANTIMYCIN A |
|---|---|---|---|---|
| PBS | − | 173 | ±46 | < 0.001 |
| PBS + ANTIMYCIN A | + | 297 | ±71 | − |
| PEG-HCCs [0.1 mg/L] | + | 242 | ±29 | N.S. |
| [1.0 mg/L] | + | 192 | ±57 | <0.01 |
| [2.0 mg/L] | + | 175 | ±46 | <0.001 |
| [4.0 mg/L] | + | 143 | ±51 | <0.001 |
| pl/SWCNTs [0.12 mg/L] | + | 206 | ±63 | <0.05 |
| [0.48 mg/L] | + | 163 | ±55 | <0.001 |
| SOD [4 U/L] | + | 225 | ±19 | N.S. |
| SOD [40 U/L] PRETREAT | + | 209 | ±65 | <0.001 |
| PBN [54 mg/L] | + | 148 | ±59 | N.S. |
| PBN [1100 mg/L] PRETREAT | + | 164 | ±27 | <0.001 |

*FIG. 29*

| TREATMENTS | ANTIMYCIN A | VIABLE CELLS/mL (% CONTROL) | ± SD | P-VALUES | COMPARED TO |
|---|---|---|---|---|---|
| PBS | − | 100 | ± 0 | < 0.05 | SOD, PBS + ANTIMYCIN A |
| PBS + ANTIMYCIN A | + | 75 | ± 10 | <0.05 | PEG-HCCs + ANTIMYCIN A |
| PEG-HCCs | − | 117 | ± 16 | <0.001 | PBS + ANTIMYCIN A |
| PEG-HCCs + ANTIMYCIN A | + | 101 | ± 15 | <0.05 | PBS + ANTIMYCIN A |
| pl/SWCNTs | − | 101 | ± 14 | <0.05 | PBS + ANTIMYCIN A |
| pl/SWCNTs + ANTIMYCIN A | + | 85 | ± 21 | N.S. | |
| SOD | − | 127 | ± 18 | <0.001 | PBS + ANTIMYCIN A, SOD + ANTIMYCIN A |
| SOD + ANTIMYCIN A | + | 85 | ± 15 | — | |
| PBN | − | 100 | ± 20 | <0.05 | PBS + ANTIMYCIN A |
| PBN + ANTIMYCIN A | + | 85 | ± 20 | N.S. | |

FIG. 31

USE OF CARBON NANOMATERIALS WITH ANTIOXIDANT PROPERTIES TO TREAT OXIDATIVE STRESS

CROSS-REFERENCE TO RELATED APPLICATIONS

This application claims priority to U.S. Provisional Patent Application No. 61/479,293, filed on Apr. 26, 2011. The entirety of the aforementioned application is incorporated herein by reference.

STATEMENT REGARDING FEDERALLY SPONSORED RESEARCH

This invention was made with Government Support under NSF Grant No. EEC-0647452, awarded by the National Science Foundation; Grant No. W81XWH-08-2-0143, awarded by the Department of Defense; Grant No. W8XWH-07-2-0101, awarded by the U.S. Department of Defense; Grant No. W81XWH-08-2-0141, awarded by the U.S. Department of Defense; and Grant No. P30 DK079638-03, awarded by the National Institutes of Health. The Government has certain rights in the invention.

BACKGROUND

Current methods of treating oxidative stress have numerous limitations in terms of efficacy and specificity in targeting desired sites. Therefore, a need exists for the development of more effective and targeted methods of treating oxidative stress.

BRIEF SUMMARY

In some embodiments, the present disclosure provides methods of treating oxidative stress in a subject by administering a therapeutic composition to the subject. In some embodiments, the therapeutic composition comprises a carbon nanomaterial with anti-oxidant activity. In some embodiments, the anti-oxidant activity of the carbon nanomaterial corresponds to oxygen radical absorbance capacity (ORAC) values between about 200 to about 15,000.

In some embodiments, the administered carbon nanomaterials in the therapeutic composition include at least one of single-walled nanotubes, double-walled nanotubes, triple-walled nanotubes, multi-walled nanotubes, ultra-short nanotubes, graphene, graphene nanoribbons, graphite, graphite oxide nanoribbons, carbon black, oxidized carbon black, hydrophilic carbon clusters, and combinations thereof. In some embodiments, the carbon nanomaterial is an ultra-short single-walled nanotube that is functionalized with a plurality of solubilizing groups. In some embodiments, the carbon nanomaterial is a hydrophilic carbon cluster (HCC) or a polyethylene glycol functionalized hydrophilic carbon cluster (PEG-HCC).

In some embodiments, the therapeutic compositions of the present disclosure may also include an active agent associated with the carbon nanomaterial. In some embodiments, the active agent may be covalently or non-covalently associated with the carbon nanomaterial. In some embodiments, the therapeutic compositions of the present disclosure may also include a targeting agent that has recognition activity for a marker related to oxidative stress, such as a cell surface protein that is up-regulated in response to oxidative stress. In some embodiments, the therapeutic compositions of the present disclosure may also be associated with a transporter moiety that facilitates the transport of carbon nanomaterials through a barrier.

In some embodiments, the methods of the present disclosure may treat oxidative stress by reducing the levels of reactive oxygen species in the subject. In some embodiments, the methods of the present disclosure may be used to reduce the levels of reactive oxygen species in the subject by about 5% to about 50%, and particularly at an injured site of interest.

Additional embodiments of the present disclosure pertain to the aforementioned carbon nanomaterial compositions for treating oxidative stress. The methods and compositions of the present disclosure may be used to treat oxidative stress that may be associated with numerous conditions, including, without limitation, traumatic brain injury (TBI), ischemia, anoxic encephalopathy, hypoxic or ischemic encephalopathy, cerebrovascular dysfunction, hemorrhagic shock, hypoxia, hypotension, Alzheimer's disease, Parkinson's disease, multiple sclerosis, amyotrophic lateral sclerosis (ALS or Lou Gehrig's disease), liver disease, non-alcoholic fatty liver disease, diabetes, stroke, inflammation, spinal cord injury (SCI), central nervous system injury (CNSI) or neuropathy, organ transplantation (treatment of the organ or the patient) and combinations thereof. Furthermore, the methods and compositions of the present disclosure may be used to treat oxidative stress with minimal toxicity and side effects.

BRIEF DESCRIPTION OF THE FIGURES

FIG. 1 provides illustrations of carbon nanomaterials and their anti-oxidant activities. FIG. 1A provides structures of various carbon nanomaterials. FIG. 1B provides a potential mechanism by which carbon nanomaterials can scavenge free radicals. FIG. 1E shows the structures of various transporter moieties and their association with various carbon nanomaterials.

FIG. 2 provides representative fluorescence decay and calibration curves.

FIG. 3 provides fluorescence quenching data comparing the anti-oxidative properties of PEG-HCCs to various antioxidants.

FIG. 8 shows fluorescence decay and calibration curves.

FIG. 10 shows images of mock, PEG and PEG-HCC-treated b.End.3 cells. Cell nuclei were stained with DAPI (blue), cell membranes with Wheat Germ Agglutinin 594 (red), and PEG and PEG-HCCs were stained using a primary antibody against PEG with an Alexa-633 conjugated secondary antibody (orange). Each set of images was taken with the same settings on a Zeiss LSM 510 confocal microscope, and are shown at the same brightness/contrast levels. FIG. 10A shows the membrane and nuclei stained cells. FIG. 10B shows the PEG-stained cells. FIG. 10C shows the overlapped images of the mock treated cells. FIG. 10D shows the membrane and nuclei stained cells. FIG. 10E shows PEG-stained cells. FIG. 10F shows overlapped images of the PEG-treated cells. FIG. 10G shows the membrane and nuclei stained cells. FIG. 10H shows PEG-stained cells. FIG. 10I shows overlapped images of the PEG-HCC-treated cells. When PEG-HCC-treated cells were stained with the secondary antibody only (data not shown), no signal was observed indicating that there is no non-specific antibody staining.

FIG. 11 shows high resolution images of b.End.3 cells treated with PEG-HCC and PEG. Cell nuclei were stained with DAPI (blue). Cell membranes were stained with Wheat Germ Agglutinin 594 (red). The treated cells were stained using a primary antibody against PEG with an Alexa-633 conjugated secondary antibody (orange). Each set of images were taken with the same settings on a Zeiss LSM 510 confocal microscope, and are shown at the same brightness/contrast levels.

FIG. 12 shows data indicating that PEG-HCCs protect brain endothelial cells from oxidative stress when administered after an insult.

FIG. 13 shows DAF-2DA intensity in bEnd.3 cells that spontaneously generate nitric oxide (NO) after treatment with increasing concentrations of PEG-HCCs. DAF-2DA is a NO sensitive dye.

FIG. 15 shows histological and behavioral evidence that the combination of traumatic brain injury (TBI) and hypotension worsens oxidative stress.

FIG. 19 shows Laser Doppler flowmetry (LDF) results relating to treatment of rat models of TBI with two doses of PEG-HCCs.

FIG. 25 shows pl/SWNTs and PEG-HCCs quench superoxide.

FIG. 26 shows toxicity studies of SWNTs and PEG-HCCs with b.End3 cells. FIG. 26C shows data relating to the survival of b.end3 cells treated with various concentrations of PEG-HCCs, pl/SWNTs or 1% pluronic, as measured by a clonogenic survival assay.

FIG. 29 is a table of intracellular ROS levels and statistics for b.End3 cells, as determined by DHE staining and flow cytometry. Superoxide production was induced using antimycin A, and superoxide levels were measured with the superoxide-specific dye, DHE. All results were calculated as percent control from non-antimcyin A and non-DHE treated cells (100%). All statistics are compared to the PBS+ Antimcyin A treated group.

FIG. 31 show a table summarizing cell survival numbers relative to control and statistics for b.End3 cells given different treatments. Bold lettering indicates statistics displayed in FIG. 30 (n.s.=not significant).

DETAILED DESCRIPTION

Figure 1C:
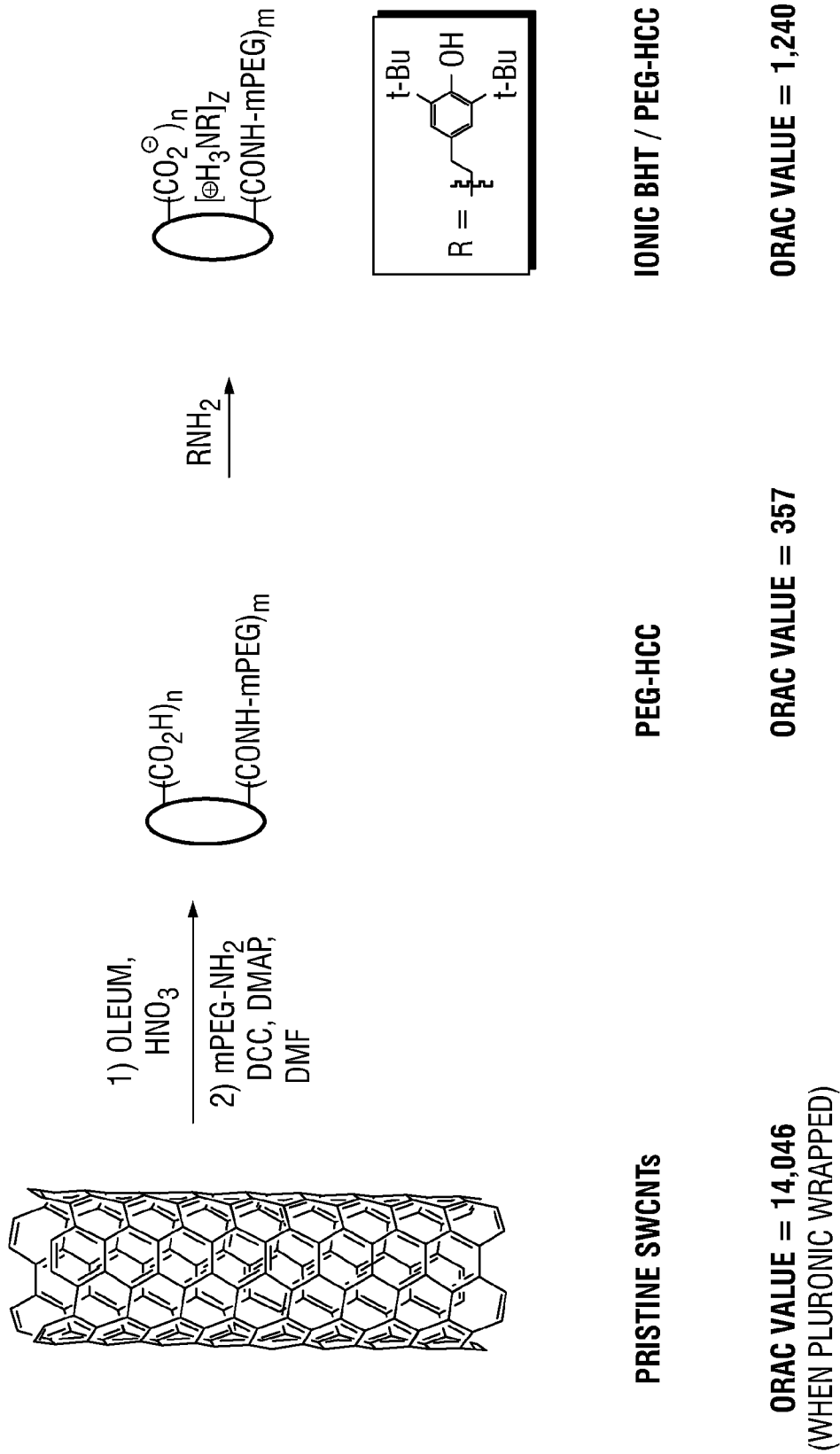
FIG. 1C provides additional structures of carbon nanomaterials, their schematic syntheses, and their corresponding oxygen radical absorbance capacity (ORAC) values.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Damage to the vasculature caused by oxidative stress is a significant contributor to a variety of neurological complications, including ischemia and traumatic brain injury. Elevated levels of reactive oxygen species (ROS), including reactive free radicals derived from them, are a cause of the oxidative stress, as they are capable of damaging lipids, proteins and nucleic acids. Furthermore, ROS-initiated reactions, such as lipid peroxidation, can establish a prolonged propagation of free radical-mediated injuries to various cells, tissues and organs.

Antioxidant therapies have been investigated for treating oxidative stress, including traumatic brain injury. For instance, extensive research has explored using small molecule antioxidants, such as phenyl N-tert-butyl nitrone (PBN), or stabilized enzymes, such as polyethylene functionalized superoxide dismutase (PEG-SOD), to combat oxidative stress. However, these potential therapies have shown limited efficacy in clinical trials. Furthermore, there are limited Food and Drug Administration-approved antioxidant therapies for these conditions. Therefore, a need exists for new methods and therapeutic compositions for treating oxidative stress. The present disclosure addresses this need.

In some embodiments, the present disclosure provides methods of treating oxidative stress in a subject by administering to the subject a therapeutic composition that includes a carbon nanomaterial with anti-oxidant activity. Additional embodiments of the present disclosure pertain to the therapeutic compositions that are administered to the subject. The methods and compositions of the present disclosure may be used to treat oxidative stress that is associated with various conditions, including, without limitation, traumatic brain injury (TBI), ischemia, anoxic encephalopathy, hypoxic or ischemic encephalopathy, cerebrovascular dysfunction, hemorrhagic shock, hypoxia, hypotension, Alzheimer's disease, Parkinson's disease, multiple sclerosis, amyotrophic lateral sclerosis (ALS or Lou Gehrig's disease), liver disease, non-alcoholic fatty liver disease (NAFLD), diabetes, stroke, inflammation, spinal cord injury (SCI), central nervous system injury (CNSI) or neuropathy, organ transplantation (treatment of the organ or the patient) and combinations thereof.

Additional support for the embodiments of the present disclosure can also be found in the following of Applicants' co-pending patent applications: PCT/US2008/078776, entitled "Water Soluble Carbon Nanotube Compositions for Drug Delivery and Medical Applications"; and PCT/

US2010/054321, entitled "Therapeutic Compositions and Methods for Targeted Delivery of Active Agents." Also see U.S. patent application Ser. Nos. 12/245,438 and 12/280,523.

Therapeutic Compositions

Various embodiments of the present disclosure pertain to therapeutic compositions for treating oxidative stress. As set forth in more detail below, such therapeutic compositions can have numerous variations. In some embodiments, the therapeutic compositions of the present disclosure include a carbon nanomaterial with anti-oxidant activity. In some embodiments, the carbon nanomaterials of the present disclosure may also be associated with one or more active agents, such as anti-oxidants. In some embodiments, the carbon nanomaterials of the present disclosure may also be associated with one or more targeting agents, such as targeting agents that have recognition activity for a marker related to oxidative stress.

Carbon Nanomaterials

Carbon nanomaterials suitable for use in the therapeutic compositions of the present disclosure generally refer to particles that have anti-oxidant activity. Structures of suitable and non-limiting carbon nanomaterials are shown in FIG. 1A.

In some embodiments, suitable carbon nanomaterials include, without limitation, single-walled nanotubes (SWNTs), double-walled nanotubes (DWNTs), triple-walled nanotubes (TWNTs), multi-walled nanotubes (MWNTs), ultra-short nanotubes, ultra-short single-walled nanotubes (US-SWNTs), hydrophilic carbon clusters (HCCs), graphene nanoribbons, graphite, graphite oxide nanoribbons, carbon black, derivatives thereof, and combinations thereof.

In some embodiments, the carbon nanomaterials of the present disclosure may be modified in various ways. For instance, in some embodiments, the carbon nanomaterials of the present disclosure may be oxidized. In some embodiments, the carbon nanomaterials of the present disclosure may be functionalized with one or more molecules, polymers, chemical moieties, solubilizing groups, functional groups, and combinations thereof. For instance, in some embodiments, the carbon nanomaterials of the present disclosure may be functionalized with ketones, alcohols, epoxides, carboxylic acids, and combinations thereof.

In more specific embodiments, the carbon nanomaterials of the present disclosure may be functionalized with a plurality of solubilizing groups. In further embodiments, the solubilizing groups may include at least one of polyethylene glycols (PEGs), polypropylene glycol (PPG), poly(p-phenylene oxide) (PPOs), polyethylene imines (PEI), poly(vinyl alcohol) (PVA), poly(acrylic acid) (PAA) and combinations thereof. In some embodiments, the carbon nanomaterials of the present disclosure can include PEG-functionalized HCCs (i.e., PEG-HCCs, as described in more detail below).

In some embodiments, the solubilizing groups or functional groups may be covalently associated with the carbon nanomaterials. In some embodiments, the solubilizing groups or functional groups may be non-covalently associated with the carbon nanomaterials. In more specific embodiments, carbon nanomaterials may include SWNTs that are non-covalently wrapped with a plurality of solubilizing groups, such as PEGs or pluronic (PEG-PPG-PEG). In some embodiments, the carbon nanomaterials may include pluronic wrapped SWNTs (pl/SWNTs).

In some embodiments, the carbon nanomaterials of the present disclosure may also be associated with one or more transporter moieties. Transporter moieties generally refer to molecules or functional groups that facilitate or promote the transport of a carbon nanomaterial to a site of interest. For instance, in some embodiments, the transporter moiety may be a molecule that facilitates the transfer of a carbon nanomaterial through the blood brain barrier (BBB) or the blood spinal cord barrier (BSB). In some embodiments, the transporter moiety may be a BBB or BSB transporter, such as an adamantane molecule or an adamantane derivative, including, without limitation, amantadine, memantine, rimantadine, dopamantin, tromantadine, vildagliptin, karmantadin, and combinations thereof. Exemplary structures of adamantane molecules are shown in FIG. 1E (upper panel).

In some embodiments, the BBB or BSB transporter moiety may include a cannibinoid molecule or a cannibinoid derivative, including, without limitation, cannabigerol, cannabigerol monomethyl ether, cannabinerolic acid A, cannabigerovarin, cannabigerolic acid A, cannabigerolic acid A monomethyl ether, cannabigerovarinic acid A, cannabichromene, cannabichromenic acid A, cannabivarichromene, cannabichromevarin, cannabichromevarinic acid A, cannabidiol, cannabidiol momomethyl ether, cannabidiol-$C_4$, cannabidivarin, cannabidiorcol, cannabidiolic acid, cannabidivarinic acid, cannabinodiol, cannabinodivarin, cannabivarin, cannabicitran, HU-210 and combinations thereof. In some embodiments, the BBB or BSB transporter moiety may be a synthetic cannabinoid derivative that is the "unnatural" enantiomer of a cannabinoid, such as dexanabinol (HU-211), which is a synthetic cannabinoid derivative that is the "unnatural" enantiomer of the potent cannabinoid agonist HU-210.

Transporter moieties may be associated with carbon nanomaterials in various manners. In some embodiments, the transporter moieties may be covalently linked to the ends or sidewalls of carbon nanomaterials. In various embodiments, the covalent linkage may occur directly or through a linker molecule. In some embodiments, the transporter may be associated with the end of the solubilizing chain, as shown in FIG. 1E (e.g., lower panel, showing ADA-PEG-HCC). In some embodiments, one or more transporter moieties may be non-covalently linked to carbon nanomaterials.

In more specific embodiments, the carbon nanomaterials of the present disclosure include US-SWNTs. US-SWNTs are also referred to as hydrophilic carbon clusters (HCCs). Therefore, for the purposes of the present disclosure, US-SWNTs are synonymous with HCCs. In some embodiments, HCCs can include oxidized carbon nanoparticles that are about 30 nm to about 60 nm long, and approximately 1-2 nm wide.

In some embodiments, US-SWNTs (i.e., HCCs) may be produced by reacting SWNTs in fuming sulfuric acid with nitric acid to produce a shortened carbon nanotube characterized by opening of the nanotube ends. Such methods are disclosed in Applicants' co-pending U.S. patent application Ser. No. 12/280,523, entitled "Short Functionalized, Soluble Carbon Nanotubes, Methods of Making Same, and Polymer Composites Made Therefrom." This may be followed by the functionalization of the plurality of carboxylic acid groups. In some embodiments, the HCC may be an oxidized graphene.

In some embodiments, the HCCs may be functionalized with one or more solubilizing groups, such as PEGs, PPOs, PEIs, PVAs, PAAs, and combinations thereof (as previously described). In more specific embodiments, the carbon nanomaterials of the present disclosure may include polyethylene glycol-functionalized HCCs (PEG-HCCs). Various PEG-HCCs and methods of making them are disclosed in the following articles and patent applications: Berlin et al., *ACS Nano* 2010, 4, 4621-4636; Lucente-Schultz et al., *J. Am.*

Chem. Soc. 2009, 131, 3934-3941; Chen et al., *J. Am. Chem. Soc.* 2006, 128, 10568-10571; Stephenson, et al., *Chem. Mater.* 2007, 19, 3491-3498; Price et al., *Chem. Mater.* 2009, 21, 3917-3923; PCT/US2008/078776; and PCT/US2010/054321.

In some embodiments, HCCs and PEG-HCCs may also be associated with one or more transporter moieties (as previously described). For instance, in some embodiments, the ends or sidewalls of HCCs or PEG-HCCs can be covalently linked to an adamantane or cannabinoid molecule to facilitate its transfer through the BBB or BSB. See, e.g., FIG. 1E (lower panel).

In various embodiments, PEG-HCCs (and other functionalized forms of HCCs) may have various advantageous properties for use as carbon nanomaterials. For instance, PEG-HCCs (and other functionalized forms of HCCs) may demonstrate low biological toxicity with clearance mainly through the kidneys. PEG-HCCs (and other functionalized forms of HCCs) may also contain hydrophobic domains that can be non-covalently loaded with active agents, such as hydrophobic active agents. In addition, PEG-HCCs (and other functionalized forms of HCCs) can have an ability to strongly bind to various targeting agents (such as monoclonal or IgG-type antibodies) without significantly interfering with the activity of the targeting agents.

Other suitable PEGylated or functionalized carbon nanomaterials can also be used as carbon nanomaterials. Non-limiting examples include PEGylated graphite oxide nanoribbons (PEG-GONR), PEGylated oxidized carbon black (PEG-OCB), and PEGylated carbon black (PEG-CB). Additional suitable carbon nanomaterials, including PEG-HCCs, are disclosed in U.S. patent application Ser. No. 12/245,438; PCT/US2008/078776; and PCT/US2010/054321. The use of other suitable carbon nanomaterials not disclosed here can also be envisioned.

The carbon nanomaterials of the present disclosure may have various properties. For instance, in some embodiments, the carbon nanomaterial may be hydrophilic (i.e., water soluble). In some embodiments, the carbon nanomaterials of the present disclosure may have both hydrophilic portions and hydrophobic portions. For instance, in some embodiments, the carbon nanomaterials of the present disclosure may have a hydrophilic domain (e.g, a hydrophilic surface) and a hydrophobic domain (e.g., a hydrophobic cavity). The carbon nanomaterials of the present disclosure can also be engineered to possess both hydrophobic and hydrophilic domains, combining high aqueous solubility with the ability to adsorb hydrophobic compounds. In some embodiments, this duality of hydrophilic and hydrophobic domains can result in the formation of structures resembling micelles or liposomes. Such structures can in turn further entrap active agents (such as small drugs) for delivery to a desired site. Hence, an active agent (such as a small molecule drug) can have its own efficacy (e.g., a chemotherapeutic activity) in conjunction with the anti-oxidant activity of the carbon nanomaterial.

The carbon nanomaterials of the present disclosure may also demonstrate very low or limited toxicity in vivo. Furthermore, and as set forth in more detail below, the carbon nanomaterials of the present disclosure can have anti-oxidant activity.

Carbon Nanomaterial Anti-Oxidant Activity

Carbon nanomaterial anti-oxidant activity generally refers to a carbon nanomaterial's ability to prevent oxidation, limit oxidation or eliminate oxidation. Such activities may occur by various mechanisms. For instance, in some embodiments, carbon nanomaterial anti-oxidant activity may occur by the entrapment or sequestration of oxidants or pre-oxidants, such as metals. In some embodiments, carbon nanomaterial anti-oxidant activity may occur by sequestering or scavenging free radicals.

In addition, the carbon nanomaterials of the present disclosure may scavenge free radicals by various mechanisms. In some embodiments, it is envisioned that the carbon core of the carbon nanomaterials can scavenge free radicals. For instance, as illustrated in FIG. 1B, conjugated domains in the carbon core of carbon nanomaterials may receive two RO• species. As a result, two carbon-carbon pi-bonds could be lost, but two new C—O sigma bonds and one new C—C pi bond could be formed without any radical species remaining.

In some embodiments, polymer chains appended to the carbon nanomaterials may scavenge free radicals. In some embodiments, the radical scavenging may lead to the degradation of the polymer chains, as previously reported. *Proc. Nat. Acad. Sci. USA,* 1998 (95):10373-10377.

In some embodiments, the anti-oxidant activity of the carbon nanomaterial may correspond to oxygen radical absorbance capacity (ORAC) values between about 200 to about 15,000. In some embodiments, the anti-oxidant activity of the carbon nanomaterial may correspond to ORAC values between about 200 and about 5,000. In some embodiments, the anti-oxidant activity of the carbon nanomaterial may correspond to ORAC values between about 300 and about 400.

Exemplary ORAC values of suitable but non-limiting carbon nanomaterials are listed in FIG. 1C. As illustrated, the ORAC values of the carbon nanomaterials of the present disclosure can be about 100 times to about 1000 times more potent than current anti-oxidant therapies. For instance, amifostine alone has an ORAC value of about 2.5.

Active Agents

In various embodiments, the therapeutic compositions of the present disclosure may also include one or more active agents. Active agents of the present disclosure generally refer to biologically active compounds, such as compounds that have anti-oxidant activity. For instance, in various embodiments, active agents of the present disclosure may refer to anti-cancer drugs, chemotherapeutics, antioxidants, and anti-inflammatory drugs.

Furthermore, the active agents of the present disclosure may be derived from various compounds. For instance, in various embodiments, the active agents of the present disclosure can include, without limitation, small molecules, proteins, aptamers, DNA, anti-sense oligo nucleotides, miRNA, siRNA, and combinations thereof.

In more specific embodiments, the active agents of the present disclosure may include one or more anti-oxidants. In some embodiments, the anti-oxidants may include, without limitation, ascorbic acid (Vitamin C), glutathione, lipoic acid, uric acid, carotenes, β-carotenes, retinol (Vitamin A), tocopherols, tocotrienols, α-Tocopherol (Vitamin E), ubiquinol (coenzyme Q), melatonin, carotenoids, lycopenes, carotenes, luteins, phenyl N-tert-butyl nitrone (PBN), tirilazad mesylate, tirilizad, propyl gallate, tertiary butylhydroquinone (TBHQ), butylated hydroxyanisole (BHA), butylated hydroxytoluene (BHT), combinations thereof, and derivatives thereof. In further embodiments, anti-oxidants may also include enzymes, such as SOD, PEG-SOD, catalase and peroxiredoxins.

In some embodiments, the active agents of the present disclosure may also include one or more active agents that treat various conditions associated with oxidative stress. For instance, in some embodiments, the therapeutic compositions of the present disclosure may include active agents that treat traumatic brain injury, ischemia, anoxic encephalopathy, hypoxic or ischemic encephalopathy in neonates, cerebrovascular dysfunction, hemorrhagic shock, hypoxia, hypotension, Alzheimer's disease, Parkinson's disease, multiple sclerosis, amyotrophic lateral sclerosis, liver disease, non-alcoholic fatty liver disease, diabetes, stroke, inflammation, spinal cord injury, central nervous system injury or neuropathy, organ transplantation (treatment of the organ or the patient), or combinations of such conditions.

In more specific embodiments, the therapeutic compositions of the present disclosure may include riluzole as an active agent for treatment of conditions associated with amyotrophic lateral sclerosis. In further embodiments, the therapeutic compositions of the present disclosure may include anti-oxidants, anti-inflammatory drugs, anti-cancer drugs, anti-diabetic drugs, and combinations thereof.

In addition, the active agents of the present disclosure may have various secondary properties. For instance, in some embodiments, the active agents may be hydrophobic. In fact, an advantage of the carbon nanomaterials of the present disclosure is the effective delivery of hydrophobic active agents that may have been otherwise insoluble. Such hydrophobic agents can be associated with various carbon nanomaterials for direct delivery to a desired site without requiring the use of moieties that increase solubility but limit active agent efficacy.

In addition, the active agents of the present disclosure may be associated with carbon nanomaterials in various manners. For instance, in some embodiments, the active agents may be non-covalently associated with carbon nanomaterials, such as through sequestration, adsorption, ionic bonding, dipole-dipole interactions, hydrogen bonding, Van der Waals interactions, and other types of non-covalent associations.

In some embodiments, the active agents may be non-covalently sequestered within a cavity, domain or surface of a carbon nanomaterial. In some embodiments, the active agents may be sequestered from their surrounding environment by non-covalent association with a carbon nanomaterial's solubilizing groups. In more specific embodiments where the carbon nanomaterial includes hydrophobic domains and hydrophilic domains, the active agent may be associated with a hydrophobic domain. In further embodiments, a hydrophobic active agent may be associated with a hydrophobic domain of a carbon nanomaterial. In some embodiments, this duality of hydrophilic and hydrophobic domains can result in the formation of structures resembling micelles or liposomes that can further entrap the active agents for delivery.

In further embodiments, the active agents of the present disclosure may be covalently associated with carbon nanomaterials. For instance, in some embodiments, the active agents of the present disclosure may be covalently associated with an active agent through a linker molecule, through a chemical moiety, or through a direct chemical bond between the active agent and the carbon nanomaterial. In some embodiments, the active agent may be covalently associated with the carbon nanomaterial through a cleavable moiety, such as an ester bond or amide bond. In some embodiments, the cleavable moiety may be a photo-cleavable moiety or a pH sensitive cleavable moiety. Additional modes by which active agents may be covalently or non-covalently associated with carbon nanomaterials can also be envisioned.

In some embodiments, the therapeutic compositions of the present disclosure may include a single active agent. In some embodiments, therapeutic compositions of the present disclosure may include multiple active agents. In some embodiments, therapeutic compositions of the present disclosure may include carbon nanomaterials without any active agents.

Tracers

The therapeutic compositions of the present disclosure can also be associated with one or more tracers, such as an MRI tracer. In more specific embodiments, the tracer(s) associated with therapeutic compositions may include a gadolinium tracer, such as $Gd^{3+}$. In further embodiments, the tracer may include, without limitation, at least one of fluorescent molecules, Qdots, radioisotopes, and combinations thereof. In various embodiments, such tracers can be used to track in real-time the location, distribution and delivery of administered therapeutic compositions. Thus, such embodiments would allow a physician to follow the degree of therapeutic composition binding to desired sites, monitor the biological half-life of the therapeutic compositions, and monitor accumulation in non-target organs such the kidney and liver.

Targeting Agents

The therapeutic compositions of the present disclosure may also be associated with one or more targeting agents. Targeting agents of the present disclosure generally refer to compounds that have recognition activity for a marker, such as one or more markers related to oxidative stress. Therefore, targeting agents of the present disclosure may be utilized in various embodiments to direct therapeutic compositions to desired sites that are associated with oxidative stress.

In various embodiments, targeting agents may include, without limitation, antibodies, RNA, DNA, aptamers, small molecules, dendrimers, proteins, and combinations thereof. In more specific embodiments, the targeting agent can be a monoclonal antibody or a polyclonal antibody. In particular embodiments, the antibody may be a chimeric antibody or an antibody fragment (e.g., Fab fragment of a monoclonal antibody).

In addition, targeting agents may be associated with carbon nanomaterials in various manners. In some embodiments, targeting agents may be non-covalently associated with carbon nanomaterials, such as through sequestration, adsorption, ionic bonding, dipole-dipole interactions, hydrogen bonding, Van der Waals interactions, and other types of non-covalent associations.

In more specific embodiments, targeting agents may be non-covalently sequestered on a surface of a carbon nanomaterial. In some embodiments, targeting agents may be covalently associated with carbon nanomaterials. In some embodiments, targeting agents may be covalently and non-covalently associated with carbon nanomaterials.

In more specific embodiments, the targeting agents of the present disclosure may be covalently associated with carbon nanomaterials through a linker molecule, through a chemical moiety, or through a direct chemical bond between the targeting agent and the carbon nanomaterial. In some embodiments, the targeting agent may be covalently associated with the carbon nanomaterial through a cleavable moiety, such as an ester bond or amide bond. In some embodiments, the cleavable moiety may be a photo-cleavable moiety or a pH sensitive cleavable moiety. Additional modes by which targeting agents may be covalently or non-covalently associated with carbon nanomaterials can also be envisioned.

Markers

As set forth previously, targeting agents of the present disclosure can target various markers related to oxidative stress. In some embodiments, such markers may be on a surface of a cell. In some embodiments, such markers may be within cells. In some embodiments, such markers may include epitopes associated with oxidative stress. In some embodiments, such epitopes may be over-expressed or up-regulated in response to oxidative stress. In some embodiments, such epitopes may be over-expressed or up-regulated in response to oxidative stress on the surface of a cell, such as a cancerous cell.

In more specific embodiments, the marker is a cell surface protein that is over-expressed or up-regulated in response to oxidative stress. Non-limiting examples of such markers include transferrin receptors, angiotensin receptors, cannabinoid receptors, epidermal growth factor receptors, p-selectin molecules, adhesion molecules such as intracellular adhesion molecule (ICAM), channel proteins such as the Sulfoneurea Receptor 1, and combinations thereof. In more specific embodiments, such markers may be over-expressed or up-regulated on endothelial cells in response to oxidative stress, such as traumatic brain injury. In some embodiments, suitable markers may also include transport proteins, such as transport proteins that can direct therapeutic compositions into the central nervous system through the blood brain barrier.

Methods of Treating Oxidative Stress

Further embodiments of the present disclosure pertain to methods of treating oxidative stress in a subject. Such methods generally include administering one or more of the above-described therapeutic compositions to the subject.

Oxidative Stress

Oxidative stress generally refers to an imbalance between the production and elimination of reactive oxygen species (ROS). Oxidative stress has been implicated in a number of diseases, including neurological injury. For instance, oxidative injury to the vasculature is a feature of many conditions, including acute neurological injury, such as cerebrovascular dysfunction in mild traumatic brain injury (mTBI).

The methods and therapeutic compositions of the present disclosure may be used to treat oxidative stress that is associated with or related to one or more conditions. Such conditions may include, without limitation, traumatic brain injury, ischemia, anoxic encephalopathy, hypoxic or ischemic encephalopathy, cerebrovascular dysfunction, hemorrhagic shock, hypoxia, hypotension, Alzheimer's disease, Parkinson's disease, multiple sclerosis, amyotrophic lateral sclerosis, liver disease, non-alcoholic fatty liver disease, diabetes, stroke, inflammation, spinal cord injury, central nervous system injury or neuropathy, organ transplantation (treatment of the organ or the patient), and combinations thereof. In some embodiments, the oxidative stress to be treated may also be associated with or related to organ transplantation. In further embodiments, the oxidative stress may be associated with or related to damage to the central nervous system, including the spinal cord and surrounding tissues. In more specific embodiments, the methods and compositions of the present disclosure may be used to treat oxidative stress associated with traumatic brain injury or non-alcoholic fatty liver disease.

Mechanisms of Treating Oxidative Stress

The methods and compositions of the present disclosure can be utilized to treat oxidative stress by various mechanisms. In some embodiments, oxidative stress may be treated by reducing ROS levels in the subject. This can include localized ROS level reduction at a treated site in a subject. In some embodiments, the methods and compositions of the present disclosure may be utilized to reduce ROS levels in a subject to homeostatic levels, or levels before the subject suffered from oxidative stress. In some embodiments, the methods and compositions of the present disclosure may be utilized to reduce ROS levels in a subject by about 5% to about 50%, by about 50% to about 75%, or by about 60% to about 75%.

In some embodiments, oxidative stress may be treated by attenuating the generation of ROS. In some embodiments, oxidative stress may be treated by mitigating the ROS-induced consumption of endogenous anti-oxidant enzymes.

In some embodiments, the reduction of ROS levels may be determined by changes in the intensity of a dye or marker that is specific for one or more reactive oxygen species. For instance, the reduction of ROS levels may be determined in some embodiments by changes in di hydroxyethidium (DHE) fluorescence intensity. DHE reacts with ROS to form 2-hydroxyethidium, which possesses red fluorescence when excited near 480 nm. Thus, the increase in red fluorescence can be proportional to the ROS in the sample.

Furthermore, various concentrations of therapeutic compositions may be used to treat oxidative stress. Though therapeutic concentration ranges are not limiting, it may be preferable to administer therapeutic composition concentrations that are not too potent to mitigate normal or necessary biological processes. Hence, in some embodiments, it may be desirable to choose therapeutic composition concentration ranges that are suitable for treating oxidative stress with minimal effects on normal or necessary biological processes.

Reactive oxygen species that may be targeted by the methods and compositions of the present disclosure are also not limiting. In some embodiments, the reactive oxygen species may include, without limitation, nitric oxides (NO), superoxides (SO), hydroperoxyls, hydrogen peroxide, oxygen radicals, hydroxyl radicals, organic hydroperoxides, alkoxy radicals, peroxy radicals, hypochlorous acids, peroxynitrites, and combinations thereof.

In more specific embodiments, the methods and compositions of the present disclosure may treat oxidative stress by restoring or normalizing SO and NO levels in a subject's vasculature, such as the cerebral vasculature, or within the central nervous system (CNS) itself. In some embodiments, such treatments may also improve or enhance a subject's blood flow, such as cerebral blood flow (CBF). In some embodiments, the treatments may reduce ROS levels without significant effects in a subject's body weight or feeding behavior.

Subjects

The therapeutic compositions of the present disclosure may be administered to various subjects. In some embodiments, the subject is a human being, such as a human being suffering from oxidative stress. In some embodiments, the subject is a human being suffering from TBI-induced oxidative stress. In more specific embodiments, the subject may be a combat soldier suffering from TBI, or an automotive accident victim. In additional embodiments, the subjects may be non-human animals, such as mice, rats, other rodents, or larger mammals, such as dogs, monkeys, pigs, cattle and horses.

Modes of Administration

The therapeutic compositions of the present disclosure can also be administered to subjects by various methods. For instance, the therapeutic compositions of the present disclosure can be administered by oral administration (including gavage), inhalation, subcutaneous administration (sub-q), intravenous administration (I.V.), intraperitoneal administration (I.P.), intramuscular administration (I.M.), intrathecal injection, and combinations of such modes. In further embodiments of the present disclosure, the therapeutic compositions of the present disclosure can be administered by topical application (e.g, transderm, ointments, creams, salves, eye drops, and the like). Additional modes of administration can also be envisioned.

The therapeutic compositions of the present disclosure may also be administered in a single dose or multiple doses throughout a time period. For instance, in some embodiments, the therapeutic compositions of the present disclosure may be administered to a subject in two separate doses.

In addition, the therapeutic compositions of the present disclosure may be administered to localized sites in a subject, such as tissue or vasculature that have suffered from oxidative stress. For instance, the therapeutic compositions of the present disclosure may be injected directly into the brain of a subject that has recently suffered a traumatic brain injury, or the spinal column of a subject that recently suffered an SCI.

The methods and compositions of the present disclosure may also be utilized for targeted treatment. For instance, in some embodiments, therapeutic compositions may be associated with targeting agents that are specific for endothelial cell epitopes that are over-expressed or up-regulated in response to oxidative stress (e.g., PEG-HCCs with anti-p-selectin antibodies). Therefore, upon administration, the therapeutic compositions can be directed to vasculature sites that have inflicted oxidative stress (e.g., brain endothelial cells and the cerebral vasculature of a subject suffering from TBI).

In various embodiments, the therapeutic compositions of the present disclosure may be co-administered with other therapies. For instance, in some embodiments, the therapeutic compositions of the present disclosure may be co-administered along with anti-cancer drugs. This could be especially helpful in cases where the anti-cancer drug causes neuropathy, and where the neuropathy could be mitigated by the anti-oxidant properties of the carrier composition (e.g., PEG-HCCs). Other modes of co-administration can also be envisioned.

Methods of Formulating Therapeutic Compositions

Additional embodiments of the present disclosure generally pertain to methods of making therapeutic compositions of the present disclosure. Such methods generally comprise: (1) associating a nanomaterial with one or more active agents; and (2) associating one or more targeting agents with the nanomaterial. In some embodiments, one or more of the above-mentioned associations may occur non-covalently, such as by sequestration, adsorption, ionic bonding, dipole-dipole interactions, hydrogen bonding, Van der Waals interactions, and other types of non-covalent interactions. In further embodiments, one or more of the associations may occur by covalent bonding.

In various embodiments, the aforementioned associations may occur simultaneously or sequentially. In some embodiments, the associations may occur by mixing a nanomaterial with one or more active agents and targeting agents.

Therapeutic compositions of the present disclosure can also be formulated in conventional manners. In some embodiments, the formulation may also utilize one or more physiologically acceptable carriers or excipients. The pharmaceutical compositions can also include formulation materials for modifying, maintaining, or preserving various conditions, including pH, osmolarity, viscosity, clarity, color, isotonicity, odor, sterility, stability, rate of dissolution or release, and/or adsorption or penetration of the composition. Suitable formulation materials include, but are not limited to: amino acids (e.g., glycine); antimicrobials; antioxidants (e.g., ascorbic acid); buffers (e.g., Tris-HCl); bulking agents (e.g., mannitol and glycine); chelating agents (e.g., EDTA); complexing agents (e.g., hydroxypropyl-beta-cyclodextrin); and the like. Additional methods of formulating therapeutic compositions can also be envisioned.

Applications and Advantages

The therapeutic compositions and methods of the present disclosure provide numerous applications and advantages. For instance, the therapeutic compositions of the present disclosure may be used in numerous variations to treat oxidative stress associated with numerous conditions, such as traumatic brain injury, ischemia, anoxic encephalopathy, hypoxic or ischemic encephalopathy, cerebrovascular dysfunction, hemorrhagic shock, hypoxia, hypotension, Alzheimer's disease, Parkinson's disease, multiple sclerosis, amyotrophic lateral sclerosis, liver disease, non-alcoholic fatty liver disease, diabetes, stroke, inflammation, spinal cord injury, central nervous system injury or neuropathy, organ transplantation (treatment of the organ or the patient) and combinations thereof. In some embodiments, the methods and compositions of the present disclosure may be used to treat oxidative stress induced by stroke, hypoxia, organ transplantation, injury to the neurovascular unit (e.g, TBI), hypotension, resuscitation, blood reperfusion, and other similar conditions.

In more specific embodiments, the methods and compositions of the present disclosure may be used to treat cerebrovascular dysfunction following TBI. As set forth in more detail in the Examples below, such methods may be used to rapidly restore cerebral blood flow (CBF) in TBI patients. As also set forth in more detail in the Examples below, the methods and compositions of the present disclosure may be used to treat oxidative stress associated with non-alcoholic Fatty liver disease (NALFD). The methods and compositions of the present disclosure can also be used to treat oxidative stress associated with Alzheimer's disease, multiple sclerosis, and ALS.

In addition, the methods and compositions of the present disclosure provide numerous advantages in treating oxidative stress. For instance, the methods and compositions of the present disclosure may significantly reduce ROS levels in subjects suffering from oxidative stress with minimal side effects and toxicities. Furthermore, due to the anti-oxidative nature of the carbon nanomaterials, the methods and compositions of the present disclosure can be more effective than current methods in treating oxidative stress.

Additional Embodiments

Reference will now be made to more specific embodiments of the present disclosure and experimental results that provide support for such embodiments. However, Applicants note that the disclosure below is for illustrative purposes and is not intended to limit the scope of the claimed subject matter in any way.

EXAMPLE 1

PEG-HCCs for Treatment of Oxidative Stress Associated with mTBI

Example 1 pertains to the design of PEG-HCCs for targeted therapy of cerebrovascular dysfunction in mild traumatic brain injury. TBI involves the elaboration of oxidative stress. Currently, there is no clinically effective antioxidant treatment for these pathologies. Here, Applicants report that PEG-HCCs possess innate antioxidant activity and can be rapidly targeted via an antibody to the p-selectin antigen in a model of injured cultured brain endothelial cells. One immediate application of this therapy is to vascular dysfunction that accompanies TBI and worsens outcome in the face of systemic hypotension.

Oxidative stress and vascular dysfunction is a prominent feature of TBI, especially when accompanied by secondary insults, such as hemorrhagic hypotension. Cerebrovascular dysfunction is evident even in mild TBI (mTBI), and if complicated by hypotension, causes both structural lesions and behavioral dysfunction. In the case of an acute injury, there is both an acute elaboration of oxidative radicals and an extended period of oxidative stress as the initial injury sets off a cascade that can last for days. Consequently, antioxidant therapies have been investigated for treating TBI.

Extensive research has explored using small molecule antioxidants, such as PBN and tirilazad mesylate, or stabilized enzymes, such as PEG-SOD, to combat oxidative stress. Unfortunately, none of these potential therapies has shown efficacy in clinical trials, and there are no Food and Drug Administration-approved antioxidant therapies for these conditions.

The generation of oxidative radicals is rapid following TBI. Secondary insults such as hypotension, a major contributor to poor outcome in TBI, are additional sources of oxidative radical generation with several bursts of superoxide documented throughout the course of TBI and hypotension and reperfusion. Moreover, Applicants' previous work has shown that PEG-SOD has only small and transient effects. Hence, there is a need to find new classes of biologically compatible antioxidants.

Here, Applicants show that PEG-HCCs possess antioxidant activity potent enough to reduce oxidative stress in vitro and can be targeted to a model of injured brain endothelial cells expressing p-selectin antigen. P-selectin expression is increased in brain endothelial cells following traumatic brain injury, and possibly systemically depending on the trauma mechanism. These results suggest that targeted PEG-HCCs are potential therapeutics for oxidative stress-induced cerebrovacular dysfunction from TBI.

EXAMPLE 1A

Materials and Methods

Preparation of PEG-HCCs

PEG-HCCs were prepared as previously described and sterile filtered using a 0.20 μm pore size membrane. *ACS Nano.* 2010 (4): 4621-4636. Preliminary toxicity and biodistribution studies indicate that these nanoparticles are not acutely toxic. These PEG-HCCs can be loaded with hydrophobic drugs, and when mixed with an antibody, a noncovalent formulation capable of targeted drug delivery in vitro is formed. Based on the antibody/PEG-HCCs interaction previously reported, Applicants mixed p-selectin antibody with the PEG-HCCs and evaluated the targeting properties of the system.

It has been found that iron forms deposits in patients with mTBI. In order to explore the behavior of the iron when combined with PEG-HCCs, Applicants ran the following iron chelator assays: benzoate hydroxylation and ascorbate oxidation. Ascorbic acid (cat # AC40147), benzoic acid (cat # AC22180), iron(II) sulfate heptahydrate (cat # AC42373), iron(III) chloride hexahydrate (cat # AC21709), and the disodium ethylenediamine tetraacetate (EDTA, cat # E4884), as obtained from Fisher Scientific. Deferoxamine mesylate salt (DFO, cat#D9533) was obtained from Sigma-Aldrich.

ORAC Assay

The following solutions were prepared daily: phosphate buffer at pH 7.4 (PBS, 75 mM), fluorescein sodium salt (0.1 and 0.2 μM), α,α'-azodiisobutyramidine dihydrochloride (AAPH, 0.15 M), racemic 6-hydroxy-2,5,7,8-tettramethyl-chromate-2-carboxilic acid (trolox, 400 μM). The experiment was carried out in a 96-well plate and each sample was analyzed by triplicate, as shown in Table 1.

TABLE 1

ORAC Assay Design.
Table 1. ORAC Assay Design

|   | 1$^{st}$ step | | 2$^{nd}$ step |
| --- | --- | --- | --- |
| Assay | 120 μL of Fluorescein | 20 μL of Sample | 60 μL of AAPH |
| Control 1 (no AAPH) | 120 μL of Fluorescein | 20 μL of Sample | 60 μL of PBS |
| Control 2 (no Fluorescein) | 120 μL of PBS | 20 μL of Sample | 60 μL of AAPH |

Trolox and phosphate buffer (blank) were run as samples. At least 3 standards of trolox were run for the calibration curve After the addition of the fluorescent probe or PBS and sample (1$^{st}$ step) to the assigned wells, the plate was incubated at 37° C. for 15 min in a TECAN plate reader. Then, the ice-cold AAPH or PBS was added (2$^{nd}$ step) and the fluorescent intensity at 530 nm (485 nm excitation) was measured every minute for 2 h. Data were analyzed as follows: control 2 (background) was subtracted from the assay and control 1. The assay well results were divided by the control 1 and the area under the curve (AUC) was determined by equation 1.

$$AUC = 1 + \frac{f1}{f0} + \frac{f2}{f0} + \frac{f3}{f0} + \ldots + \frac{fi}{f0} \quad \text{(Eq. 1)}$$

Trolox mass equivalents (TME) were determined by equation 2.

$$TME = \frac{AUC_{Sample} - AUC_{Blank}}{AUC_{Trolox} - AUC_{Blank}} \times \frac{Trolox_{mass(mg)}}{Sample_{mass(mg)}} \quad \text{(Eq. 2)}$$

Benzoate Hydroxylation

This assay is based on the hydroxylation of benzoate when exposed to iron and $H_2O_2$, producing the fluorescent compounds 2,3,4-trihydroxybenzoate (308 nm excitation and 410 nm emission) with the major products 2-hydroxybenzoic acid salt or salicylic acid salt at pH 7.4. In brief, the following solutions were freshly prepared before each run according to reported procedures: benzoic acid (3 mM, recrystallized from hot water), $FeCl_3$ (1.80 mM), $FeSO_4$ (1.80 mM), methoxypolyethylene glycol amine polymer (PEG MW 5,000, 0.02 mg/mL) and PEG-HCCs (0.02 mg/mL). EDTA (0.60 mM) and DFO (0.60 mM) were used as the positive and negative control, respectively. The benzoic acid was incubated at room temperature for 1 h in the phosphate buffer (pH 7.4) with 5 mM of $H_2O_2$ and the ferric or ferrous iron salt, in the presence of one of the controls or the PEG-HCCs. The reaction was started by the addition of any the iron salts and kept in dark. Salicylate was used to determine the quenching effect of the materials.

Ascorbate Oxidation

This assay was performed in a similar way to that described previously. Rad. Res. Comms. 1985 (1):349-353; J Biochem Biophys Methods 1988 (16):27-40; Radiat Res. 1996 (145):532-541. Briefly, the following solutions were prepared prior to each experiment: ascorbic acid (0.1 mM), $FeCl_3$ (0.60 mM), potassium phosphate buffer (50 mM, pH 7.4, cleaned with Chelex resin), EDTA (0.02 mg/mL previously recrystallized three times from hot water), DFO (0.02 mg/mL), and PEG-HCCs (0.02 mg/mL). The ascorbate absorbance at 265 nm was measured after 1, 5 and 30 min using a TECAN plate reader.

Cell Culture

Murine brain endothelioma (bEnd.3, CRL 2299, ATCC, Manassas, Va.) were cultured in DMEM-F12 (50:50) with 4 mM L-glutamine media, supplemented with 10% fetal bovine serum (both from HyClone) and 1% Pen Strep (+10,000 u/mL penicillin/+10,000 μg/mL streptomycin, from GIBCO). During the second week, between the 4th and 6th passage, cell experiments were performed.

P-Selectin Targeting bEnd.3 cells were grown on glass covers to 60-70% confluence in 6 well plates. P-selectin-targeted PEG-HCCs (ps/PEG-HCCs) were synthesized by adding 0.01 μg anti-p-selectin antibody (Santa Cruz Biotechnology Inc., Santa Cruz, Calif.) to 0.49 μg PEG-HCCs and incubating at RT for 1 h. The antibody possesses hydrophilic and hydrophobic domains that allow the nanomaterial to sequester it. The bEnd.3 cells were treated with histamine (20 μM) to induce p-selectin expression or 1×PBS (histamine diluent) as a control. (McEver et al., 1989). After a 15 min incubation at 37° C., the cells were treated with vehicle (1×PBS), PEG-HCCs (0.49 μg), or ps/PEG-HCCs. Cells were incubated for 15 min and then washed twice and fixed with methanol. Cells were washed and stained with anti-PEG (Epitomics, Burlingame, Calif.) and anti-p-selectin antibodies (Santa Cruz Biotechnology Inc, Santa Cruz, Calif.). After washing, cells were probed with fluorescent secondary antibodies to the anti-PEG and anti-p-selectin antibodies (Invitrogen, Carlsbad, Calif.). Glass covers were mounted on slides and fluorescent images were captured on an epifluorescent microscope.

Intracellular Superoxide Cell Culture Model bEnd.3 cells were cultured to 50-80% confluence in 6 well plates in 2 mL of culture media. The cells were treated with vehicle (1×PBS), PEG-HCCs, ps/PEG-HCCs, or p-selectin antibody alone (same concentration as found in ps/PEG-HCCs). After 15 min, the cells were treated with 10 μL of 2 mM Antimycin A (AntA) or 10 μL ethanol (control). AntA has been shown to induce intracellular superoxide radical production. (Han et al., 2008). The cells were incubated at 37° C. for 40 min, at which point 2 μL of 10 mM dihydroethidine (DHE) (Zhao et al. 2005). (in 50%/50% DMSO/1×PBS) was added to wells or 50%/50% DMSO/1×PBS (control). DHE reacts with ROS to form 2-hydroxyethidium, which possesses red fluorescence when excited near 480 nm; thus, the increase in red fluorescence is proportional to the ROS in the sample. (Zhao et al., 2005). The cells were then placed on ice, trypsinized, and washed twice. Cells were subsequently counted and stained with SytoxRed (viability stain). 10,000 cells were analyzed per treatment group using the TXRED channel (DHE) and SytoxRed to assess cell viability.

EXAMPLE 1B

Anti-Oxidant Activity of PEG-HCCs

Figure 2A:
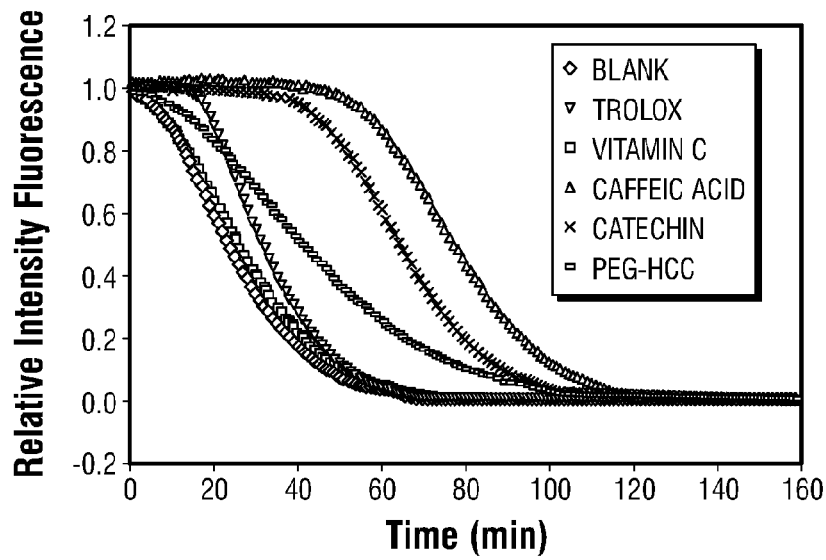
FIG. 2A show fluorescence decay curves obtained during the evaluation of vitamin C, caffeic acid, catechin, and PEG-HCCs.
Figure 2B:
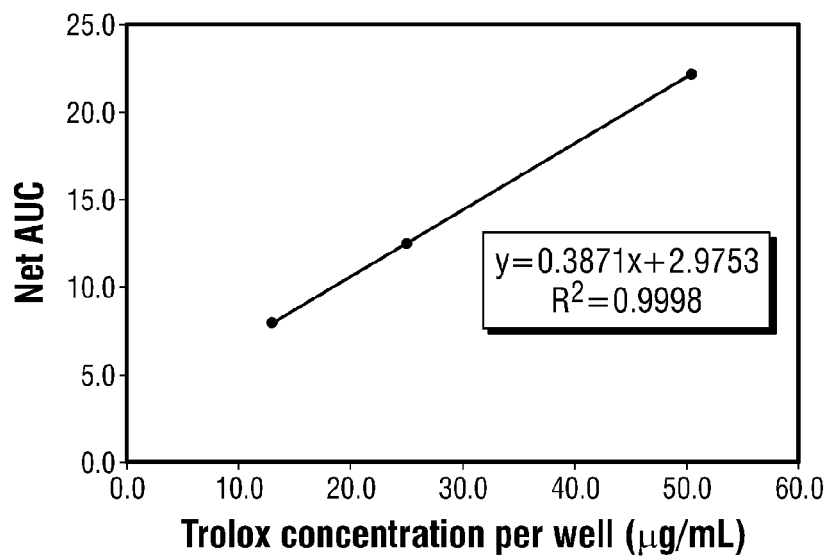
FIG. 2B shows linear regression of net area under the curve (AUC) of trolox corresponding to the decay curve A.
Figure 2C:
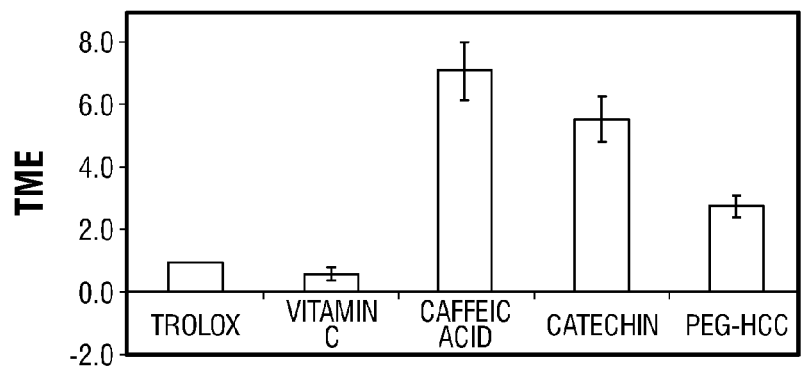
FIG. 2C provides trolox-measured equivalent (TME) values corresponding to the different known antioxidants and carbon nanomaterials, respectively. Trolox is the reference compound ($TME_{trolox}=1$).
Figure 8A:
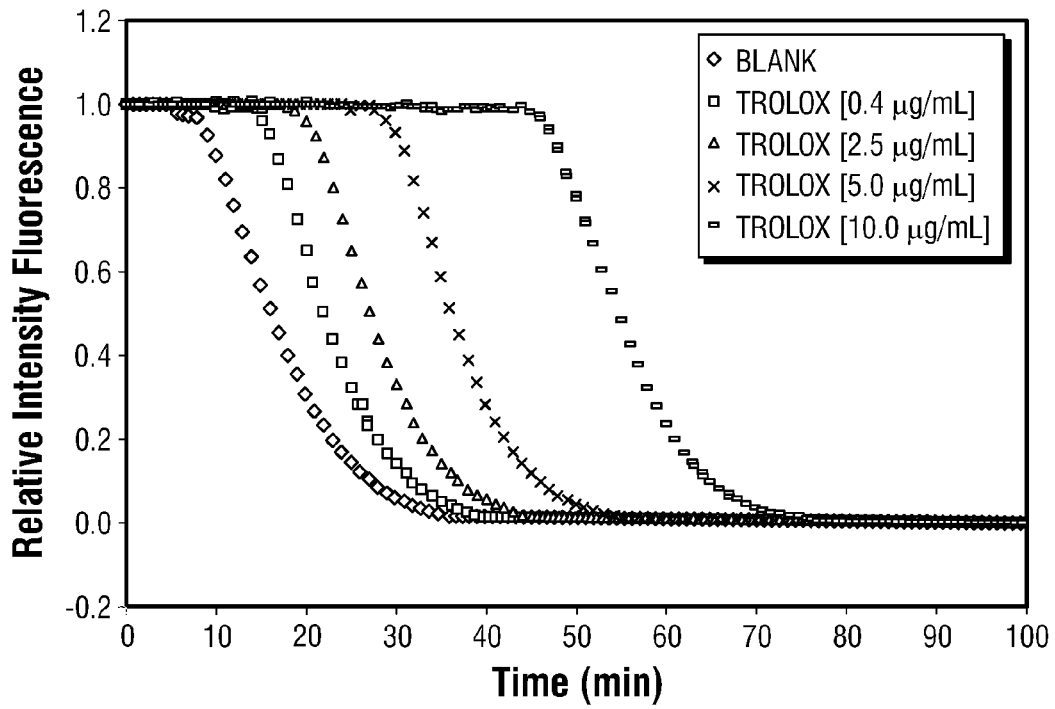
FIG. 8A shows trolox concentration effect on fluorescence decay curve induced by 2,2'-azobis(2-amidino-propane) dihydrochloride (AAPH).
Figure 8B:
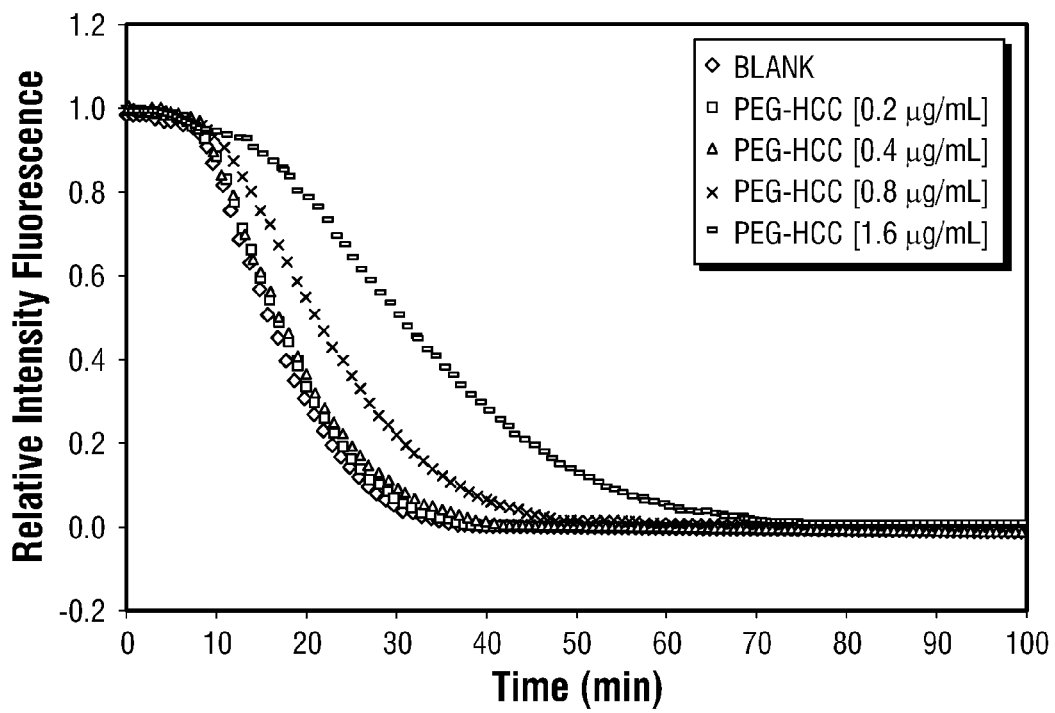
FIG. 8B shows PEG-HCCs concentration effect on fluorescence decay curve after AAPH addition.
Figure 8C:
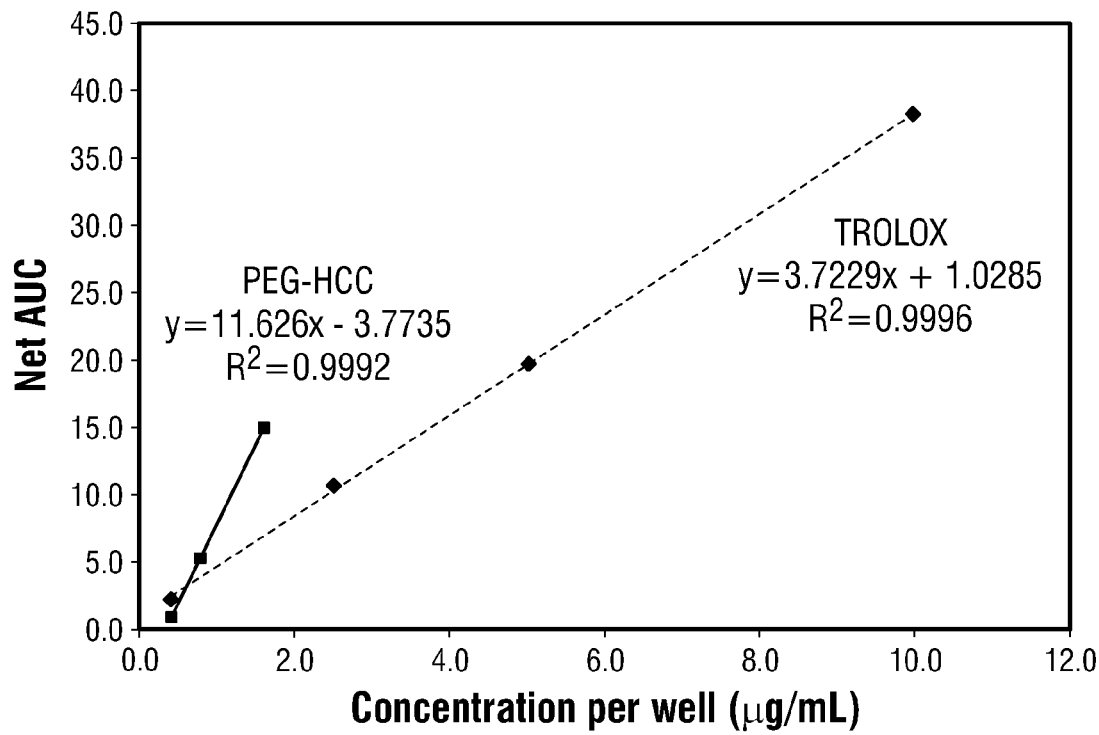
FIG. 8C shows linear regression of net area under the curve (AUC) of trolox and PEG-HCC. An approximation of the Trolox mass equivalent can be estimated dividing the slope of the sample by the trolox slope ($TME_{PEG-HCC}$=3.12).
Figure 9:
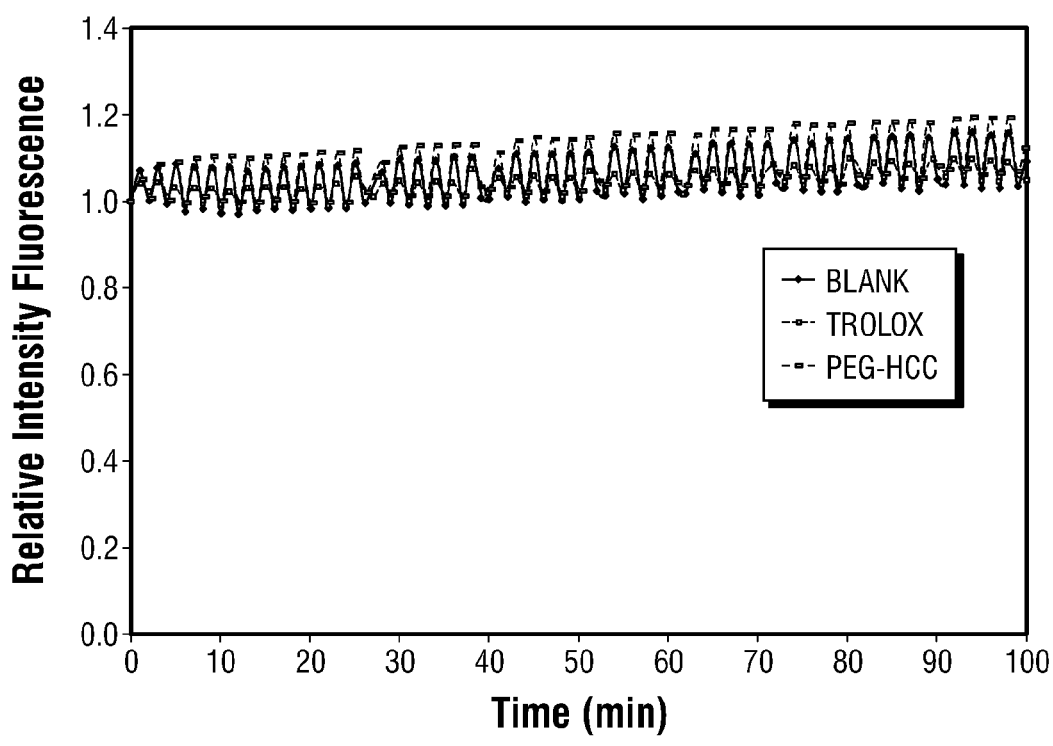
FIG. 9 shows typical fluorescence curves obtained when PBS, Trolox, PEG-HCCs, and the fluorescent probe were not mixed with AAPH (control 1). Note that fluorescent intensity remained stable during the experiment and the intensity is not affected by the carbon nanomaterials.
Figure 11C:
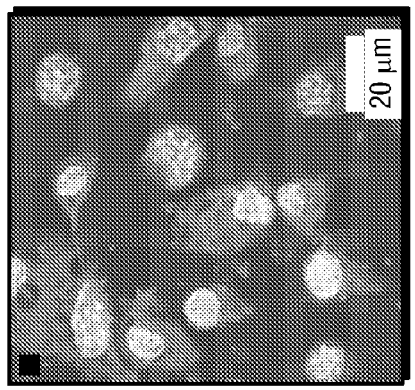
FIG. 11C shows overlapped images of the PEG-HCC-treated cells.
Figure 11F:
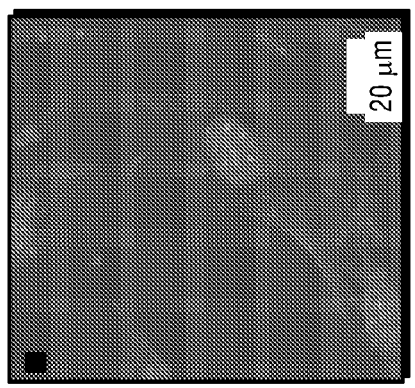
FIG. 11F shows overlapped images of the PEG-treated cells.
Figure 11B:
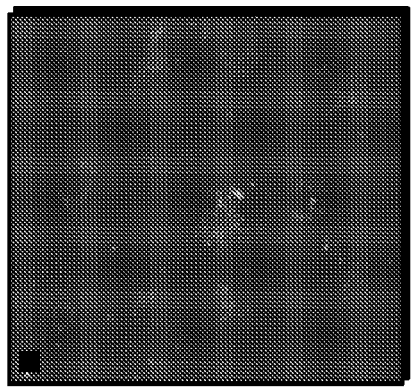
FIG. 11B shows PEG-stained cells.
Figure 11E:
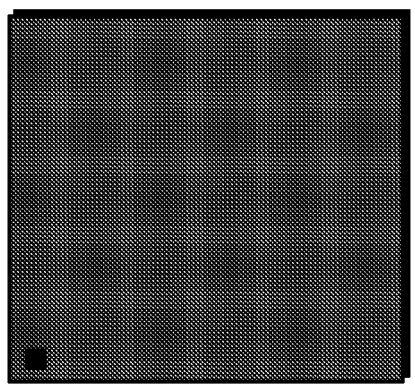
FIG. 11E shows PEG-stained cells.
Figure 11A:
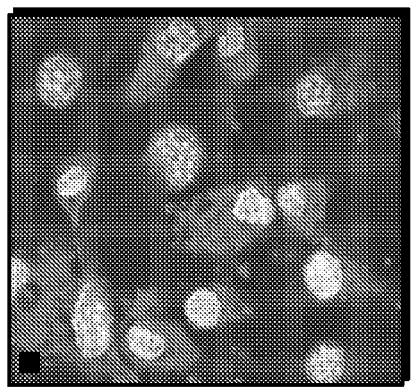
FIG. 11A shows the membrane and nuclei-stained cells.
Figure 11D:
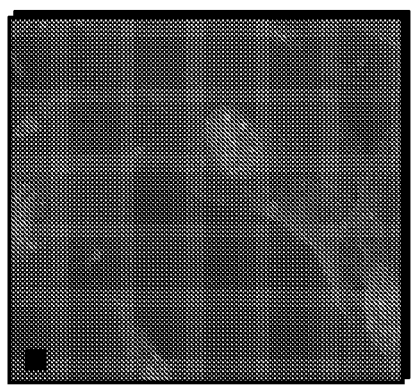
FIG. 11D shows the membrane and nuclei stained cells.

The antioxidant capacity of the PEG-HCCs was compared by the ORAC assay to known antioxidants vitamin C, caffeic acid, and catechin. ORAC measures antioxidant capacity by the ability of a substance to inhibit the loss of fluorescence caused by the oxidation of a fluorescent dye by peroxyl radicals formed during the thermal decomposition of the AAPH without the assistance of any metal. The linear relationship between the net area and antioxidant concentration was evaluated by using a set of trolox and PEG-HCCs standards. See FIGS. 2 and 8-9. Table 2 summarizes the correlation coefficient, slope, and intercept of the trolox standard curves obtained in each run.

TABLE 2

Summary of Trolox Calibration curve for each run related to known antioxidants evaluation (Y(Net. AUC) = a + b X(mg/mL)).

| Run | $R^2$ | Slope (b) | Intercept (a) | Observations |
|---|---|---|---|---|
| 1 | 0.9982 | 424.9 ± 18.1 | 0.677 ± 0.599 | 3 standards |
| 2 | 0.9991 | 399.9 ± 12.1 | −0.325 ± 0.399 | 3 standards |
| 3 | 0.9991 | 431.0 ± 32.5 | 3.364 ± 0.439 | 3 standards |
| 4 | 0.9998 | 387.1 ± 5.4 | 2.980 ± 0.179 | 3 standards |
| Average | 0.9990 | 410.7 ± 20.7 | 1.674 ± 1.784 | |

Accepted $R^2$ >0.9900. Slope and intercept errors calculated at 95% confidence

The assay was consistent for all concentrations tested. For comparison and TME calculations, the concentrations of vitamin C, caffeic acid, catechin, trolox, and PEG-HCCs were kept constant at 1.6 μg/mL. See FIG. 2A and Table 3.

TABLE 3

THE corresponding to the known antioxidants evaluation. The concentration of each compound was the same (1.61. tg/mL).

| Run | Vitamin C | Caffeic Acid | Catechin | Trolox | PEG-HCC |
|---|---|---|---|---|---|
| 1 | 1.02 | 7.04 | 5.68 | 1.00 | 2.96 |
| 2 | 0.78 | 9.68 | 7.58 | 1.00 | 3.73 |
| 3 | 0.30 | 5.38 | 4.25 | 1.00 | 2.07 |
| 4 | 0.22 | 6.43 | 4.78 | 1.00 | 2.24 |
| Average | 0.58 | 7.13 | 5.57 | 1.00 | 2.75 |
| SD | 0.38 | 1.83 | 1.46 | n.a | 0.76 |
| SE | 0.19 | 0.92 | 0.73 | n.a | 0.38 |

According to these results, PEG-HCCs showed higher antioxidant capacity than vitamin C, but lower than catechin and caffeic acid. See FIG. 2B. This range of antioxidant potential demonstrates that the PEG-HCCs possess biologically relevant antioxidant capacity. Without being bound by theory, Applicants envision that this anti-oxidant property is due to the conjugated domains in the carbon core. When these domains receive two RO• species, two carbon-carbon pi-bonds could be lost but two new C—O sigma bonds and one new C—C pi bond could be formed without any radical species remaining. See FIG. 1B.

EXAMPLE 1C

The Role of Chelation in PEG-HCC Antioxidant Activity

Iron accumulation in the pathology of TBI has been reported for mice and humans based on magnetic resonance imaging. It is known that $Fe^{+2}$ and $Fe^{+3}$ form lipid alkoxy radical and peroxyl radicals respectively, which induced the production of the neurotoxic aldehydes. Therefore, it is important to determine if the nanoparticles stimulate the iron redox cycle (similar to EDTA) or inhibit it (similar to DFO). In order to assess this property, chelation assays were performed.

Benzoate Hydroxylation Assay

Figure 3A:
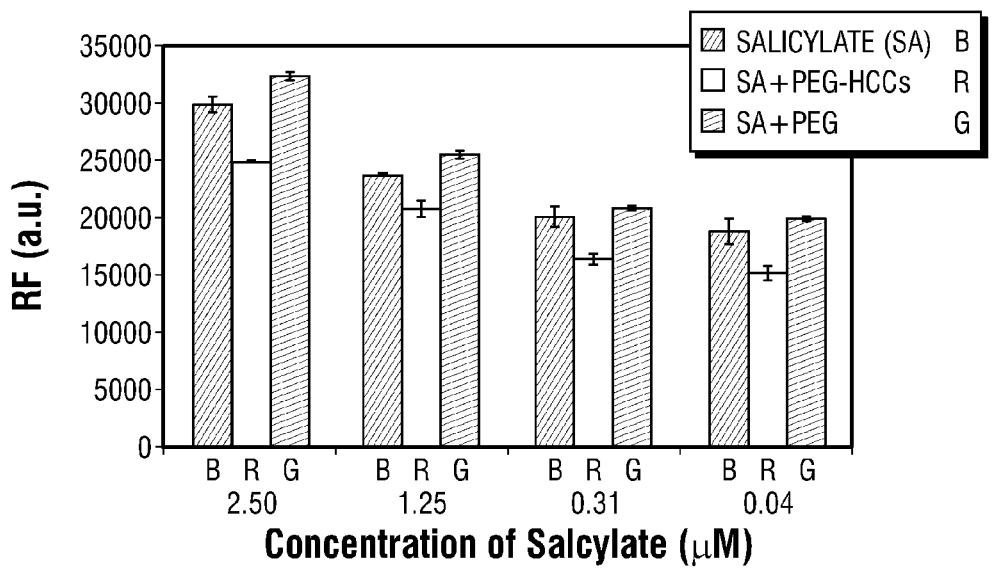
FIG. 3A provides typical fluorescence quenching evaluation of PEG-HCCs, PEG chains, and salicylate (SA) obtained in each experiment. PEG-HCCs can decrease the fluorescence intensity about ~20% while PEG can enhance it up to ~10% on average. These estimations were used for corrections purposes.
Figure 3B:
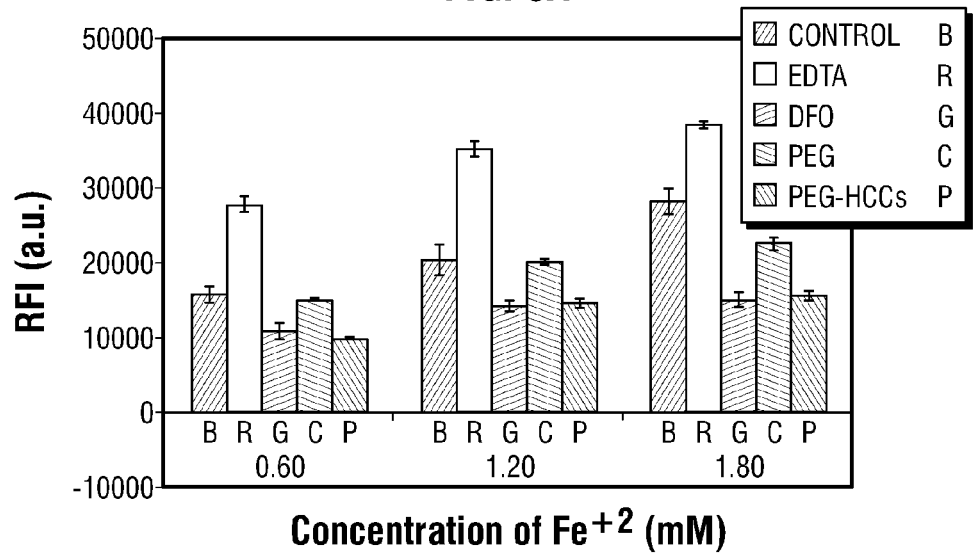
FIG. 3B shows benzoate hydroxylation induced by $Fe^{+2}$ in the presence of ethylenediaminetetraacetic acid (EDTA), 1,8-Diazafluoren-9-one (DFO), PEG-HCCs and PEG. PEG-HCCs and DFO inhibit the hydroxylation process at a similar level. In fact, PEG also prevents the hydroxylation at the highest concentration of the iron.
Figure 3C:
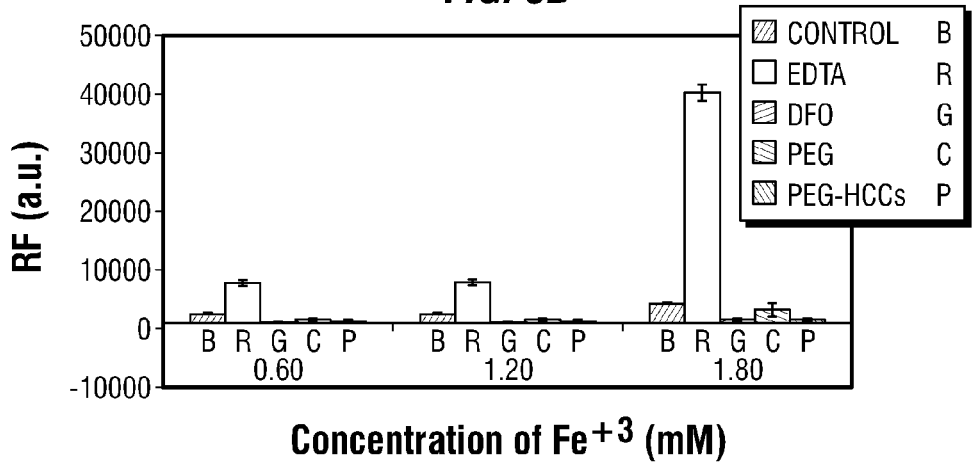
FIG. 3C shows benzoate hydroxylation induced by $Fe^{+3}$. Again, PEG-HCCs and DFO inhibit the hydroxylation process at a similar level. PEG-HCCs do not induce the Fenton reaction. The concentrations used were 0.60 mM for EDTA and DFO and 0.02 mg/mL for PEG-HCCs and 0.02 mg/mL for PEG.

The iron chelating assay was used to evaluate the antioxidant capacity of PEG-HCCs when it is exposed to hydroxyl radicals produced by the reaction between iron and $H_2O_2$. In this assay, Applicants monitored the oxidation of benzoate to salicylate by hydroxyl radicals produced by the Fenton reaction. To ensure that this measurement would be robust, sodium salicylate (SA) was mixed with PEG or PEG-HCCs every time that the experiment was run, in order to estimate how the fluorescence intensity was affected by the nanomaterial or the polymer, and then Applicants proceeded to correct it. See FIG. 3A. In general, it was observed that PEG-HCCs quench about ~20% of the fluorescence and the PEG can enhance the fluorescence up to ~10%. In the actual assay, EDTA and DFO were included as positive and negative controls, respectively. PEG-HCCs decreased the hydroxylation process as well as DFO in comparison to the case in which no chelating agent was added for both iron systems. See FIG. 3B. Both PEG-HCCs and PEG reduced the hydroxylation of benzoic acid when the highest concentration of $Fe^{+2}$ was used. Without being bound by theory, Applicants envision that this could be due to the radical scavenger capacity of the carbon core in the PEG-HCCs (FIG. 1B), the degradation of the polymer chains as previously reported (Proc. Nat. Acad. Sci. USA, 1998 (95): 10373-10377), or both. Applicants also observed that the Iron/PEG-HCCs systems do not induce the Fenton reaction.

Ascorbic Acid Assay

Figure 4A:
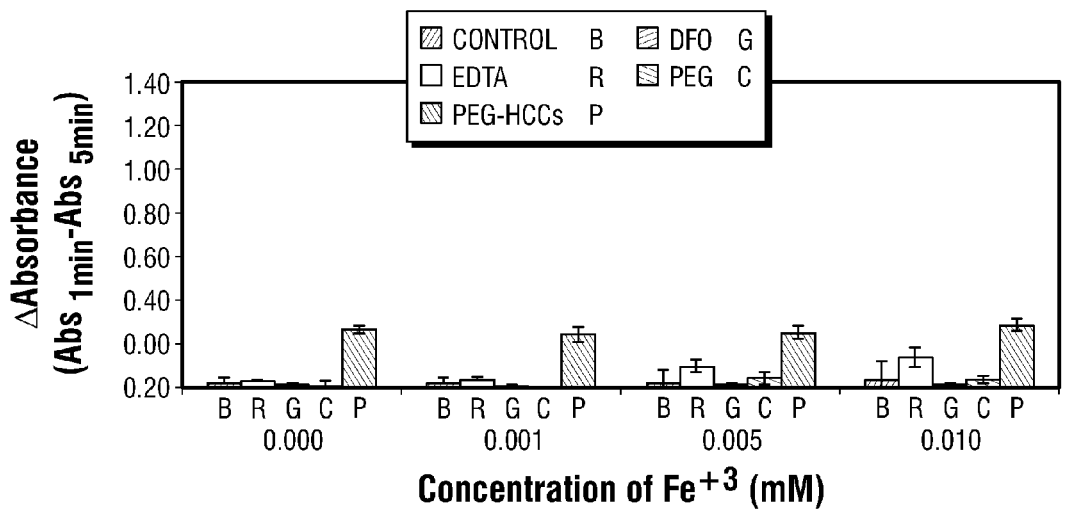
FIG. 4 shows the oxidation of ascorbic acid after 5 and 30 min of metal addition in the presence of various compounds, as measured by absorbance. Trace metal was likely present in the buffer as there were different absorbance values for EDTA and DFO compared to no chelator when no extra iron was added. Overall, these results show that PEG-HCCs in the presence of a reductant such as ascorbate function as potent oxidants, regardless of the presence or absence of $Fe^{3+}$.
Figure 4B:
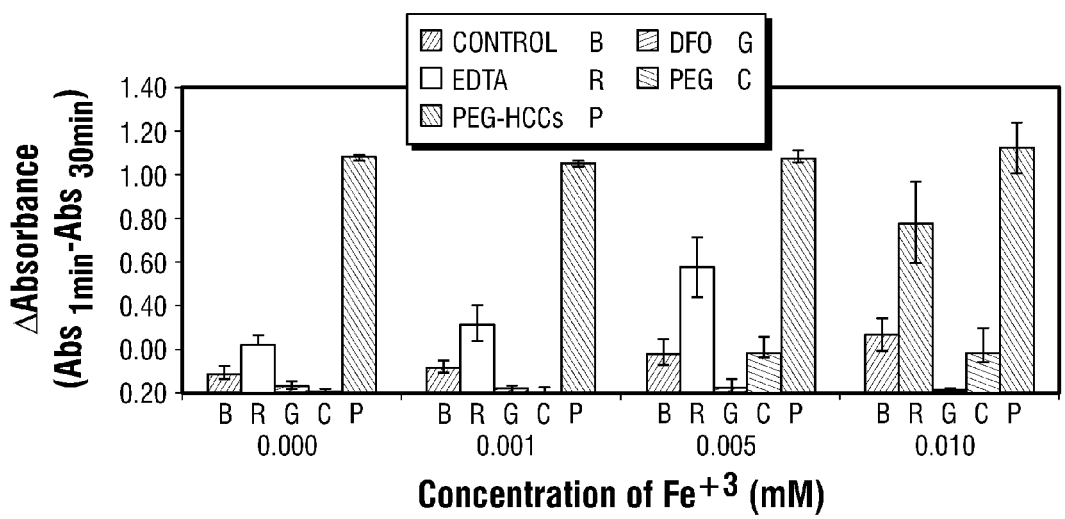

Ascorbic acid is able to serve as a donor antioxidant in free radical-mediated oxidative processes. But it is also able to reduce redox-active metals such as copper and iron, thereby increasing the oxidant properties of those metals. In general, at low concentrations, ascorbic acid is prone to be a pro-oxidant and at high concentrations serves as an antioxidant. In this assay, the oxidation of ascorbic acid by $Fe^{3+}$ is monitored in the presence or absence of various substances. EDTA again enhanced the oxidative activity of the $Fe^{+3}$ while DFO inhibited it. See FIG. 4.

Applicants also tested PEG-HCCs in this system to determine if their antioxidant capacity could be due to interactions with trace iron content, and if there is such an interaction, the oxidation of the ascorbic acid should be inhibited. Applicants found that in this system, PEG-HCCs function as potent oxidants, regardless of the presence or absence of $Fe^{3+}$. See FIG. 4. PEG-HCCs and ascorbic acid show similar pro-oxidant and antioxidant behavior. A difference is that for PEG-HCCs, no metal participation is required.

EXAMPLE 1D

Targeted Binding of PEG-HCCs to Brain Endothelial Cells

Next, Applicants evaluated if PEG-HCCs could be targeted to cultured brain endothelial cells, and if they could also alleviate oxidative stress in a biological system. A brain endothelial cell line was chosen because endothelial dysfunction is apparent even after mTBI. In the case of mTBI, there is minimal detectable brain injury and functional deficits unless hypotension is superimposed. bEnd.3 cells were treated with histamine, which is known to rapidly induce the expression of p-selectin. PEG-HCCs were targeted to p-selectin. In endothelial cells, p-selectin, a cell adhesion molecule, is involved in recruiting leukocytes to sites of inflammation and injury. P-selectin is rapidly expressed on endothelial cells following activation by histamine.

Figure 5:
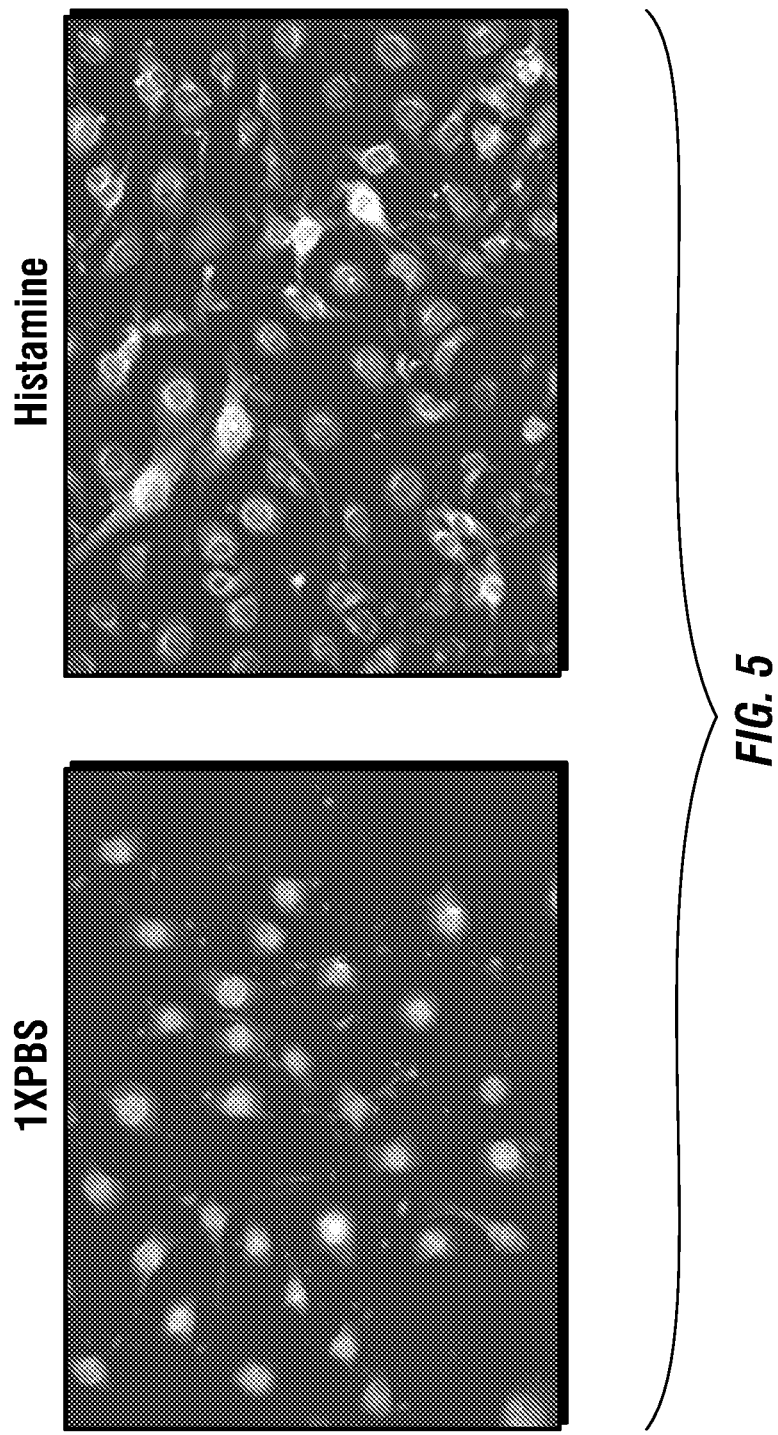
FIG. 5 shows images of b.End3 endothelial cells, indicating that they express p-selectin when stressed by histamine. Cells were treated with histamine or the diluent 1×PBS. Cells were then fixed and stained for the presence of p-selectin (green) and DAPI (blue). There was considerably enhanced binding of p-selectin antibody following histamine treatment, confirming increased expression of p-selectin.
Figure 6:
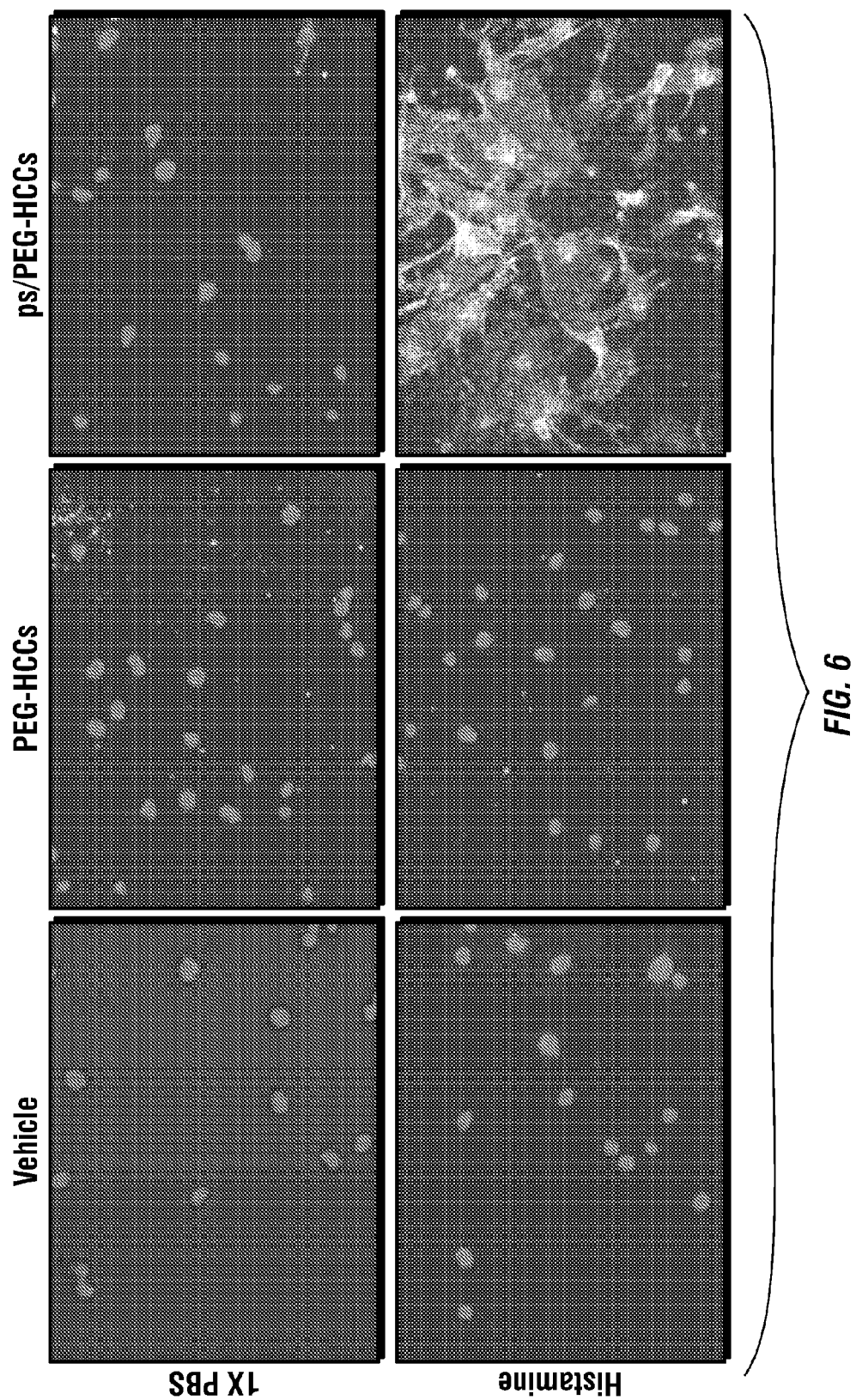
FIG. 6 shows images of b.End3 cells that were oxidatively stressed by treatment with histamine or 1×PBS. The cells were exposed to vehicle, PEG-HCCs or PEG-HCCs containing anti-p-selectin antibodies (ps/PEG-HCCs). The cells were then stained for the presence of PEG (green) and DAPI (blue). There is considerably enhanced binding of anti-PEG antibody following histamine treatment indicating enhanced binding of the ps/PEG-HCCs to stimulated b.End3 cells.

In this experiment, Applicants treated cells with histamine or 1×PBS to induce p-selectin expression. See FIG. 5. After 15 min, the cells were treated with 1×PBS, PEG-HCCs, or PEG-HCCs associated with anti-p-selectin antibodies (ps/PEG-HCCs). The cells were incubated for another 15 min and after washing and fixing, they were stained with fluorescent antibodies for the presence of PEG to detect PEG-HCCs using an anti-PEG antibody (green), anti-p-selectin antibody(red) to detect p-selectin, and DAPI (nuclear stain; blue). In the cells that are not stimulated by histamine, there is little binding apparent with the p-selectin targeted PEG-HCCs. However, there was a dramatic increase in the binding of ps/PEG-HCCs to cells after stimulation by histamine. See FIG. 6, bottom panel. This experiment demonstrates enhanced binding of the targeted PEG-HCCs to endothelial cells in a model that induces expression of a protein, p-selectin.

Figure 7:
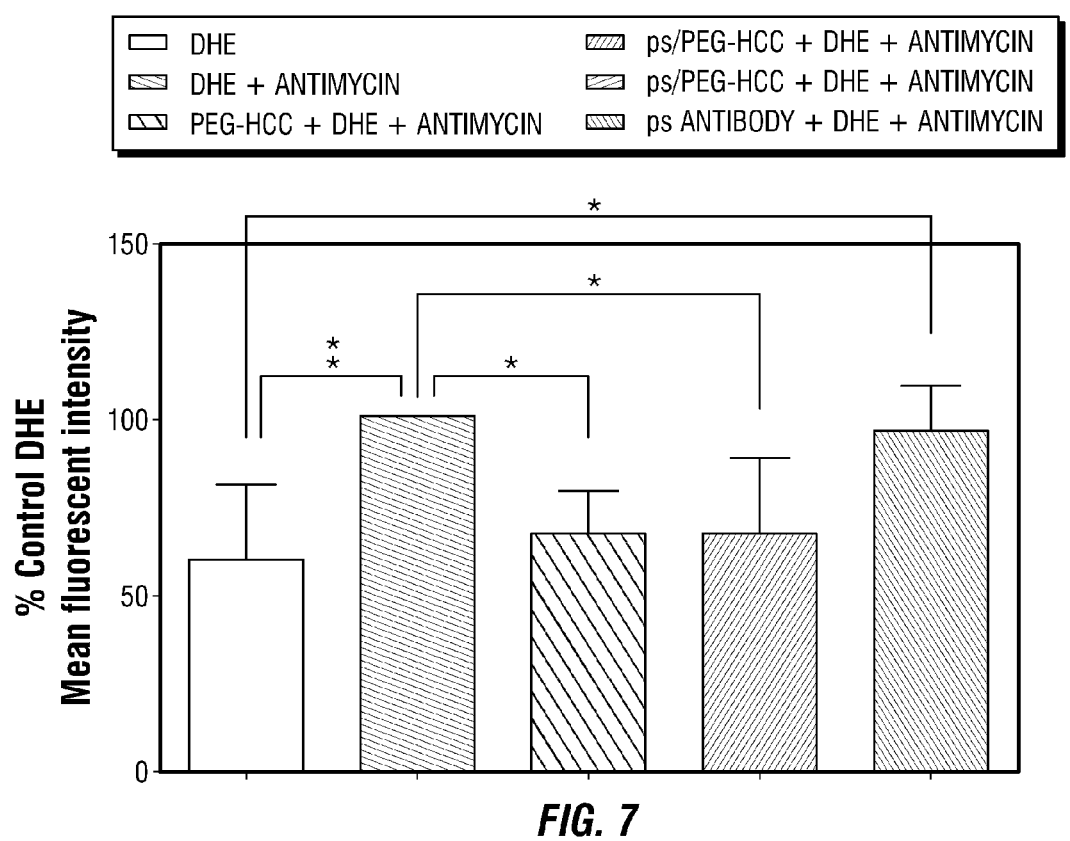
FIG. 7 shows that PEG-HCCs and targeted ps/PEG-HCCs effectively reduce intracellular oxidative stress in b.End3 endothelial cells. Antimycin A (Ant A) was used to induce intracellular superoxide production. Dihydroergotamine (DHE) mean fluorescence intensity (indicative of oxidative stress) was measured in cells treated with AntA (mean of 5 separate experiments). Results are given as % control (DHE+AntA, black bar) to account for minor differences in DHE concentrations and laser fluctuations. Untargeted (solid grey) PEG-HCCs and targeted ps/PEG-HCCs (striped grey) were effective at reducing DHE fluorescence after AntA treatment, while treatment with a similar amount of p-selectin antibody in the absence of PEG-HCCs (striped white) was not effective.

Applicants also evaluated whether applying the targeted p-selectin antibody to the PEG-HCC would reduce its antioxidant ability. Applicants tested the protective capacity of the nanoparticles by stressing the cells with AntA and determining the effectiveness of the native or antibody bound PEG-HCCs at reducing levels of oxidative radicals. The level of oxidative stress was measured by DHE fluorescence. An increase in fluorescence is proportional to oxidative stress and is roughly proportional to superoxide levels, although not specific under all conditions. In this study, Applicants replicated the ability of the PEG-HCCs to reduce DHE fluorescence, even when applied after the AntA, and found that ps/PEG-HCCs reduced the level of DHE fluorescence to comparable levels as non-antibody bound PEG-HCCs, and to background (DHE). See FIG. 7. By comparison, p-selectin antibody by itself had no significant effect on DHE fluorescence.

Remarks

The results in Example 1 indicate that PEG-HCCs possess biologically relevant antioxidant capacity. Furthermore, the results indicate that the mechanism may not involve chelation. PEG-HCCs were effective in vitro following administration of a mitochondrial toxin that induces oxidative stress. PEG-HCCs could also be readily targeted to oxidatively stressed brain endothelial cells. When functionalized for targeting, PEG-HCCs retained the ability to alleviate oxidative stress in cultured brain endothelial cells. Overall, these results suggest that targeted PEG-HCCs are potential therapeutics for the cerebrovascular dysfunction from mTBI, and the results open additional possibilities for targeting a variety of pathological processes.

Because of the deleterious effects of loss of cerebrovascular responsiveness, even in mild injuries, a therapy that mitigates oxidative injury to endothelial cells should hold promise for the improvement of outcome following mTBI. Furthermore, because there is a major burst of superoxide radical at the time of resuscitation following TBI and hemorrhagic hypotension; treatment at the time of resuscitation may provide a clinically realistic time point that can address at least one pathological event in the care of the TBI patient.

In addition, targeting the PEG-HCC using a p-selectin antibody demonstrated a more rapid binding to stressed b.End3 cells. This characteristic may have advantages as a therapeutic agent with enhanced binding to molecules expressed at the site of injury. There are many potential such targets, but p-selectin appears particularly promising as there is some added therapeutic benefit in experimental TBI of the antibody itself, potentially in addition to the antioxidant ability of the PEG-HCCs.

EXAMPLE 2

Use of PEG-HCCs to Treat Oxidative Stress Associated with TBI

Example 2 provides additional support that PEG-HCCs can be used to treat oxidative stress associated with TBI. Specifically, Example 2 provides data indicating that PEG-HCCs can be used to improve cerebrovascular dysfunction following TBI. Applicants demonstrate in this Example that PEG-HCCs are effective antioxidants in cell culture and rapidly restore cerebral blood flow (CBF) in a traumatic brain injury/hypotension/resuscitation rat model when administered during resuscitation.

Injury to the neurovasculature is a feature of brain injury and must be addressed to maximize opportunity for improvement. Cerebrovascular dysfunction, manifested by reduction in cerebral blood flow (CBF), is a key factor that worsens outcome after traumatic brain injury (TBI), most notably under conditions of hypotension. Applicants report here that PEG-HCCs rapidly restore CBF in a mild TBI/hypotension/resuscitation rat model when administered during resuscitation—a clinically relevant time point. Along with restoration of CBF, there is a concomitant normalization of superoxide and nitric oxide levels. Given the role of poor CBF in determining outcome, this finding is of major importance for improving patient health under clinically relevant conditions during resuscitative care. In addition, the findings have direct implications for the current TBI/hypotension war-fighter victims in the Afghanistan and Middle East theaters. The results also have relevancy in other related acute circumstances such as stroke and organ transplantation.

Injury to the neurovascular unit is recognized as a major determinant of patient outcome, and it has been hypothesized that therapies that do not address that injury are unlikely to promote recovery. In the case of traumatic brain injury (TBI), damage to the neurovascular unit is manifested under conditions of abnormally low blood pressure, known as hypotension, by loss of cerebral autoregulation and poor reperfusion upon resuscitation. These events contribute to the clinical finding that hypotension, even in mild TBI, predicts poor outcome.

Elevated levels of reactive oxygen species (ROS), such as superoxide (SO), are found in the vasculature and have been shown to mediate loss of autoregulatory tone. Along with spikes of ROS following trauma, continued damaging spikes in the level of ROS are observed upon subsequent blood reinfusion during resuscitation. Hence, in an effort to stabilize the patient, furtherance of oxidative damage ensues. However, blood reinfusion also provides an opportunity to intervene at a clinically realistic time point. In this report, Applicants demonstrate that PEG-HCCs, which are nontoxic carbon particles, rapidly restore cerebral blood flow (CBF) in a TBI/hypotension/resuscitation rat model when administered during resuscitation. Along with restoration of CBF, there is a concomitant normalization of both SO and the vasodilator, nitric oxide (NO), levels.

EXAMPLE 2A

Effects of PEG-HCCs on b.End3 Cells

Figure 12A:
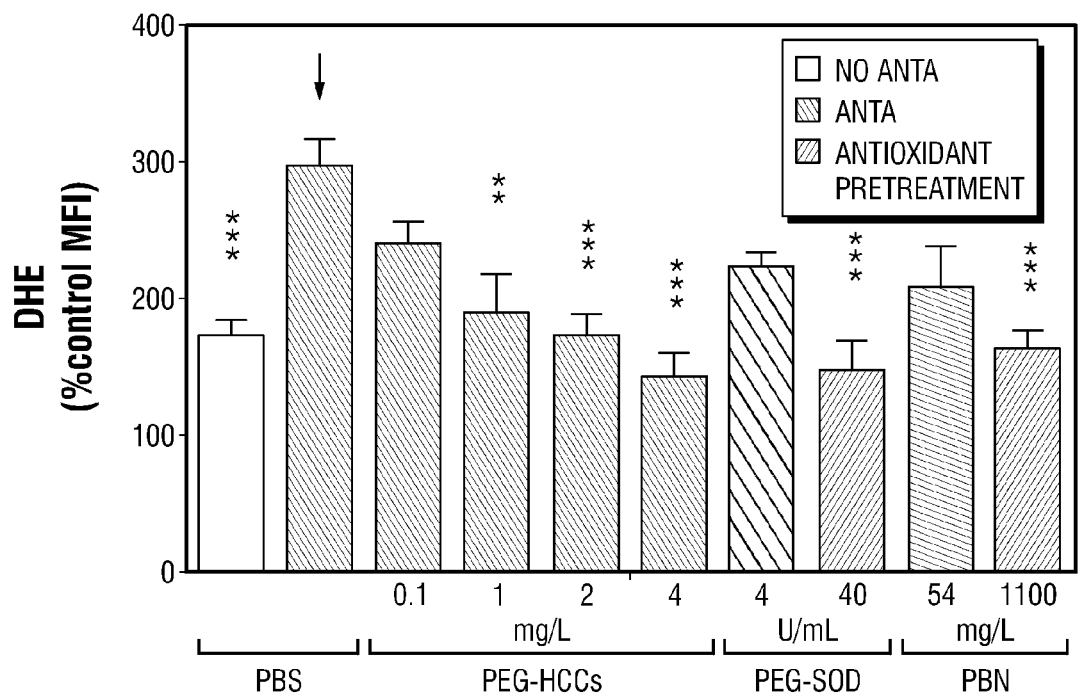
FIG. 12A shows intracellular radical oxygen species (ROS) levels for b.End3 cells as determined by dihydroethidium (DHE) staining and flow cytometry. The mean fluorescent intensity (MFI) of 10,000 cells/group was normalized to the group not treated with antimycin A (AntA in graphs) or DHE. Phosphate buffered saline (PBS, black bar) or antioxidant treatments (blue, green, and red solid bars) were given after antimycin A. Some antioxidants were administered prior to antimycin A (striped bars).
Figure 12B:
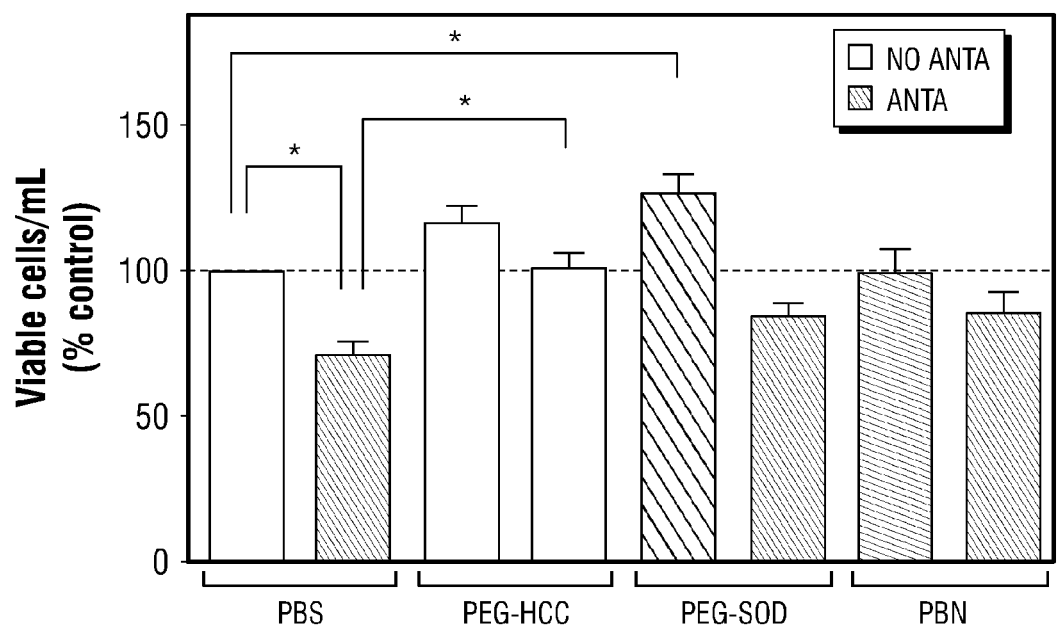
FIG. 12B shows cell survival relative to control for b.End3 cells given different treatments. The cells were either cultured in the presence of PEG-HCCs, PEG-SODs or PBN alone (solid bars), or the cells were first treated with a dose of antimycin A titrated to kill 30% of the cells followed by treatment with PEG-HCCs, PEG-SOD or PBN (striped bars). Results are a mean of seven separate experiments. Error bars are s.e.m. ANOVA with Bonferroni post test was used to calculate statistics. *p-value<0.05.

By confocal microscopy studies, Applicants confirmed that PEG-HCCs are rapidly internalized by b.End3 cells. See FIGS. 10-11. Next, a series of in vitro studies showed that when oxidative stress was induced in b.End.3 cells by treatment with the mitochondrial toxin, antimycin A, the intracellular oxidative stress could be reduced in a dose-dependent manner by treatment with PEG-HCCs. See FIG. 12. The amount of oxidative radical expression was measured as a proportion of DHE fluorescence. PEG-HCC treatment was effective even 10 min after toxin exposure, while neither PEG-SOD nor PBN was effective in the post-toxin-treated cells. The latter two traditional antioxidants were only effective pre-toxin exposure, and then only at a 10 to 30× higher dose. See FIG. 12A. Furthermore, at higher doses of antimycin A where significant cell death could be induced, post-treatment with PEG-HCCs was able to restore cell viability to more than 65% of baseline. However, no protective effect from post-treatment with either PEG-SOD or PBN could be observed. See FIG. 12B.

Figure 13A:
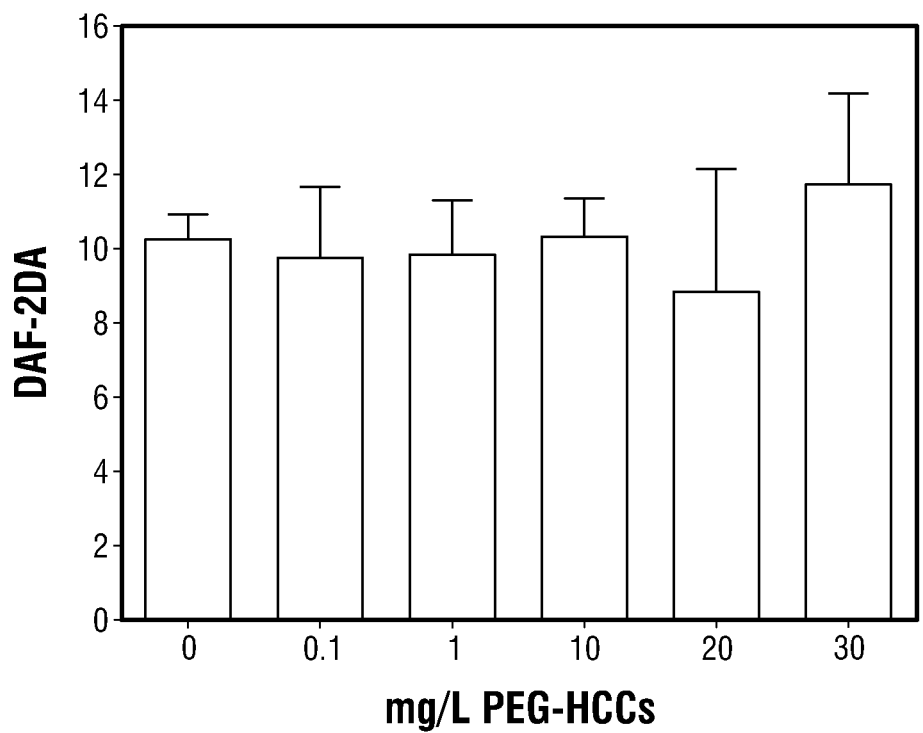
FIG. 13A shows that concentrations of PEG-HCCs up to 30 mg/L did not quench NO dye fluorescence (p>0.05 for all comparisons).
Figure 13B:
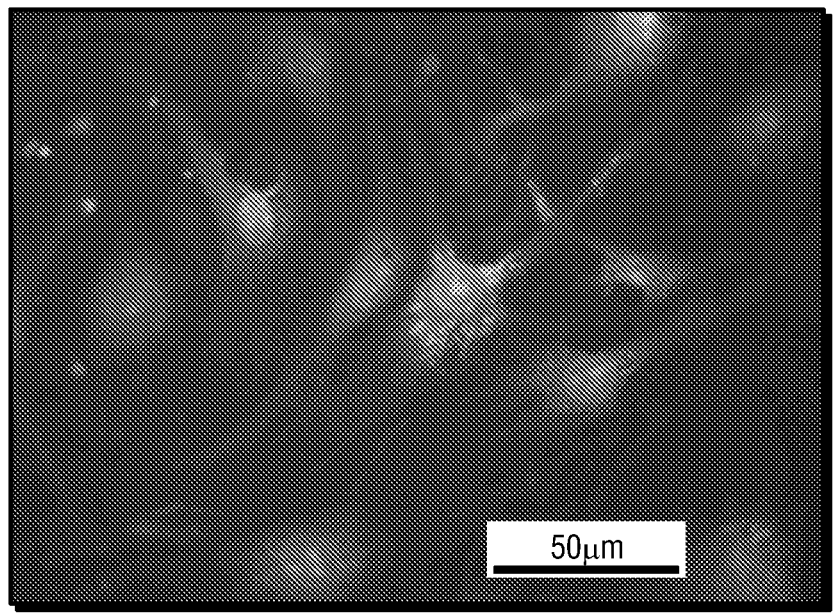
FIG. 13B shows a fluorescent microscope image of bEnd.3 cells treated with DAF-2DA. Error bars are s.e.m. Scale bar is 50 µm.
Figure 14:
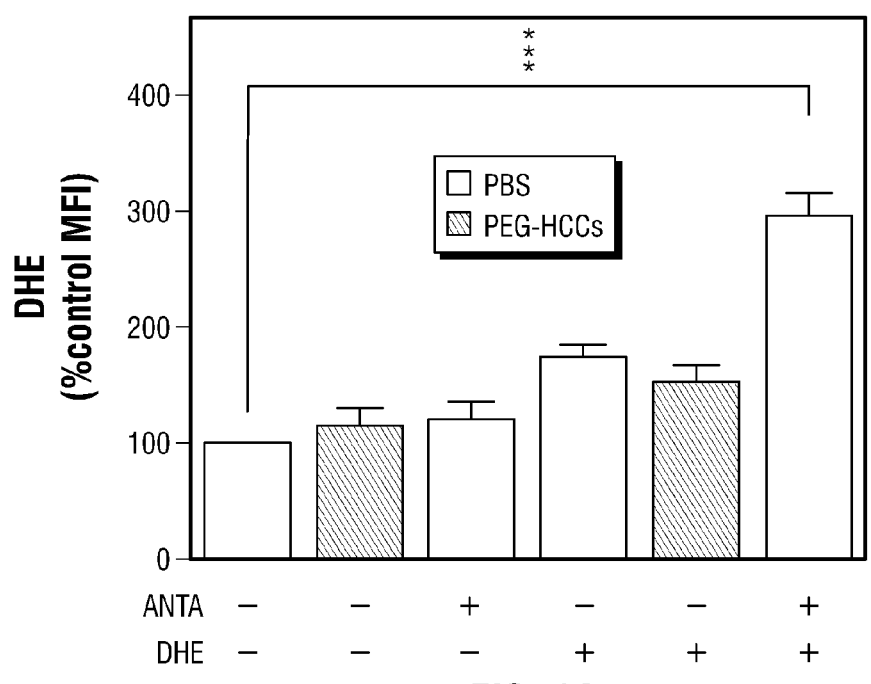
FIG. 14 shows controls for intracellular superoxide (SO) assay to determine whether there is direct interference between the PEG-HCCs and the fluorescent assay. Cells were treated with or without antimycin A (a mitochondrial toxin that induces SO production). PEG-HCCs were added 15 min later (grey bars) followed by DHE (SO-specific dye), as indicated by +. There was no reduction in either non-specific fluorescence (first three bars) or background fluorescence after addition of DHE (bars 4 and 5). In the last combination (bar 6), DHE and antimycin A-treated cells demonstrated, as expected, a significantly higher DHE staining compared to the untreated control (first bar).

These studies demonstrate the efficacy of the PEG-HCCs to eliminate ROS that would otherwise have resulted in cell death. Additional in vitro control experiments in bEnd.3 cells indicated that the PEG-HCCs do not quench NO sensitive fluorescence of DAF-2 associated with spontaneous NO release from these cells. See FIGS. 13-14.

EXAMPLE 2B

In Vivo Effects of PEG-HCCs

Figure 15A:
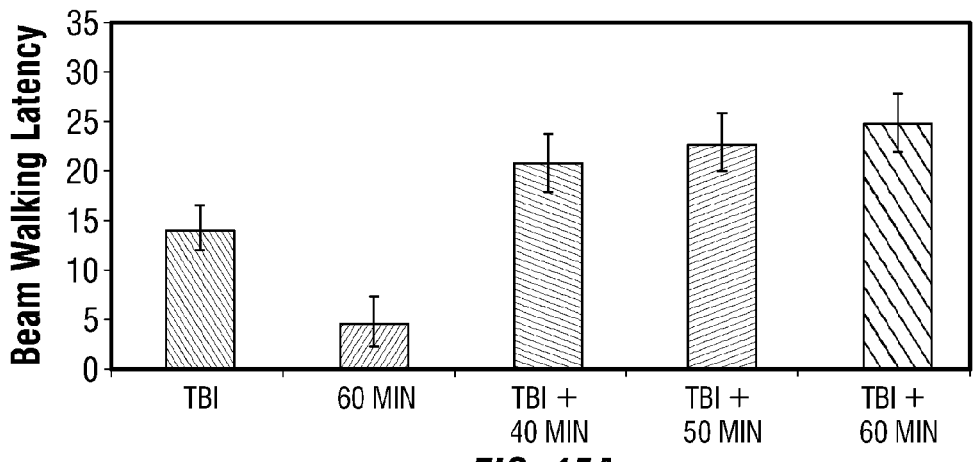
FIGS. 15A-B provide data indicating a large change in lesion volume (noted with yellow arrows in A) if TBI is associated with hypotension for 40, 50 and 60 min (as recorded 14 days post TBI/hypotension).
Figure 15B:
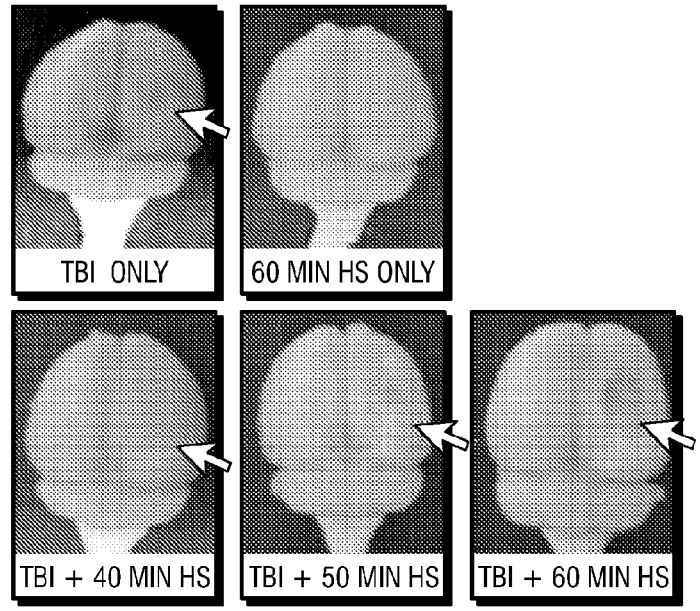
Figure 15C:
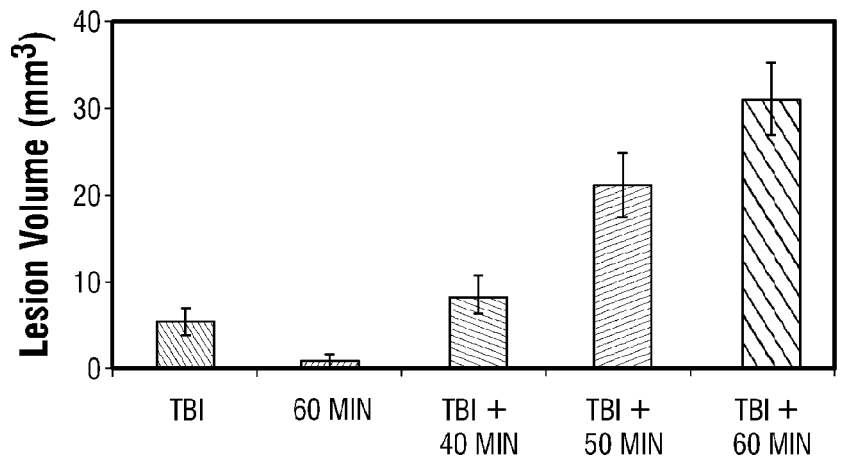
FIG. 15C provide data indicating a decline of behavioral abilities tracks with increased duration of hypotension. (This data was obtained from Claudia Robertson, Md., Baylor College of Medicine).

PEG-HCCs were next evaluated in vivo. The TBI model used in this Example aimed to mimic the common clinical situation in which TBI is accompanied by a systemic injury resulting in hypotension. There is minimal evidence of either behavioral or histological injury with either TBI or hypotension alone, but with the superimposition of hemorrhagic hypotension and subsequent resuscitation, there is marked expansion of lesion size and behavioral impairment. See FIG. 15. Reperfusion CBF was reduced in proportion to the increase in injury, supporting the hypothesis that this is primarily a vasculature injury. The loss of autoregulation and poor reperfusion originating in the brain endothelium contribute to injury, even in the setting of mild TBI. This highlights that while the blood-brain barrier becomes compromised following mild TBI, thereby allowing access of agents such as PEG-HCCs to the brain itself, the major treatable injury in the TBI and secondary injury paradigm is to the brain endothelium.

Using the above-mentioned TBI/hypotension/resuscitation rat model, treatment followed the field situation as follows. 50 min after the injury and loss of blood, phosphate buffered saline (PBS) was administered in an ambulance "prehospital" phase. Next, after further delay of 30 min, definitive "hospital" care consisted of therapy administration, oxygenation and blood infusion. The model is outlined in Table 4 and described below.

TABLE 4

Rat Injury Model for Testing the Effects of PEG-HCCs

| Phase 1 Injury and hemorrhage (50 min) | Phase 2 Prehospital-ambulance (30 min) | Phase 3 Definitive-hospital (30 min) | Phase 4 Test outcome (6 h) |
|---|---|---|---|
| Ventilate (air) Mild TBI Withdraw blood to MAP 40 mm Hg | Ventilate (air) Initial resuscitation-saline MAP ≥ 50 mm Hg | Give drug Ventilate with 100% oxygen Reinfuse blood Saline to MAP ≥ 60 mmHg | 0-6 h Monitor cerebral hemodynamics 6 h Determine SO and NO levels |

In Phase 1, Long Evans rats (250 to 300 g) underwent sham injury or mild cortical compression injury TBI (3 m/s, 2.5 mm deformation, Table 5) plus hemorrhagic hypotension produced by controlled blood withdrawal to reach a mean arterial blood pressure (MAP) of 40 mm Hg. This occurred in a decelerating protocol to mimic trauma blood loss.

TABLE 5

TBI impact characteristics and rat weights
Statistics (repeated measures ANOVA)

| | | Vehicle | PEG-HCCs | p-value |
|---|---|---|---|---|
| Rat weight (grams) Mean ± SD | | 287.1 ± 27.0 | 279.0 ± 16.0 | 0.3955 |
| Impact characteristics | | | | |
| Velocity | m/s | 3.29 ± 0.41 | 3.25 ± 0.49 | 0.8388 |
| Duration | ms | 79.0 ± 8.9 | 80.8 ± 5.7 | 0.5733 |

In order to simulate field resuscitation and ambulance transport (Phase 2), the rats received an i.v. of Lactated Ringer's solution for initial resuscitation. Next, hospital care (Phase 3) was simulated by administering a single dose of PEG-HCCs (2 mg/kg) or a diluent vehicle, phosphate buffered saline (PBS), via a 5 min i.v. tail vein administration. This was followed by oxygenation and blood reinfusion. Beginning with Phase 1, there was extensive physiological monitoring included MAP, arterial blood gases, intracranial pressure and non-invasive spatial brain perfusion using laser Doppler flowmetry (LDF, Periscan).

Figure 16A:
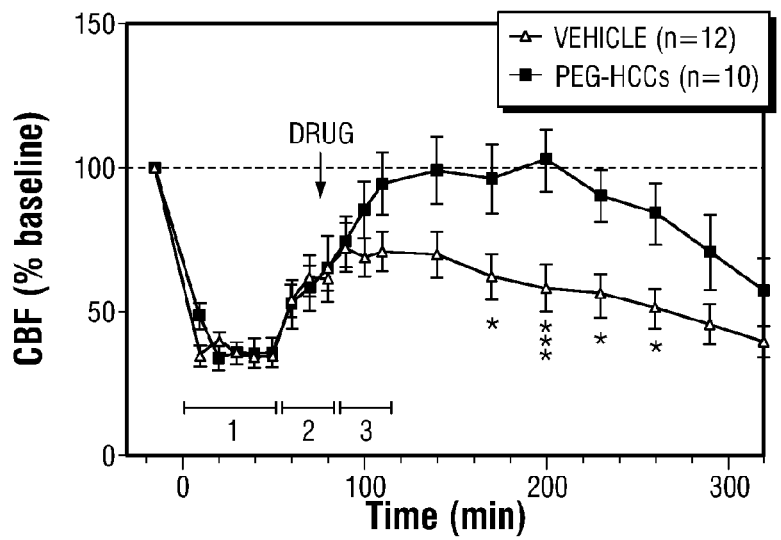
FIG. 16 shows data indicating that PEG-HCC treatment improves cerebral blood flow (CBF) in the injured cortex in rats with TBI plus hypotension. The data show CBF in the injured cortex (FIG. 16A), the peri-lesional cortex (FIG. 16B), and the contralateral cortex (FIG. 16C). Drugs (PEG-HCC or PBS vehicle) were given where indicated. Time 0 min indicates when the TBI was performed. The different phases are indicated as follows: Phase 1=TBI+hypotension; Phase 2=saline during "prehospital-ambulance phase"; Phase 3=blood reinfusion during "definitive-hospital phase". Error bars are s.e.m.
Figure 16B:
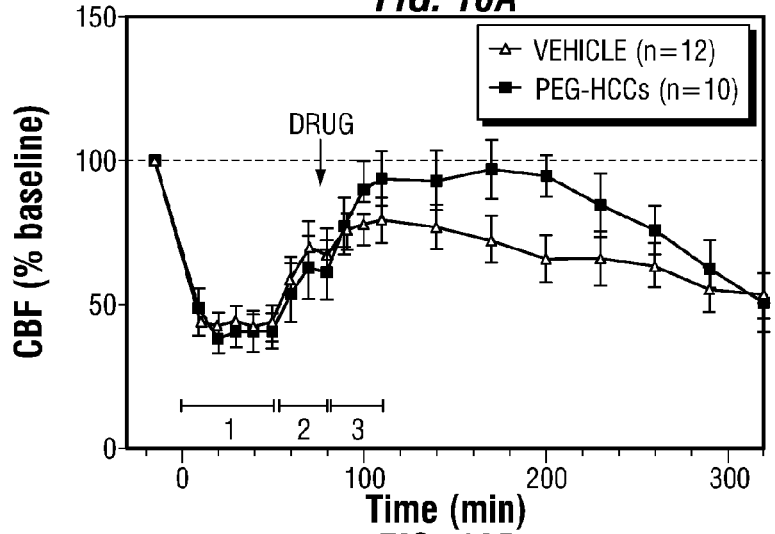
Figure 16C:
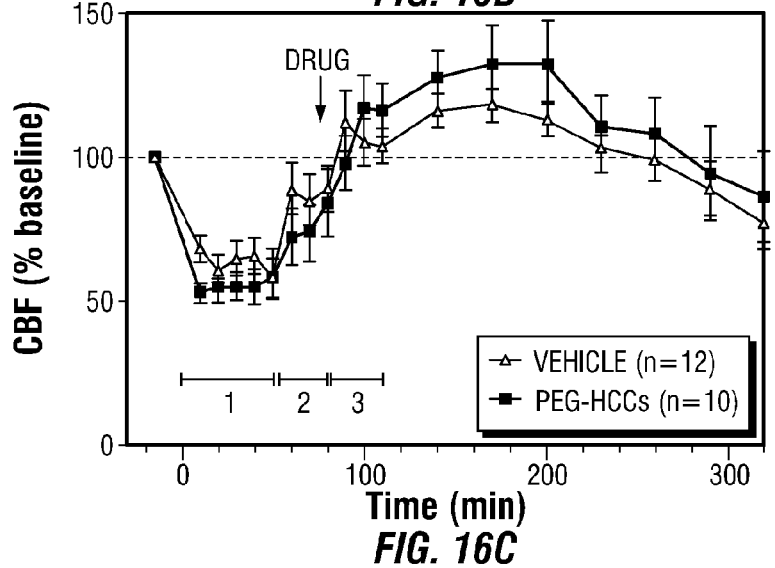

As illustrated in FIG. 16, PEG-HCCs restored cerebral perfusion and normalized the oxidative radical profile. Rats received a single dose of PEG-HCCs (2 mg/kg) or PBS at the beginning of the blood resuscitation (Phase 3). CBF was measured for 6 h from the cortical surface with LDF (Phases 3 and 4). Just before the 6 h mark, rats were injected with dyes for SO (dihydroethidium, DHE) and NO (diaminofluorescein diacetate, DAF-2DA) detection, and perfusion fixed. Systemic injection of these dyes and a short circulation time was able to identify vascular expression of these radicals. LDF-relative CBF (rCBF) is shown in the series of FIGS. 16A-C.

FIG. 16A illustrates changes in rCBF in the region of the traumatic injury. Hypotension following TBI significantly reduced rCBF. In the vehicle-treated TBI group, rCBF was only partially restored by reinfusion of shed blood while rCBF returned rapidly to baseline levels following administration of the PEG-HCCs and blood. The duration of the PEG-HCC effect was from 2 h to 3 h, at which time both groups showed a decline in rCBF. This duration of treatment effect is consistent with the 2 h to 3 h blood half-life of PEG-HCCs and also consistent with the prolonged anesthesia time.

Figure 17:
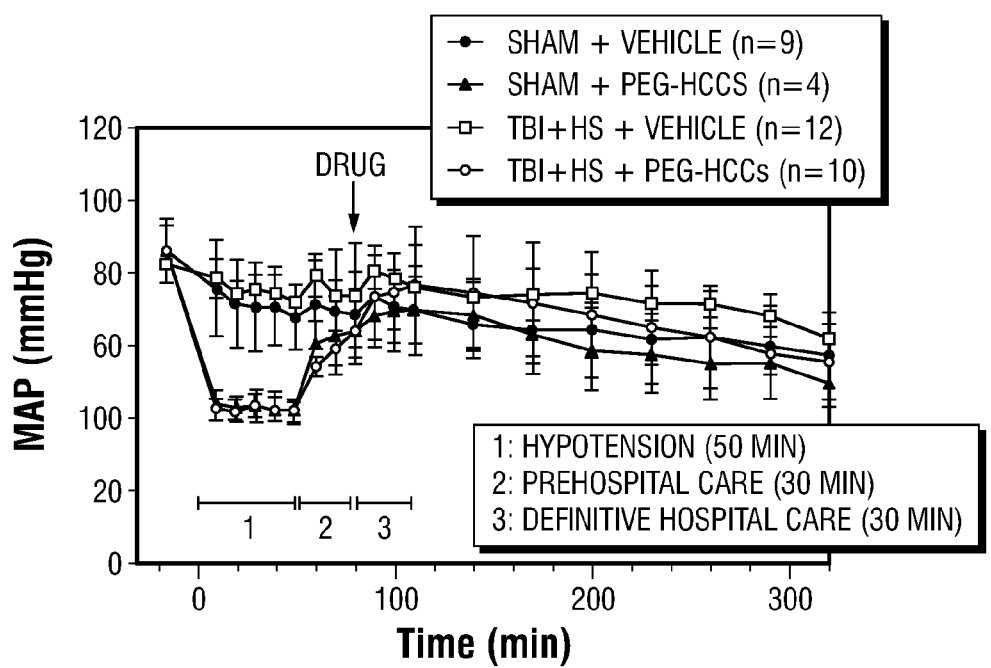
FIG. 17 shows mean arterial pressure (MAP) for rats undergoing sham surgery or TBI and hemorrhagic shock (TBI+HS). Drugs (PEG-HCC or PBS vehicle) were given where indicated. Time 0 min indicates when the TBI was performed. The different phases are indicated as follows: Phase 1=TBI+hypotension; Phase 2=PBS during "pre-hospital-ambulance phase"; and Phase 3=blood reinfusion during "definitive-hospital phase." No statistical differences (p-value>0.05) were seen with data calculated with repeated measures.
Figure 18A:
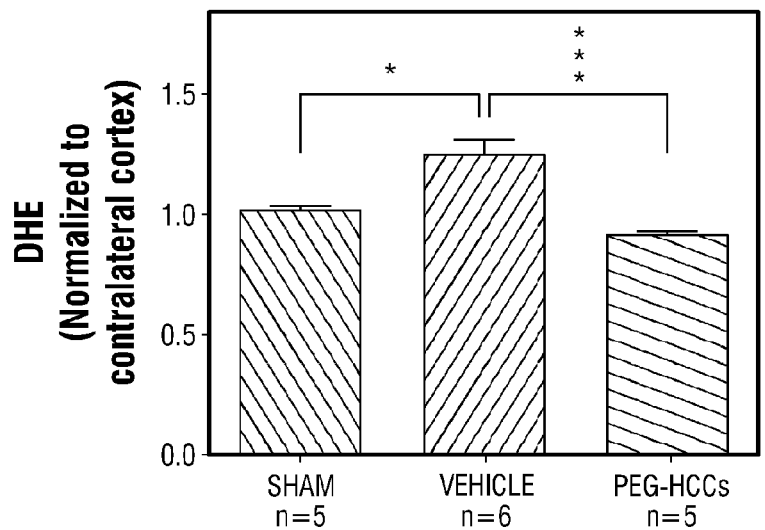
FIG. 18 shows the levels of superoxide (SO) and nitric oxide (NO) recorded in the brain and vasculature. DHE levels (proportional to SO and oxidative radicals) in the brain (cortex) (FIG. 18A) and blood vessels (FIG. 18B) of sham surgery rats or rats with TBI+hypotension with vehicle or PEG-HCC treatment are shown. The vehicle-treated and sham groups were controls. The ipsilateral cortex (region with TBI) was normalized to the contralateral cortex. PEG-HCC treatment (blue) was able to reduce DHE staining compared to vehicle treatment (red), with a larger magnitude of effect seen in the blood vessels, which is likely the site of cerebrovascular dysfunction evident in the TBI model.
FIG. 18C shows microscopy of DHE staining (red) in the injured cortex (scale bar=200 μm). Similarly, DAF-2DA levels (indicative of NO levels) are shown in brain (cortex) (FIG. 18D) and blood vessels (FIG. 18E) of sham surgery rats or rats with TBI+hypotension with vehicle or PEG-HCCs treatment. Microscopy of DAF-2DA staining (green) in the injured cortex is shown in FIG. 18F. Scale bar=200 μm.
Figure 18B:
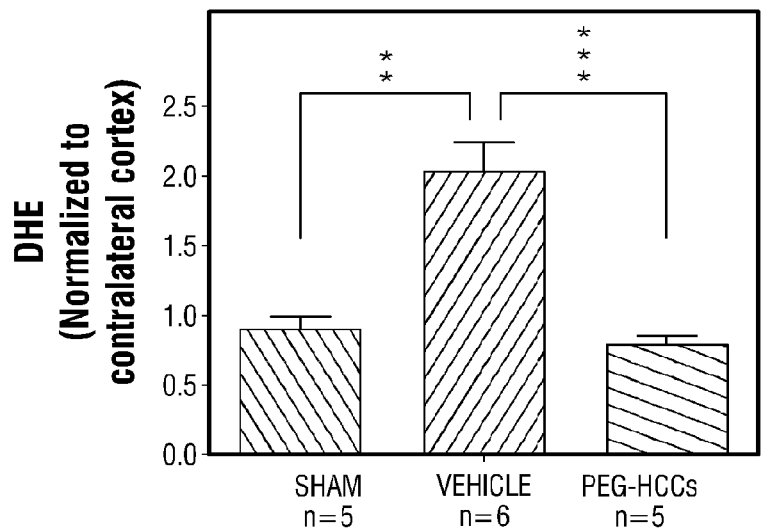
Figure 18C:
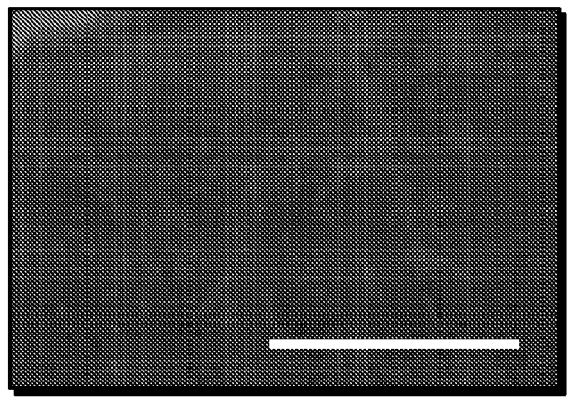
Figure 18D:
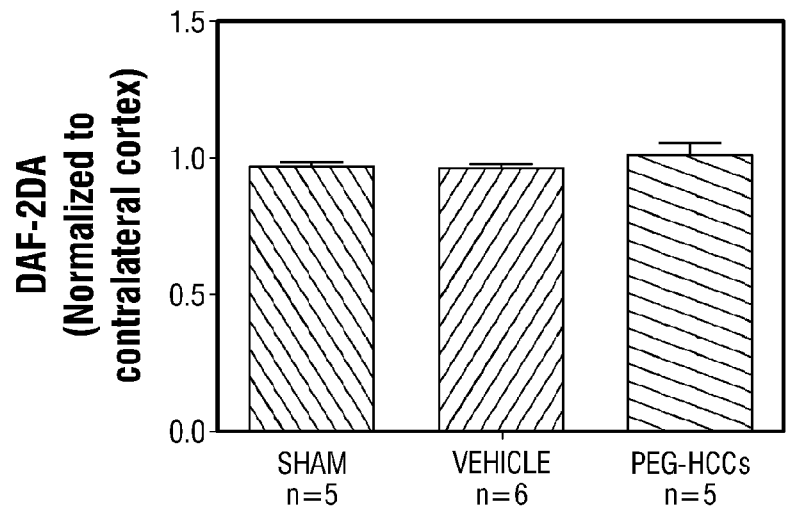
Figure 18E:
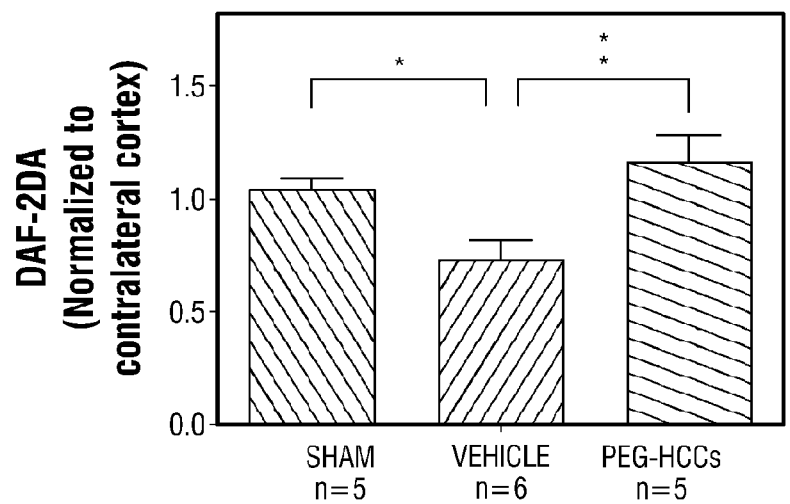
Figure 18F:
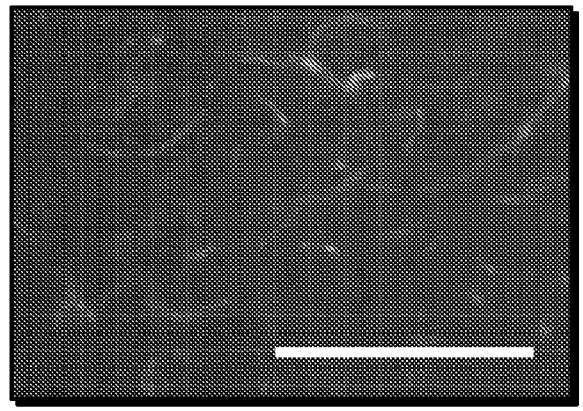

FIG. 16B shows a qualitatively similar effect in the peri-traumatic region, with rCBF returning to baseline in the PEG-HCC-treated group, while remaining depressed in the vehicle-treated group. No effect on rCBF of either group in the contralateral cortex (FIG. 16C) indicates that the outcomes seen in the lesion and peri-lesional regions were not artifactual. Additional experiments in a model to simulate linear flow show that there was no effect of PEG-HCCs on the LDF signal used to measure CBF, nor did the PEG-HCCs influence systemic blood pressure or physiological variables. See FIG. 17 and Table 6.

TABLE 6

Arterial blood gases in the TBI and hypotension model at baseline, end of hypotension and during the hospital phase.

| Arterial blood gases (mean ± SD) | | Vehicle | PEG-HCCs | p-value |
|---|---|---|---|---|
| Baseline | pH | 7.44 ± 0.06 | 7.45 ± 0.07 | 0.775 |
| | pCO$_2$ | 41.46 ± 4.07 | 39.08 ± 7.4 | 0.8425 |
| | pO$_2$ | 300.9 ± 80.7 | 309.5 ± 87.6 | 0.9144 |
| Hypotension | pH | 7.39 ± 0.01 | 7.30 ± 0.05 | |
| | pCO$_2$ | 41.85 ± 1.06 | 47.83 ± 4.99 | |
| | pO$_2$ | 139.1 ± 48.7 | 101.2 ± 36.4 | |
| Hospital | pH | 7.29 ± 0.11 | 7.40 ± 0.09 | |
| | pCO$_2$ | 41.77 ± 1.99 | 37.73 ± 9.44 | |
| | pO$_2$ | 249.9 ± 100.3 | 295.9 ± 85.7 | | pCO$_2$ is the partial pressure of CO$_2$
pO$_2$ is the partial pressure of O$_2$
Statistics: Repeated measures ANOVA These results demonstrate that in a model of TBI/hypotension/resuscitation, the PEG-HCCs rapidly restore the cerebral perfusion and that the PEG-HCCs were directly improving CBF in the injured area.

Furthermore, as shown in FIG. 18, the injection of PEG-HCCs significantly reduced vascular SO levels, underscoring that this is primarily a vasculature injury. See FIGS. 18A-C. Concomitantly, treatment with PEG-HCCs completely restored vascular NO levels. See FIGS. 18D-F. This duality of modes in the resuscitative phase of treatment, specifically decreasing SO and normalizing NO, is unpredictable in such injury models.

In summary, this Example illustrated that PEG-HCCs are non-toxic and anti-oxidative particle-based drugs that have efficacy at the neurovascular level in restoring CBF after mild TBI. The results shown for restoring CBF while normalizing SO and NO levels primarily in the cerebral vasculature are suggestive of a treatment that could vastly improve the recovery and long-term neurological prognosis for traumatized patients. Furthermore, the results indicate that PEG-HCCs could also be used for other acute disorders, such as stroke in which reperfusion-based ROS release is associated with extension and propagation of injury.

EXAMPLE 2C

Double Dosing of PEG-HCCs in Treating CBF

As set forth in the aforementioned Examples, Applicants have shown that a single dose of PEG-HCCs can improve CBF in a rat model of mTBI and hemorrhagic shock when administered 80 minutes after TBI. The length of the effect on CBF correlated well with the half life of the PEG-HCCs in the bloodstream (2-3 hours). This Example aims to determine whether a second dose of PEG-HCCs would sustain this effect.

Figure 19A:
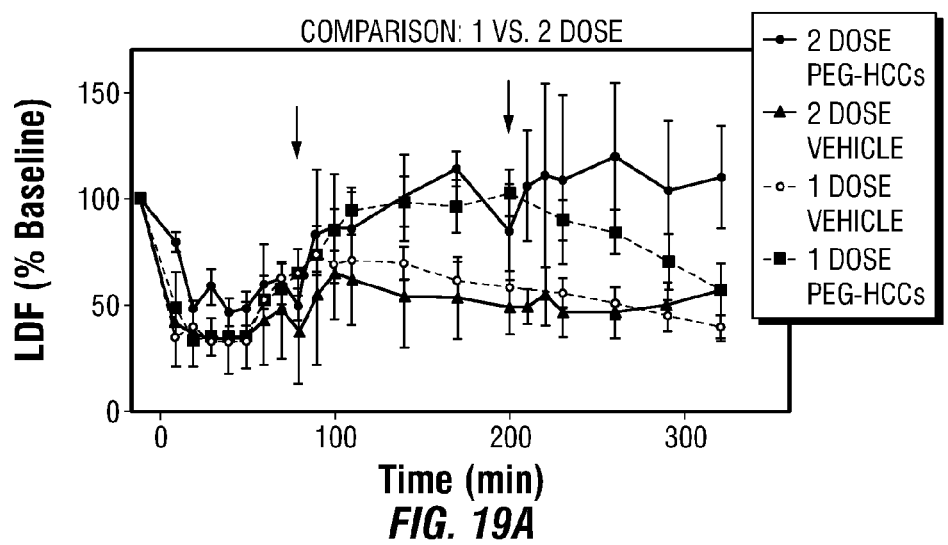
FIG. 19A shows that a second dose of PEG-HCCs (administered 2 hours from the first dose) sustains CBF in rat models.
Figure 19B:
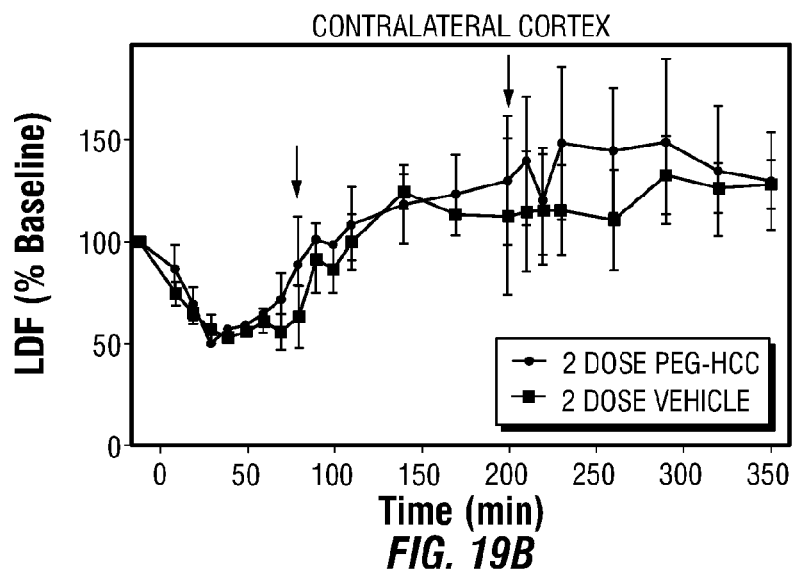
FIG. 19B shows that the relative CBF in the uninjured contralateral cortex was similar between 2 dose PEG-HCCs and vehicle-treated rats (104.1±6.9 and 93.5±5.9, respectively).
Figure 19C:
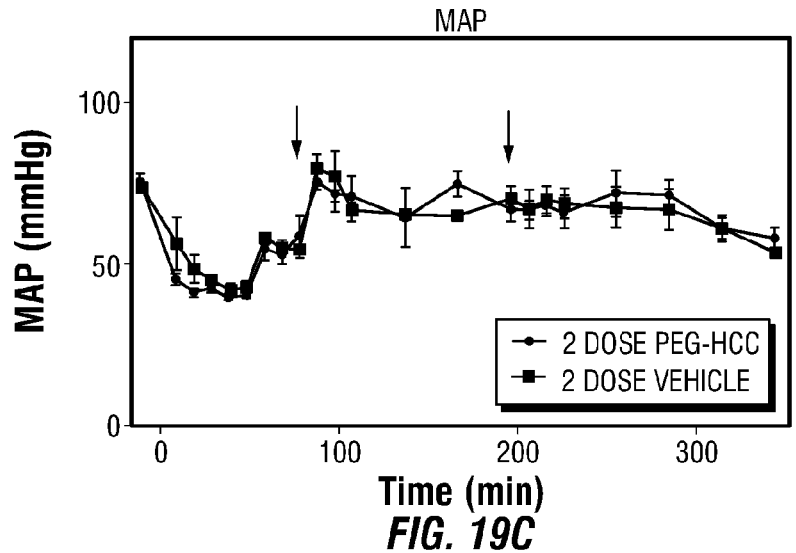
FIG. 19C shows that the mean arterial blood pressure (MAP) was not significantly different between the groups.

As summarized in FIG. 19, data comparing a single dose of PEG-HCCs and two doses of PEG-HCCs (administered 2 hours apart) indicate that a second dose of PEG-HCCs sustains CBF. Laser Doppler flowmetry (LDF) was used to measure CBF. All CBF values were normalized to the baseline CBF value for each rat (relative CBF). The relative CBF was maintained in the injured brain at the end of the monitoring period (6 h post TBI) with a second dose of PEG-HCCs (91.9±29.5 relative CBF in 2 dose compared to 57.1±11.9 relative CBF in single dose study). See FIG. 19A. Vehicle treatment (red) indicates that the animals underwent the same procedures but were given the diluent (solution the drug is suspended in) instead of drug. Arrows indicate cases when the drug (PEG-HCCs or vehicle) was administered intravenously. As illustrated in FIG. 19B, the relative CBF in the uninjured contralateral cortex was similar between 2 dose PEG-HCCs and vehicle-treated rats (104.1±6.9 and 93.5±5.9, respectively). As illustrated in FIG. 19C, the mean arterial blood pressure (MAP) was not significantly different between groups (p=0.507, RM ANOVA with Bonferroni post test).

EXAMPLE 2D

Materials and Methods bEnd.3 cells (ATCC) were grown in Dulbecco's modified Eagle's medium (4 mM L-glutamine adjusted to contain 1.5 g/L sodium bicarbonate and 4.5 g/L glucose, 90%; fetal bovine serum, 10%) (Atlanta Biological) in an incubator set to 37° C. with 5% $CO_2$. Aliquots of 60,000 cells in 0.5 mL were added directly onto sterile 25 mm round cover glasses inside 6 well plates. The cells were allowed to attach for 15 min after which an additional 1.5 mL of media was added. Next, the cells were placed in an incubator and allowed to grow for 48 h. PEG-HCCs were added to each well to obtain the following concentrations: 0 mg/L, 0.1 mg/L, 1 mg/L, 10 mg/L, 20 mg/L and 30 mg/L (triplicate). The cells were incubated for 1 h with the specific PEG-HCC concentrations after which 4,5-diaminofluorescein (DAF-2DA) at a final concentration of 5 mM was added to each well and incubated for an additional 5 min. The cells were then washed 3× with PBS and fixed with 4% paraformaldehyde for 15 min. The cells were washed 3× with PBS and then the cover glasses were attached to glass slides and coverslipped. A Nikon eclipse 80i microscope set to FITC was used to capture ten 40× fields per slide. Five cells from each 40× field were analyzed using NIS Elements software. An auto detect region of interest (ROI) function was used to select the cells and calculate their mean intensity and area. The intensity/area/exposure was calculated. An ANOVA was performed using the means followed by post tests using the Bonferroni method.

Confocal microscopy showed that the PEG-HCCs were taken up by the endothelial cells. See FIGS. 10-11. Staining against the PEG for the mock (FIG. 10B) and PEG (FIG. 10E) treated cells showed similar low intensity signals, indicating that uptake was dependent on the presence of carbon particles but not the PEG. The experiment was set as follows: bEnd.3 cells (~50,000/well, passage less than 30 times) were grown on coverslips placed in 6-well plates with 5 mL of complete media (high glucose Dulbecco's modified Eagle's medium (Gibco) formulated to contain 4 mM L-glutamine, 3.7 g/L sodium bicarbonate, 4.5 g/L D-glucose, 1 mM sodium pyruvate, 90%; fetal bovine serum, 10%; 1× pen-strep). Cells were later treated with 5 mL of complete medium in a 1:1 mixture with either water (Mock treatment), a solution of PEG in water, or a solution of PEG-HCCs in water. The final concentration of the PEG and PEG-HCCs in the treatment solution was 4 mg/L. Cells were incubated at 37° C. with 5% $CO_2$ for 5.5 h. The cells were then washed with ice cold PBS, then a solution of glycine (50 mM)/NaCl (100 mM), followed again by ice cold PBS in order to remove the carbon particles that are weakly attached to the membrane. Cells were fixed with 4% paraformaldehyde, then cell membranes were stained with Wheat Germ Agglutinin 594 before being permeabilized with PBT (PBS containing 0.1% Triton X-100), blocked with 5% BSA in PBT, and immunostained with a primary antibody against PEG (Epitomics, PEG Rabbit Monoclonal Antibody, RabMAb® #: 2061-1) and an Alexa-633 conjugated secondary antibody, with DAPI used as a nuclear counterstain. Each set of images was taken with the same settings on a Zeiss LSM 510 META confocal microscope, and are shown at the same brightness/contrast levels.

EXAMPLE 3

Use of PEG-HCCs to Treat Oxidative Stress Associated with Non-Alcoholic Fatty Liver Disease This Example pertains to the use of PEG-HCCs to treat oxidative stress associated with Non-alcoholic fatty liver disease (NALFD). NALFD is an increasingly common disease that can range from simple steatosis to cirrhosis and liver failure. It is often comorbidity with obesity, diabetes, metabolic syndrome, and insulin resistance. Although its exact etiology is not clear, oxidative stress has been implicated in the disease process both in animal models and human patients with NALFD. Antioxidants such as Vitamin E have had limited success in NAFLD clinical trials which may be linked to the fact that each molecule of Vitamin E can only scavenge one radical before needing to be regenerated. Here, Applicants demonstrate that PEG-HCC treatment can normalize hyperglycemia, reduce lipid peroxidation markers, and improve liver enzymes in the leptin-deficient (ob/ob) mouse model of NAFLD.

NAFLD encompasses a spectrum of liver diseases, ranging from simple steatosis and nonalcoholic steatohepatitis (NASH) to fibrosis and cirrhosis. With its prevalence estimated to be over 30 million people in the United States, NAFLD is an increasingly common health concern. NAFLD is also closely associated with obesity, insulin resistance and the metabolic syndrome. A "two-hit" model has been proposed to explain the development of NAFLD. In this model, excess accumulation of lipids in the liver is a precondition ("first hit"). Then a second insult to the liver such as inflammation and oxidative stress can induce progression from steatosis to more severe forms of NAFLD. Increased markers of oxidative stress have been found in both animal models and human patients with NAFLD. In addition, mitochondrial dysfunction and polymorphisms in the mitochondrial antioxidant superoxide dismutase 2 (SOD2) are associated with development and increased fibrosis in NAFLD.

Clinical studies of the antioxidant Vitamin E in NAFLD, including two randomized controlled studies, have had mixed results. Several of these studies have demonstrated little to no benefit of vitamin E when compared to concomitant weight loss. Other studies have found improved liver enzyme levels or better fibrosis scores. Antioxidants such as Vitamin E can only scavenge one radical per molecule before they must be regenerated by other antioxidants such as Vitamin C, thus creating a process where the radicals get handed off instead of being completely captured or eliminated.

Leptin deficient obese (ob/ob) mice are a common model of NAFLD. Although no NALFD model recapitulates all of the features of the human disease, ob/ob mice become obese, are hyperglycemic, and develop inflammation and severe steatosis. This Example examines the effectiveness of PEG-HCCs or vitamin E in preventing liver damage in the ob/ob mouse model of fatty liver disease.

EXAMPLE 3A

Materials and Methods

Animal Procedures

C57BL/6J wild type (WT, n=5/treatment) and B6.V-Lep$^{ob}$/J (ob/ob, n=9-10/treatment) mice (Jackson Labs, Bar Harbor, Me.) were randomly assigned to one of three treatment groups: vehicle (PBS), PEG-HCCs, or Vitamin E chow (2.2 IU DL-alpha-tocopheryl acetate/g chow; Harlan, Teklad, Indianapolis, Ind.). Mice were housed in a 12 hour light and dark schedule. Body weight and non-fasting glucose levels were measured weekly at the same time of day 5-6 days post-treatment. Food intake was measured weekly for each cage.

Drug Treatments

Mice were treated weekly for six weeks with one of the following treatments: 100 μL vehicle (PBS) i.v.; 100 μL of 200 mg/L PEG-HCCs in 1×PBS i.v. (~0.02 mg HCC core/mouse); 2.2 IU Vitamin E/g chow. Vitamin E treated WT and ob/ob mice averaged 8.2 and 11.6 IU Vitamin E/day, respectively.

Serum Collection

For liver enzyme experiments, blood was collected from the saphenic vein using a microvette (Sarstedt, Niimbrecht, Germany) at baseline, 2 weeks, 4 weeks, and 6 weeks. Blood was collected with a microvette via a cardiac puncture at the end of the experiment for TBARS measurements. The blood was spun at 7500 rpm for 7 minutes. Serum was collected and stored at −80° C. until use.

Liver Enzymes

Alkaline phosphatase (ALP), alanine aminotransferase (ALT), and aspartate aminotransferase (AST) levels were measured from serum with colorimetric assays (Teco Diagnostics, Anaheim, Calif.).

Tissue Collection

Mice were euthanized with an overdose of anesthetic. Cardiac puncture was performed to collect blood. Liver was excised, weighed, and either flash frozen and stored at −80° C. or fixed in 4% paraformaldehyde overnight at 4° C. then dehydrated and embedded in paraffin.

Lipid Extraction 100 mg of liver tissue was homogenized on ice in buffer. 300 μL of the homogenate was added to 600 μL of a 1:1 methanol chloroform mixture. The sample was vortex for one minute and then centrifuged. The methanol:chloroform layer was removed and dried in a new tube. 200 μL of chloroform was added to the dried sample and the samples were submitted to the Diabetes and Endocrinology core to be run on thin layer chromatography plates with lipid standards.

Lipid Peroxidation

Serum samples were tested for malondialdehyde levels with a TBARS kit (Cellbio Labs, San Diego, Calif.). Briefly, thiobarbituric acid was added to serum. Samples were incubated at 95° C. and then spun down. Butanol extraction was performed on samples to reduce interference from hemoglobin contamination. The supernatant was measured with a spectrophotometer. Malondialdehyde (MDA) levels were calculated from MDA standards.

Statistics

Body weight, food intake, non-fasting glucose, insulin tolerance tests, and liver enzyme levels were analyzed by repeated measures analysis of variance (ANOVA) with Bonferroni post tests to identify specific groups that were different. Lipid peroxidation, lipid extraction data, and liver weights were measured with two way ANOVA and Bonferroni post tests.

EXAMPLE 3B

Effects of PEG-HCCs on Weight, Food Intake, and Glucose Levels

Figure 20A:
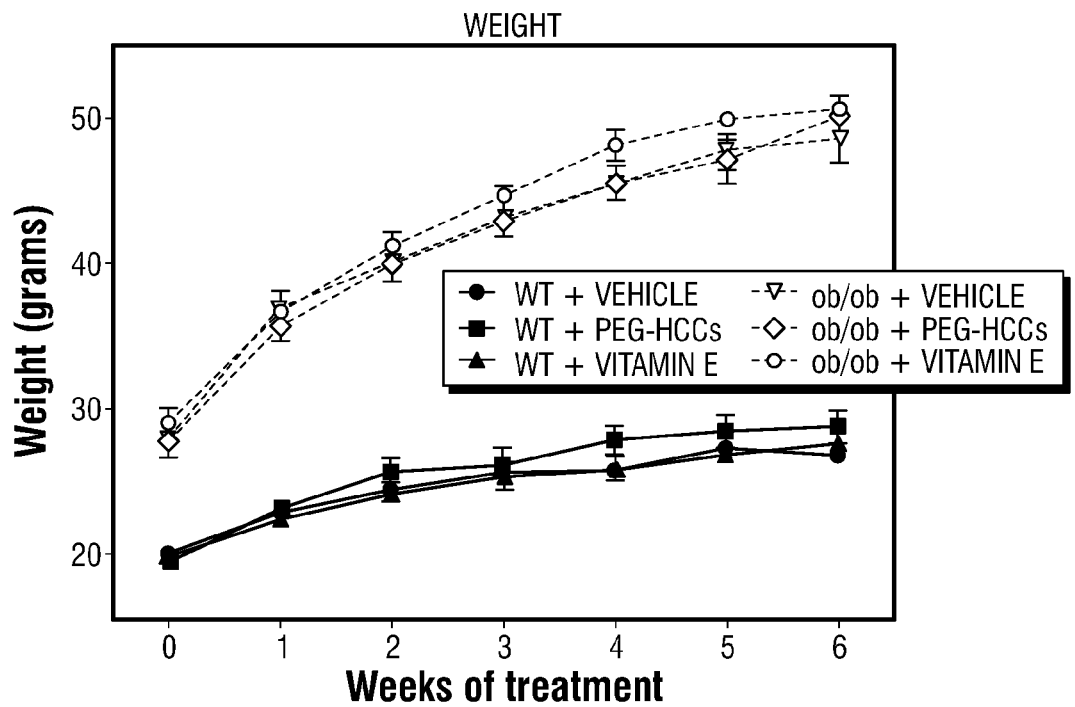
FIG. 20 shows data indicating that the body weight (FIG. 20A) and food intake (FIG. 20B) in wild-type (WT) and ob/ob mice are not altered by treatment with vehicle, PEG-HCCs, or Vitamin E chow for six weeks. Body weight and food intake (in grams) was measured weekly for the six week treatment period. Values are mean±SEM.
Figure 20B:
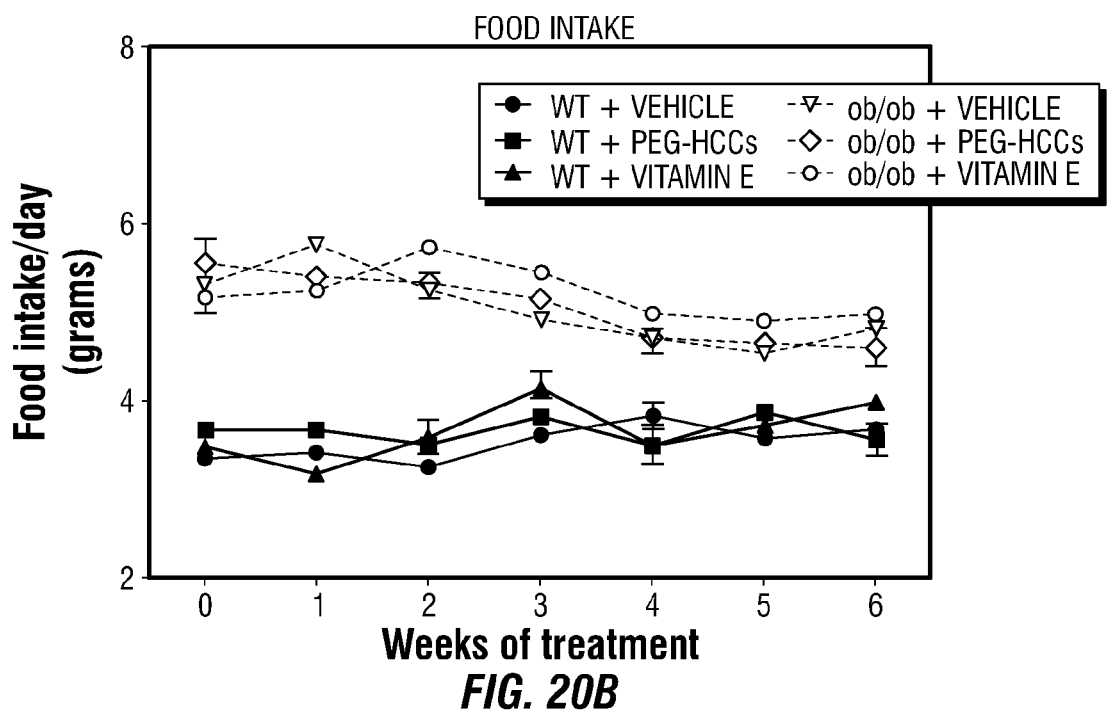
Figure 21:
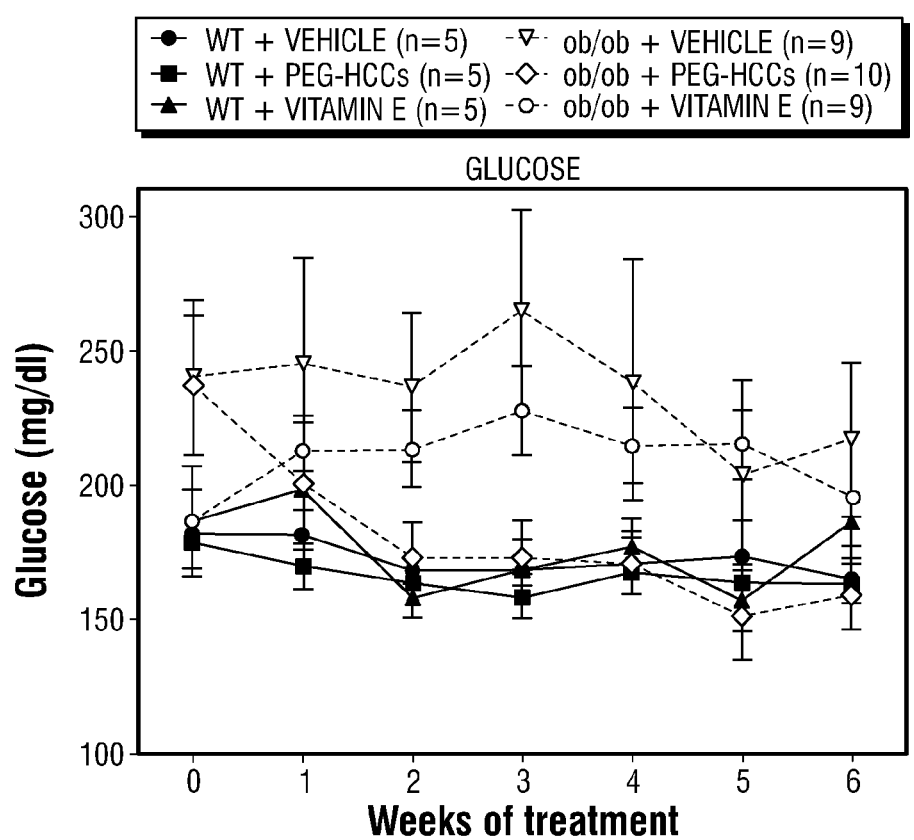
FIG. 21 shows that PEG-HCC treatment rapidly restored non-fasting glucose levels in ob/ob mice to WT levels. Glucose levels were measured prior to treatment (0 weeks of treatment) and then weekly for the six week treatment regimen. Glucose was measured 5-6 days after vehicle or PEG-HCCs treatment each week. Values are mean±SEM.

Body weight and food intake were monitored weekly in mice 5-6 days post-treatment. Both body weight and food intake were not significantly different within genotype using repeated measures ANOVA with a Bonferroni post-test. See FIGS. 20A-B. Wild-type (WT) mice weighed less and had lower food intake than ob/ob mice. However, antioxidant treatment did not affect these measures. On the other hand, non-fasting glucose levels for PEG-HCC-treated ob/ob mice were lower than the vehicle and Vitamin E treated ob/ob mice (RM ANOVA; $p<0.001$, $p<0.05$, respectively), but not different from the WT mice. See FIG. 21. Both the vehicle and Vitamin E treated ob/ob mice had significantly higher glucose levels than their WT treatment counterparts ($p<0.001$, $p<0.01$, respectively).

EXAMPLE 3C

Effects of PEG-HCCs on Liver Enzyme Levels

Figure 22A:
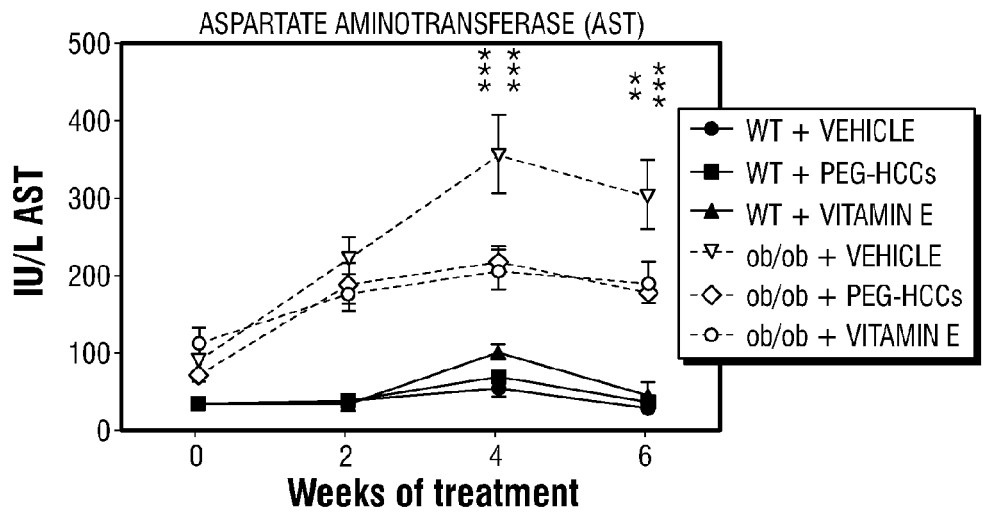
FIG. 22 shows that PEG-HCC and Vitamin E (VitE) treatment lowered aspartate aminotransferase (AST) levels (as compared to vehicle treatment) in mice. Serum was collected at baseline and after 2, 4, and 6 weeks of treatment. The serum was measured for AST (FIG. 22A), alanine aminotransferase (ALT) (FIG. 22B), and alkaline phosphatase (ALP) (FIG. 22C) levels. AST levels in ob/ob mice were significantly lowered by PEG-HCCs and Vitamin E. Vitamin E also had a transiently lower ALT level after 4 weeks of treatment. ALT levels were not changed by treatment. Values are mean±SEM. Green asterisks indicate significant differences between vehicle versus Vitamin E treated ob/ob mice, while blue asterisks indicate differences between vehicle and PEG-HCC treated ob/ob mice. $p<0.01$; *$p<0.001$.
Figure 22B:
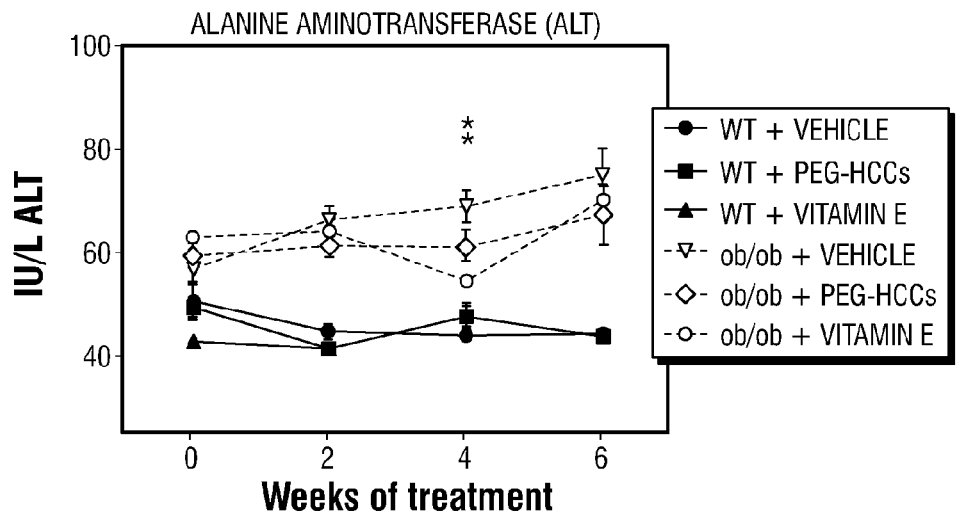
Figure 22C:
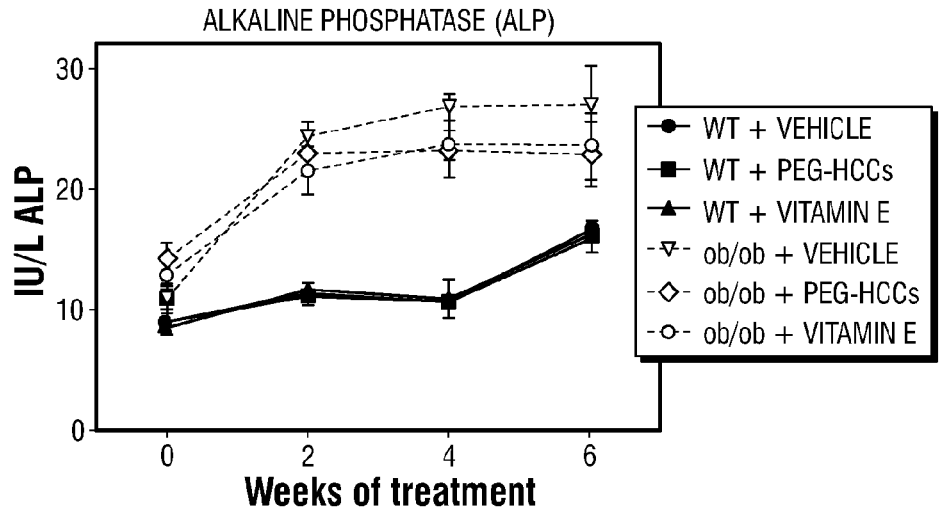

Aspartate aminotransferase (FIG. 22A), alanine aminotransferase (FIG. 22B), and alkaline phosphatase (FIG. 22C) levels were measured from serum prior to treatment and again at 2, 4, and 6 weeks of treatment. PEG-HCC treatment lowered AST levels after 4 and 6 weeks of treatment. Vitamin E treatment lowered AST levels at 4 and 6 weeks of treatment and briefly lowered ALT levels at 4 weeks. No significant changes were noted in alkaline phosphatase for any time point or treatment.

EXAMPLE 3D

Effects of PEG-HCCs on Lipid Peroxidation

Figure 23:
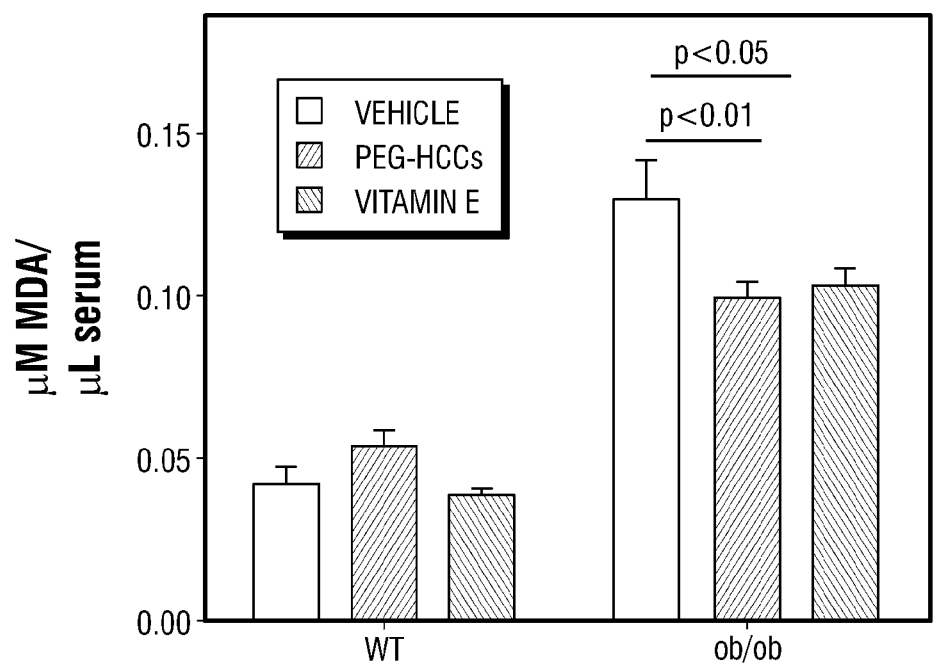
FIG. 23 shows that PEG-HCC and Vitamin E treatment for six weeks in ob/ob mice lowered lipid peroxidation levels compared to vehicle treated ob/ob mice. Serum from mice treated with vehicle, PEG-HCCs, or Vitamin E for six weeks was analyzed using a TBARS assay to measure malondialdehyde (MDA) levels. MDA is used as a marker for lipid peroxidation. PEG-HCCs and Vitamin E lowered MDA levels in ob/ob mice compared to vehicle treatment. Values are mean±SEM.
Figure 24A:
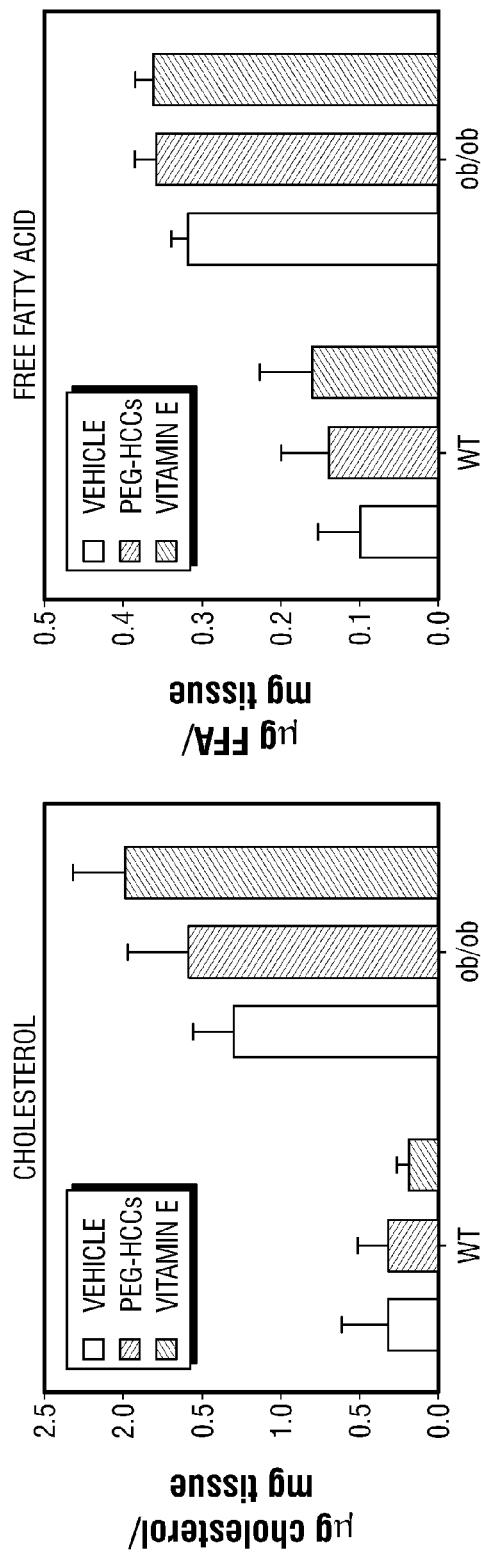
FIG. 24 shows that hepatic lipid levels in mice were unchanged by the vehicle, PEG-HCCs, or Vitamin E regimen after six weeks. The levels of cholesterol (FIG. 24A), free fatty acids (FIG. 24B), triglycerides (FIG. 24C), and cholesteryl esters (FIG. 24D) were higher in ob/ob mice compared to WT but unchanged by six weeks of treatment. Values are mean±SEM.
Figure 24B:
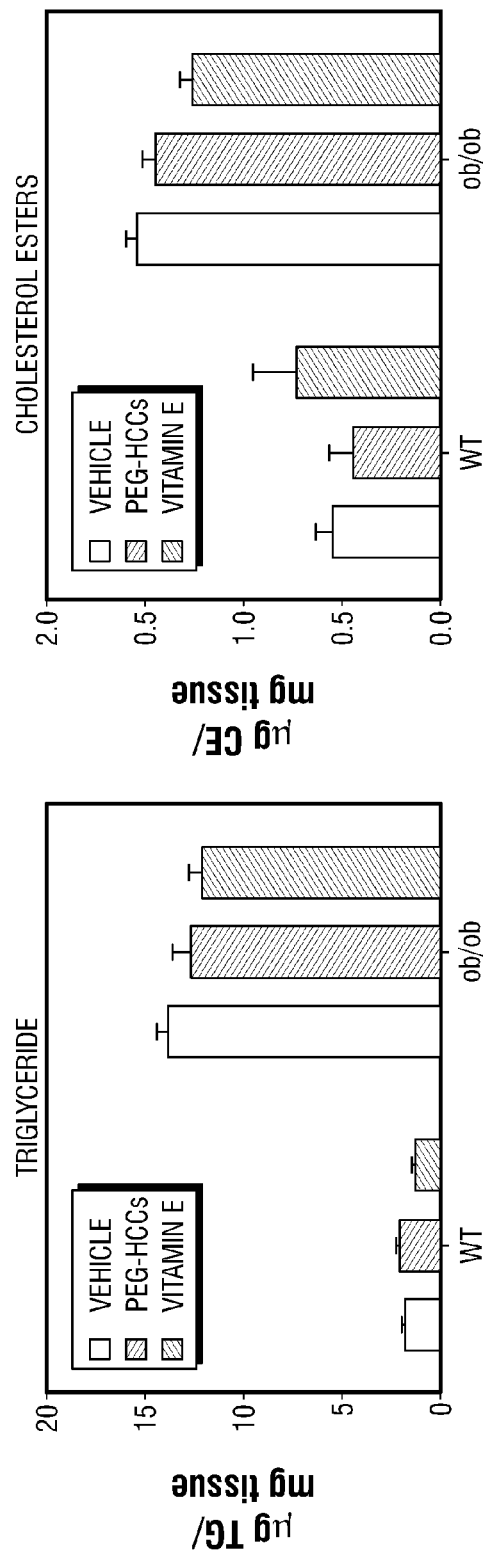
Figure 24C:
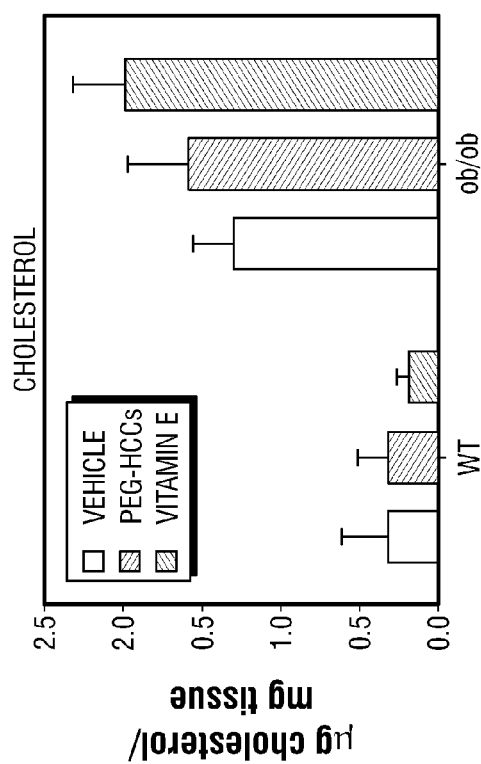
Figure 24D:
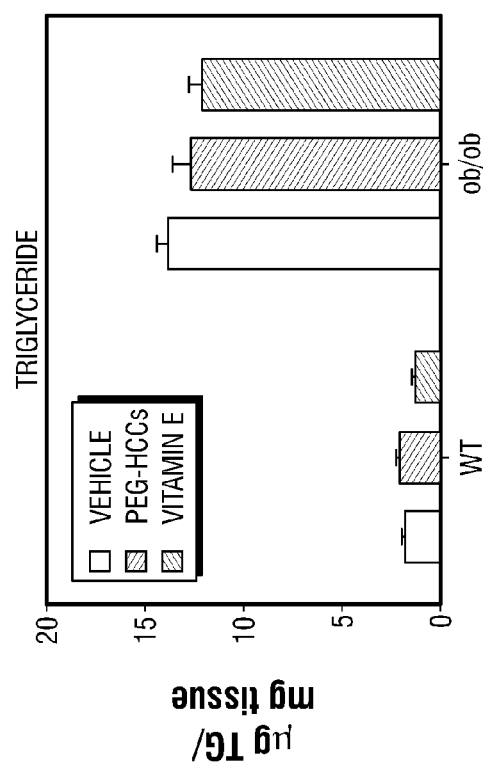

Maldondialdehyde (MDA) levels were measured in serum as a marker of lipid peroxidation. Serum was taken after six weeks of treatment. As illustrated in FIG. 23, ob/ob mice had significantly higher MDA levels than WT ($p<0.0001$). Bonferroni post test showed that PEG-HCC and Vitamin E-treated ob/ob mice had lower MDA levels than vehicle treated ob/ob mice ($p<0.01$ and $p<0.05$, respectively). See FIG. 23.

EXAMPLE 3E

Effects of PEG-HCCs on Lipids

No significant changes were seen in the levels of hepatic cholesterol, free fatty acids, triglycerides, and cholesteryl esters with weekly treatment with vehicle or PEG-HCCs for six weeks or daily administration of Vitamin E chow for six week. See FIG. 24.

Discussion

NAFLD is a complex disease pathology whose underlying causes are still not completely understood. Reactive oxygen species have been implicated in the pathogenesis of NAFLD as well as in its common comorbidities of diabetes and insulin resistance. Depletion of antioxidants and increased lipid peroxidation by-products have been reported in patients with NAFLD. It has been found that oxidative stress markers in humans such as TBARS and protein carbonylation were independently associated with NAFLD, regardless of gylcemic status. Mitochondrial dysfunction that impairs the mitochondrial respiratory chain can result in increased production of reactive oxygen species such as superoxide anion. Both mitochondrial dysfunction and reduced mitochondrial respiratory chain activity have been reported in human patients and mouse models of NAFLD. Genetic factors that can increase susceptibility to oxidative stress have also been associated with more advanced NAFLD. A polymorphism in the mitochondrial superoxide oxide dismutase (SOD2) gene that imparts reduced activity and targeting to the mitochondria has been linked to increased fibrosis in non-alcoholic steatohepatitis. Oxidative stress may play a role in triggering hepatic inflammation in obese NAFLD patients.

Some groups have proposed that oxidative stress and mitochondrial dysfunction precede the appearance of insulin resistance. For instance, it has been reported that insulin resistance is a cellular antioxidant defense that could be induced by increased mitochondrial superoxide anion levels and reversed by mitochondrial superoxide dismutase mimetics. In fact, even one of the common methods to produce a mouse model of NAFLD, feeding mice a methionine choline deficient diet, has been reported to induce mitochondrial respiratory chain dysfunction and increased oxidative stress.

In this Example, Applicants have reported that treatment of ob/ob mice with the nano-antioxidant PEG-HCCs once weekly for 6 weeks eliminated hyperglycemia, reduced aspartate aminotransferase levels, and lowered lipid peroxidation levels. Daily vitamin E treatment was also able to reduce aspartate aminotransferase levels and lower lipid peroxidation markers, but not restore normal glucose levels. Similar improvements have been seen in some of the clinical trials with Vitamin E and NAFLD. None of the treatments caused any significant change in body weight, liver weight, or food intake in WT or ob/ob mice. The ob/ob mice had significantly higher body weight, liver weight, and food consumption than their WT counterparts as expected in this mouse model.

NAFLD is a complex disease involving many different pathways and pathogenic processes. Therefore, therapeutic approaches to NAFLD can also be multi-pronged to address different aspects of the disease processes. For instance, PEG-HCCs can also be loaded with payload drugs that can target other sources of NAFLD pathology such as steatosis or inflammation.

EXAMPLE 4

Effects of PEG-HCCs and SWNTs on Brain Endothelial Cells

In this Example, Applicants show that SWNTs and PEG-HCCs are biocompatible with cultured brain endothelial cells (b.End3). Applicants also show that SWNTs and PEG-HCCs are able to protect b.End3 cells from oxidative stress.

EXAMPLE 4A

Materials and Methods

Preparation of pluronic-wrapped SWNTs (pl/SWNTs) and PEG-HCCs

SWNTs (lot # HPR 187.4) were purchased from HiPco Laboratory at Rice University. The SWNTs were purified following a reported protocol. *Chem. Mat.* 2009 (21):3917-3923. The purified SWNTs (0.07 g) and Pluronic F 108NF Prill Poloxamer 338 (donated by the BASF Corporation, 2.25 g) in NANOPure water (Barnstead system, 18 MΩ resistivity, 225 mL) were homogenized for 1 h by using a homogenizer shaft driven by a Dremel Multipro model 395 motor and model 225 flexible shaft. The mixture was then sonicated by using a cup-horn sonicator (Cole Parmer Ultrasonic Processor Model CP 750) for 10 min at 78% amplitude. The mixture was then ultracentrifuged for 6 h at 26,000 rpm. The pl/SWNTs in solution were decanted, and the solid material was discarded according to established approved protocols. The concentration of the resultant pl/SWNTs, determined by Beer's law analysis using an empirically derived extinction coefficient of 0.0430 L/mg at $\lambda_{max}$=763 nm, was 10 mg/L. The solution was concentrated using a rotary evaporator and sterile filtered using a 0.45 µm pore size membrane, producing a final solution with a pl/SWNTs concentration of 12 mg/L.

The PEG-HCCs were prepared as recently reported. *ACS Nano.* 2010 (4):4621-4636. The PEG-HCCs were sterile filtered using a 0.22 µm pore size membrane.

Cell Culture

Murine brain endothelioma (bEnd.3, CRL 2299, ATCC, Manassas, Va.) were cultured in Dulbecco's Modified Eagle Medium: Nutrient Mixture F-12 (50:50) with 4 mM L-glutamine media, supplemented with 10% fetal bovine serum (both from HyClone) and 1% Pen Strep (+10,000 u/mL penicillin/+10,000 µg/mL streptomycin, from GIBCO). During the second week, between the 4$^{th}$ and 6$^{th}$ passage, cell experiments were performed.

Clonogenic Survival Assay

Following a published protocol (*Nat Protoc* 2006(1): 2315-2319), this assay was carried out three times for each concentration of the PEG-HCCs and pl/SWNTs. For each nanomaterial treatment, 30,000 cells/mL were plated in 5 mL of full media. After 24 h, the media was removed, and the cells were washed with 1× phosphate buffered saline (PBS). The cells were treated with the desired concentrations of nanomaterials in 5 mL full media and incubated for 24 h. Cells were detached using 1 mL of 0.25% trypsin and 0.1% ethylenediaminetetraacetic acid for 5 min and then suspended with an additional 4 mL full media. The number of cells in the 5 mL suspension was determined using a hemocytometer and 2000 cells were plated to assay colony formation. Colonies were defined to consist of at least 50 cells. When colonies were sufficiently large on control plates (generally after 7-14 d), the media was aspirated and the plates gently washed by submersion in water. Colonies were stained using 2 mL of 0.25% crystal violet (Sigma-Aldrich, catalog C0775) in methanol for 3 min. The plates were gently washed with water to remove excess stain, and air-dried at room temperature. Stained colonies were counted. Values were normalized to the 0 mg/L nanomaterial control.

Trypan Blue Staining

The following protocol was carried out three times for each concentration of the PEG-HCCs and pl/SWNTs. For each nanomaterial treatment, 150,000 cells were plated in full media in four 6-cm plates. After incubation for 24 h, the media was removed, and the cells were washed with 1×PBS. The cells were treated with the desired concentrations of nanomaterials in 5 mL full media. For the pl/SWNTs, the samples were prepared such that the concentration of pluronic was kept constant at 1% by weight. The treated cells were incubated for 6 h or 24 h. Cells were detached using 1 mL of 0.25% trypsin and 0.1% ethylenediaminetetraacetic acid for 5 min and then suspended with an additional 4 mL of serum free media. Cells were pelleted twice at 1,000 rpm for 5 min and washed in 1×PBS. Cells were then resuspended in 1 mL 1×PBS and mixed with 1 mL of 0.4% trypan blue solution (Invitrogen, Carlsbad, Calif.). After 5 min, an aliquot of the cells was removed and blue (dead cells) and non-stained cells were counted in 4 quadrants of a hemocytometer. After 15 min, another aliquot was removed and the count was repeated. The values presented are the average of the counts, and the values were normalized to the 0 mg/L nanomaterial control. The exposure of cells to trypan blue for a period longer than 30 min was avoided. At extended times, an increase in the dead cell population due to the trypan toxicity was observed.

Cyctochrome C Assay for Antioxidant Strength

Superoxide scavenging efficiency was determined using a method described previously. *J. Neurosci. Methods.* 2000 (97):139-144. Briefly, three reaction solutions were prepared, A-C. Solution A contained catalase (320 µl; 6000 U/mL in PBS; Sigma-Aldrich), hypoxanthine (320 µl; 10 mM solution in 30 mM NaOH; Sigma-Aldrich), cytochrome c (755 µl; 1.95 mM solution in PBS; Sigma-Aldrich), and 14.6 mL of PBS. Solution B consisted of xanthine oxidase (57 µL; 167.5 mU/mL in PBS; Sigma-Aldrich) and PBS (743 µL). Additional B solutions were prepared with the test antioxidant compounds, pl/SWNTs and PEG-HCCs, replacing the PBS in volumes ranging from 1-743 µL. All solution B preparations were 800 µl, enough solution to run four replicates of each antioxidant concentration. Solution C included Xanthine oxidase (57 µL; 167.5 mU/mL in PBS), superoxide dismutase (90 µL; 10200 U/mL in PBS; Sigma-Aldrich), and PBS (653 µL) to allow determination of non-superoxide-dependent reduction of cytochrome c (total volume 800 µL).

The assay was performed in a 96-well plate with a final reaction volume of 325 µL per well. Each plate contained the following conditions, using four wells for each condition: (1) a water blank (325 µL per well), (2) solution B without any nanomaterials (the control reaction; 162.5 Ll per well), (3) solution B with the nanomaterials (162.5 µL per well), and (4) solution C, containing SOD (162.5 µL per well). After all of the above solutions had been added to the plate, 162.5 µL of solution A was rapidly added to each well except for the water blanks. Two min after the addition of solution A, a BIO-TEK Powerwave XS spectrophotometer (Winooski, Vt.) supported by SOFTmax Pro software (Molecular Devices, Sunnyvale, Calif.) was used to read the plate at 550 nm on a basic kinetic protocol to measure absorbance every 45 s, for a total reaction time of 8 min. The reaction rate (OD/min) was determined and then plotted against the log of the concentration of the test compound. $IC_{50}$ was determined using a nonlinear regression analysis (GraphPad Prism software version 5.0, La Jolla, Calif.). For each nanomaterial, this entire assay was performed at least three separate times.

b.End3 Cell Staining for Von Willebrand Factor bEnd.3 cells (200,000/well, passaged fewer than 10 times) were plated onto 25 mm poly-D-Lysine-coated glass disks placed within 6-well plates. To each well was added 2 mL of complete growth medium (Dulbecco's modified Eagle's medium with 4 mM L-glutamine adjusted to contain 1.5 g/L sodium bicarbonate and 4.5 g/L glucose, 90%; fetal bovine serum, 10%, ATCC, Manassas, Va.). Cells were incubated at 37° C. with 5% $CO_2$ for 24 h. After incubation, the cells were fixed in 100% methanol at −20° C. for 5 min. The methanol was removed and the cells were dried at room temp in a biological hood. To the fixed cells, 2 mL of 0.1% Triton X-100 in PBS was added. After 30 min, the cells were washed 3× with PBS. The cells were then incubated for 30 min in 2 mL of 3% normal goat serum and then washed 3× with PBS. Cells were then incubated overnight at 4° C. in the presence of a 1:400 dilution of the primary antibody (Polyclonal Rabbit Anti-Human Von Willebrand Factor antibody, DAKO, Glostrup, Denmark) in PBS. Next, the cells were washed 3× in PBS. The cells were then incubated with a 1:1000 dilution of the secondary antibody (Alexa Fluor goat anti-rabbit 594, Invitrogen, Carlsbad, Calif.) for 4 h at room temp in the dark. Cells were then washed 3× with PBS. The 25 mm disks were then removed from the wells and attached to glass slides using an adhesive (clear nail polish). Coverslips were then applied using Vectashield Hard Set Mounting Medium with DAPI (Vector Labs, Burlingame, Calif.) and allowed to harden at 4° C. in the dark. The slides were then analyzed using a Nikon Eclipse 80i epi-fluorescense microscope. Von Willebrand Factor was detected with Texas Red; DAPI is blue.

Antimycin A/DHE Assay for Intracellular Antioxidant Strength

Cells were treated as previously described (*Biochem. J.* 2009(418):29-37), with slight modification to accommodate antioxidant treatment and cell type. Briefly, bEnd.3 cells were grown in 6-well culture plates for 72 h. Culture media was reduced to 1 mL. Cells were treated with 1×PBS (5 µl) or 2 mM antimycin A (5 µl Sigma-Aldrich, St. Louis, Mo.), which induces intracellular ROS. The cells were then incubated for 10 min at 37° C. and 5% $CO_2$. Antioxidant treatments were then given as follows: PEGylated SOD (4 U, Sigma-Aldrich), N-tert-Butyl-alpha-phenylnitrone (PBN; 2 µl of 300 mM; Acros Organics, Geel, Belgium), PEG-HCCs (1, 10, 20, 40 µL of 100 mg/L), and pl/SWNT (10, 40 µL of 12 mg/L). Controls run to assess baseline antioxidant nanomaterial fluorescence used the highest volume listed above for each nanomaterial.

Dihyroethidium (DHE; 1 µL of 5 mM; Fluka Chemie GmbH, Buchs, Switzerland) was added 5 min later and the cells were incubated at 37° C. and 5% $CO_2$ for 25 min. Cells were washed twice with 1×PBS, removed from the wells with 0.5 mL trypsin, suspended in 2 mL PBS with 2% fetal calf serum in fluorescent-activated cell sorting tubes, and washed twice. SytoxRED (1 µl Invitrogen, Carlsbad, Calif.) was added to each tube. 15 min later, and cells were run on a flow cytometer (BD FACSCanto II, San Jose, Calif.). For each sample, 10,000 cells were analyzed, and the mean fluorescent intensity was measured with assistance from the cytometry and cell sorting core (488 nm excitation laser for DHE detection and 637 nm excitation laser for SytoxRED detection). DHE reacts with ROS to form 2-hydroxyethidium, which possesses red fluorescence when excited near 480 nm. Thus, the increase in red fluorescence is proportional to the ROS in the sample. The mean fluorescent intensity for each experiment repetition was normalized to control cells from that individual experiment to avoid error due to daily fluctuations in the lasers.

Two additional control experiments were performed to test whether prolonged pretreatment exposure to known antioxidants was able to reduce superoxide levels from antimycin A treatment. In these cases, an identical procedure to that described above was followed, except that after the cells had grown in the 6-well plates for 58 h, they were treated with either 40 U PEGylated SOD or 20 μL 300 mM PBN. Fourteen h later, at the 72 h time point, the cells were treated with 1×PBS (5 μL) or 2 mM antimycin A (5 μL). The cells were then incubated for 10 min at 37° C. and 5% $CO_2$. The cells were then treated again with either 40 U/well PEGylated SOD or 20 μL 300 mM PBN. DHE staining and analysis was identical to that described above.

Protection of b.End3 Cells from Oxidative Stress-Induced Death bEnd.3 cells (~200,000/well, passaged less than 10 times) were plated in 6-well plates. To each well was added 2 mL of complete growth medium (Dulbecco's modified Eagle's medium with 4 mM L-glutamine adjusted to contain 1.5 g/l sodium bicarbonate and 4.5 g/l glucose, 90%; fetal bovine serum, 10%, ATCC, Manassas, Va.). Cells were incubated at 37° C. with 5% $CO_2$ for 72 h. Media was removed and replaced with 1 mL fresh media. Cells were then treated with 15 μl/well 3 mM antimycin A or 1×PBS. This dose of antimycin A was selected empirically to provide a midrange toxicity towards the bEnd.3 cells. Cells were incubated at 37° C. with 5% $CO_2$ for 10 min then one of the following was added: 40 μL of 100 mg/L PEG-HCCs, 40 μL of 12 mg/L pl/SWNTs, 40 U PEGylated SOD, or 20 μL of 300 mM PBN. Cells were then incubated at 37° C. with 5% $CO_2$ for 24 h. Cells were washed twice with 1×PBS, removed from wells with 0.5 mL trypsin, suspended in 2 mL PBS with 2% fetal calf serum, and washed twice. Cells were resuspended in 0.5 mL 1×PBS and counted on a Vi-Cell XR Analyzer (Beckman Coulter, Brea, Calif.). Viable cells/mL was recorded and the percent relative to control was calculated from the PBS-treated control cells.

Statistical Methods

Assays for intracellular antioxidant strength and oxidative stress-induced death were analyzed with one-way analysis of variance (ANOVA) followed by a Bonferroni post test to compare all groups. Assays for toxicity were analyzed by comparing each treatment to the control treatment for that experiment using a two-tail T-test assuming equal variances. A p-value <0.05 was considered significant.

EXAMPLE 4B

Characterization of PEG-HCCs and pl/SWNTs

Figure 1D:
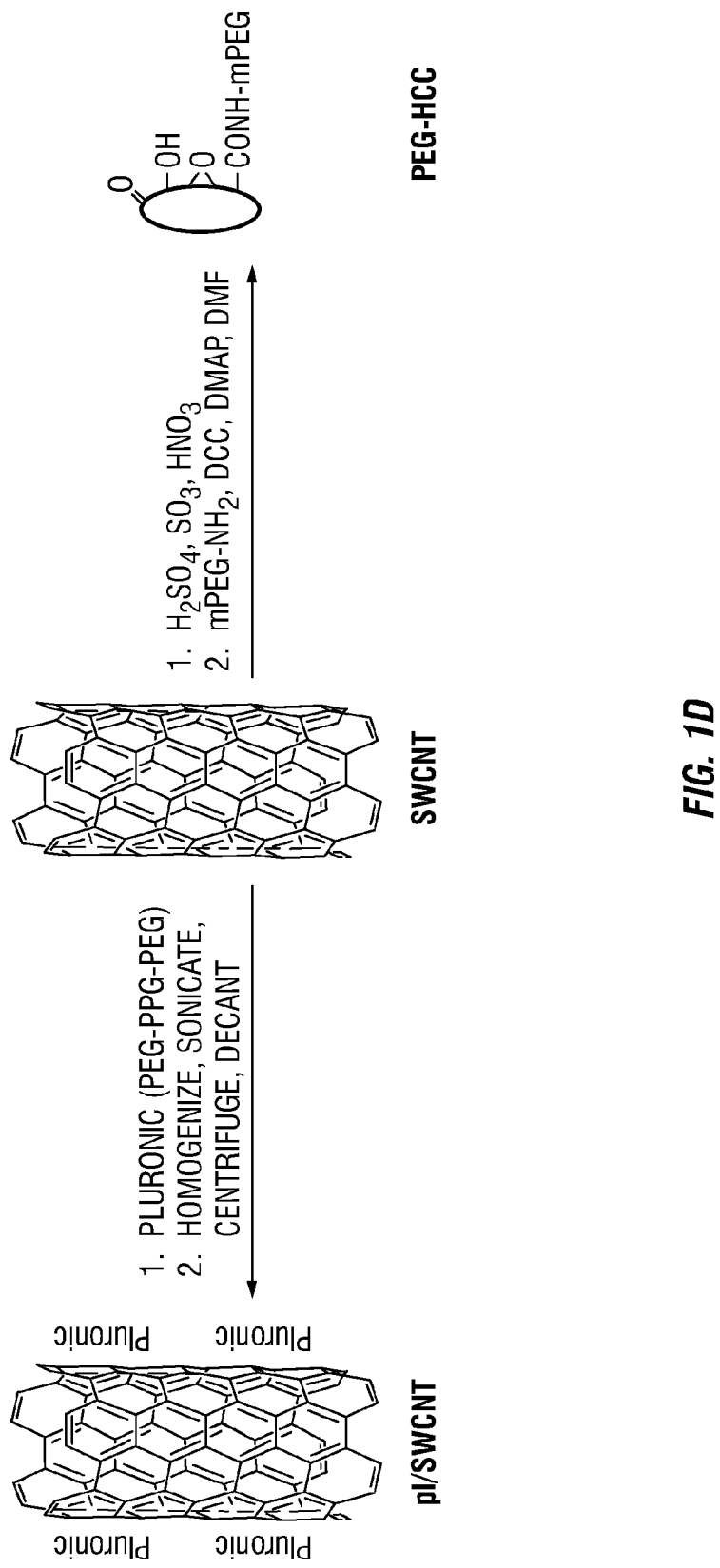
FIG. 1D shows a scheme by which polyethyleneglycol functionalized hydrophilic carbon clusters (PEG-HCCs) and pluronic single-walled nanotubes (pl/SWNTs) are prepared. HCCs were generated by treating SWNTs with oleum and nitric acid. Following purification, the HCCs were functionalized with PEG via coupling to the carboxylic acids present on the HCCs, thereby forming PEG-HCCs. The pl/SWNTs were prepared by mixing pluronic with SWNTs.

FIG. 1D illustrates a scheme for preparing PEG-HCCs and pluronic wrapped SWNTs (pl/SWNTs). PEG-HCCs are soluble in water and other biologically relevant solutions, such as PBS or cell culture media. On the other hand, the SWNTs are insoluble in these solutions. In order to use them, the SWNTs were wrapped with pluronic (pl/SWNTs). Pluronic (BASF Corporation) is a triblock copolymer of poly(ethylene glycol)/poly(propylene glycol)/poly(ethylene glycol). The pl/SWNTs and PEG-HCCs vary in size, shape and surface functionality. SWNTs are generally long (500 nm-5 μm) and tubular. The poly(propylene glycol) block of the pluronic wraps around the SWNTs' nearly pristine carbon surfaces, thereby imparting aqueous solubility.

On the other hand, HCCs are generally shorter (e.g., <40-nm-long). In addition, the HCC side walls may be disrupted by oxidation. The surface of the HCCs may also bear a number of functional groups, including ketones, alcohols, epoxides and carboxylic acids, such that, stoichiometrically, for every four carbons there may be one oxygen. Furthermore, as illustrated in FIG. 1D, solubilizing PEG groups may be covalently attached to the PEG-HCCs via a N,N'-dicyclohexylcarbodiimide-mediated coupling to the carboxylic acids. One way in which these differences are reflected is in the concentrations that can be achieved in aqueous solutions. These concentrations are measured for the carbon core of each nanomaterial using UV analysis. For instance, the PEG-HCCs can be soluble in water at 1000 mg/L, while the concentrations achieved for dispersed pl/SWNTs are generally around 10 mg/L for the SWNTs used in this work.

EXAMPLE 4C

Inhibition of Cytochrome C Oxidation by PEG-HCCs and pl/SWNTs

Figures 25A, 25B:
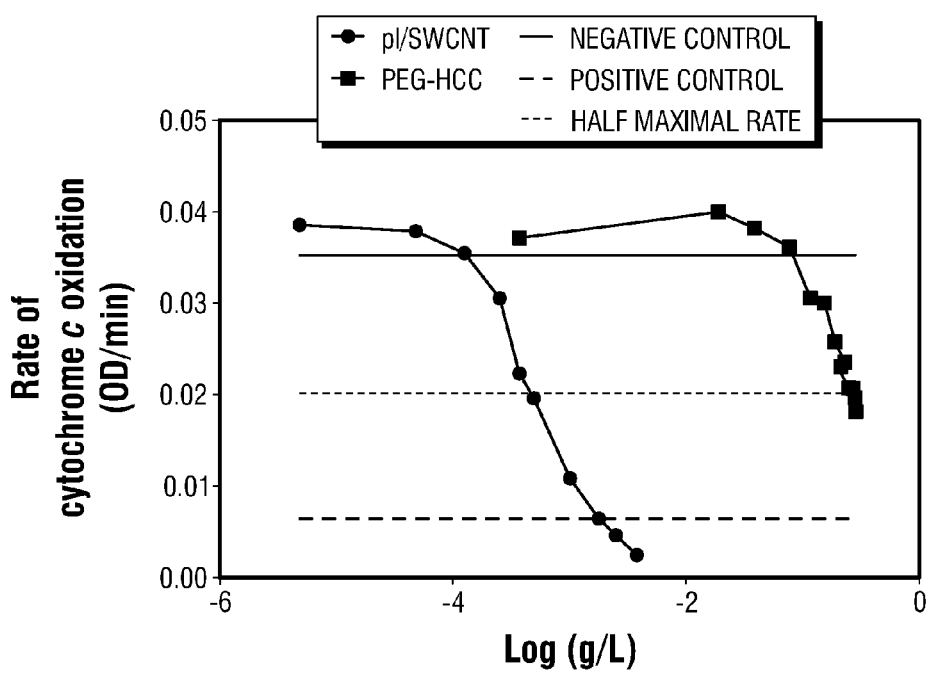
FIG. 25A shows a table of $IC_{50}$ values for the oxidation of cytochrome c by superoxide.
FIG. 25B shows nonlinear regression plots from separate experiments measuring the rate of cytochrome c oxidation relative to the log of the concentration of the carbon core of pl/SWNTs and PEG-HCCs.

The ability of the pl/SWNTs and PEG-HCCs to quench ROS was evaluated by exposing them to superoxide anion generated by the metabolism of hypoxanthine by xanthine oxidase. Since the carbon cores of the pl/SWNTs and PEG-HCCs can play a role in their antioxidant properties, their ability to inhibit the oxidation of cytochrome c was calculated on this basis. Both the PEG-HCCs and the pl/SWNTs were effective antioxidants and were able to achieve inhibition equivalent to half that of the positive control ($IC_{50}$), which was a large excess of SOD. See FIG. 25. The $IC_{50}$ values were 200 mg/L for the PEG-HCCs and 0.61 mg/L for the pl/SWNTs.

EXAMPLE 4D

Evaluation of the Toxicity of PEG-HCCs and pl/SWNTs

The potential cytotoxicity of the pl/SWNTs and PEG-HCCs was evaluated using b.End3 cells. See FIG. 26. It was first confirmed that this cell line is an endothelial cell line, based on the expression of Von Willebrand Factor. See FIG. 26A.

Figures 26A, 26B:
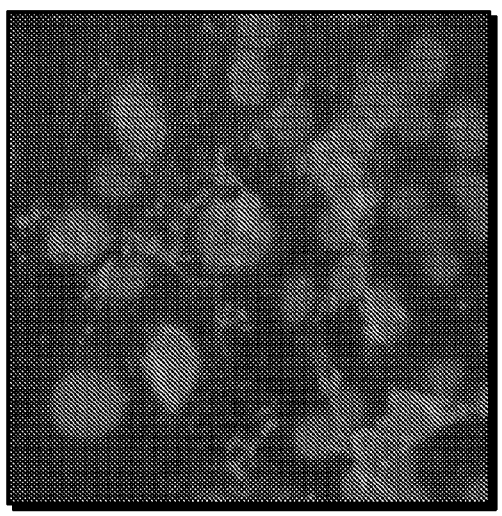
FIG. 26A shows an image identifying cultured b.End3 cells as endothelium based on expression of Von Willebrand Factor (red). Blue stain (DAPI) indicates cell nuclei.
FIG. 26B shows data relating to the survival of b.end3 cells treated with various concentrations of PEG-HCCs or pl/SWNTS, as measured by trypan blue staining.

To evaluate the effects of PEG-HCCs and pl/SWNTs on b.End3 cells, Applicants utilized a trypan blue assay. See FIG. 26B. Trypan blue is a membrane-impermeant dye so it only stains dead or dying cells with damaged membranes. The b.End3 cells were incubated in the presence of various concentrations of the PEG-HCCs (0-200 mg/L) and pl/SWNTs (0-10 mg/L) for 6 h and then stained with trypan blue for live/dead cell counting. As shown in FIG. 26B, no toxicity was observed at this time point for any of the concentrations of either material. However, when the incubation time was extended to 24 h, a clear difference between the materials was observed, as the PEG-HCCs were still non-toxic while the pl/SWNTs were cytotoxic. Applicants further investigated this difference in toxicity by performing a clonogenic survival assay. See FIG. 26C. For this assay, b.End3 cells were incubated in the presence of various concentrations of the PEG-HCCs (0-200 mg/L), pl/SWNTs (0-10 mg/L) or 1% pluronic only for 24 h. Then, for each treatment, an equal number of cells were transferred to a new culture dish and allowed to grow until the control dish showed a sufficient number of colonies for counting. This generally occurred after 7-14 d, at which time all of the plates were stained and the number of colonies was determined for each treatment and compared to the control. The PEG-HCCs were once again non-toxic at all of the concentrations tested. On the other hand, Applicants found that 1% pluronic alone was highly toxic under these conditions, resulting in just 7% colony formation relative to control. Due to the magnitude of the toxicity associated with 1% pluronic, it cannot be determined in these cellular assays if the SWNTs contributed to the toxicity seen for the pl/SWNTs.

EXAMPLE 4E

Antioxidant Activities of PEG-HCCs and pl/SWNTs in Living Cells

Figure 27:
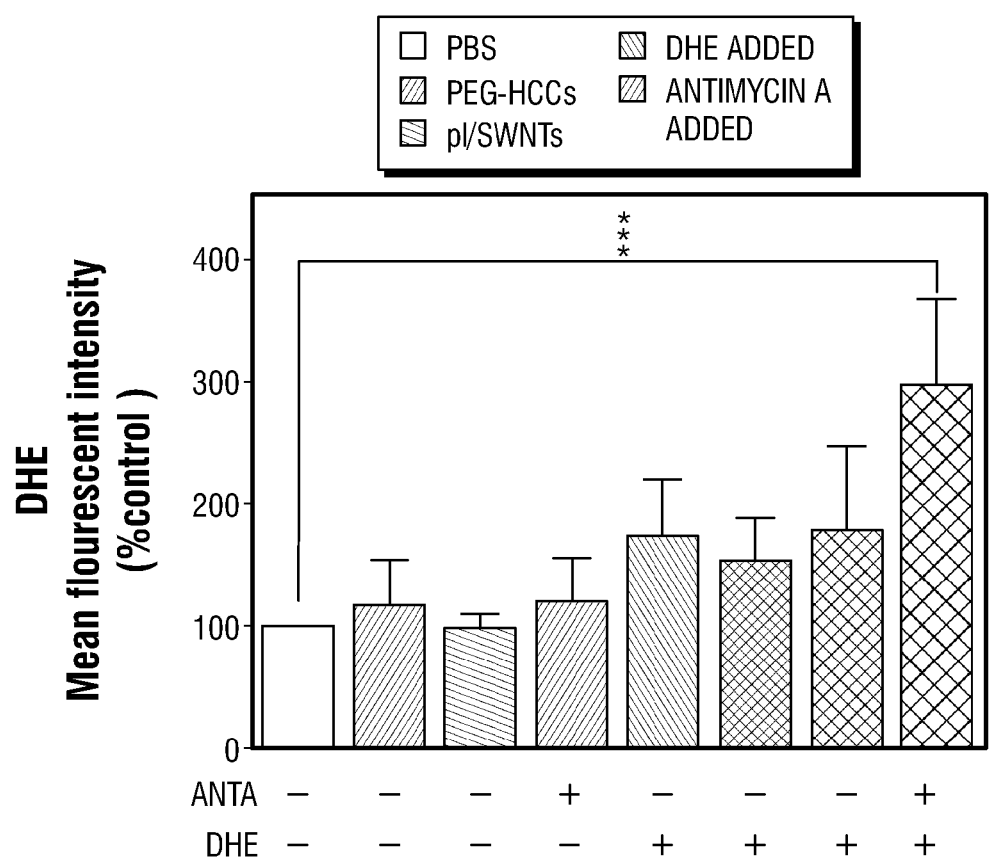
FIG. 27 shows a table of controls for intracellular superoxide assay to determine whether there is direct interference between the carbon nanomaterials and the fluorescent assay. Cells were treated with or without antimycin A (vertical striped bars). PEG-HCCs or pl/SWNTs were added fifteen minutes later (light and dark grey bars, respectively), followed by DHE (horizontal striped bars) where indicated. There did not appear to be any reduction in either non-specific fluorescence (first three bars) or background fluorescence after addition of DHE (bars 5-8). The last combination, DHE and antimycin A treated (vertical and horizontal striped bar) demonstrated, as expected, a significantly higher DHE staining compared to the untreated control (white solid bar).
Figure 28:
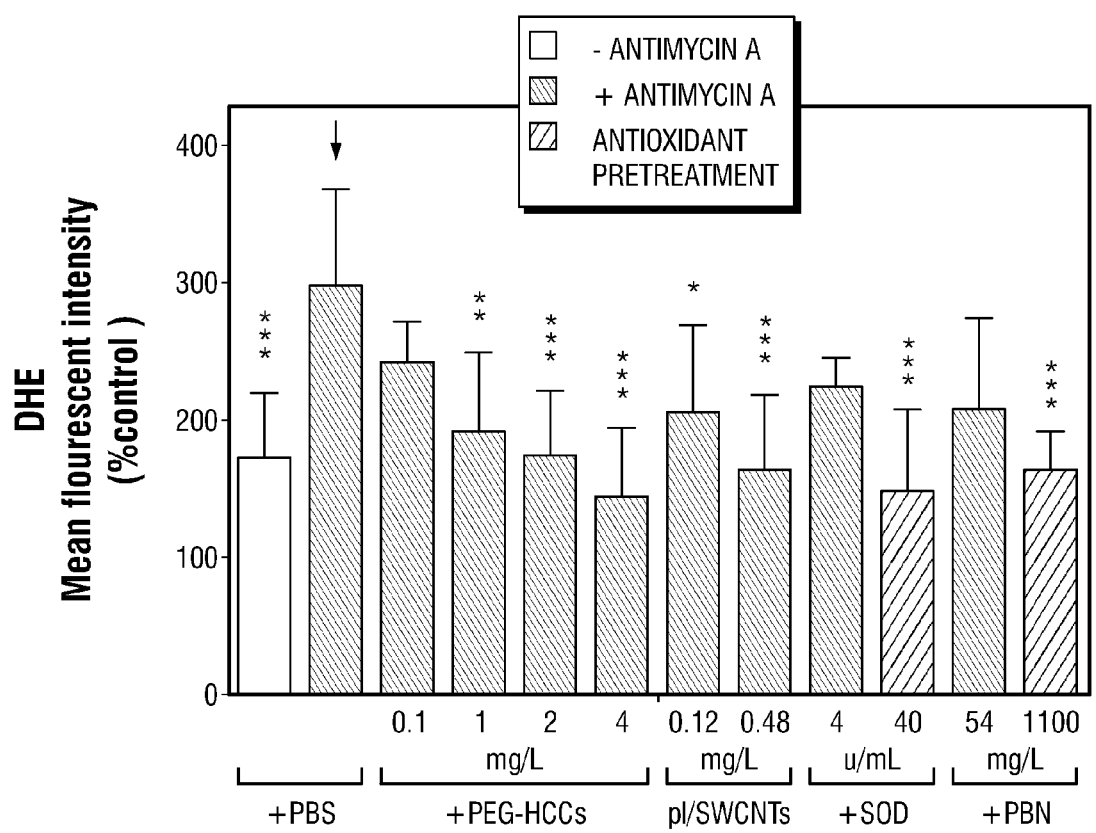
FIG. 28 shows intracellular ROS levels for b.End3 cells as determined by DHE staining and flow cytometry. Superoxide production was induced using antimycin A, and superoxide levels were measured with the superoxide-specific dye, DHE. Neither the PEG-HCCs nor the pl/SWNTs alone altered the DHE fluorescence. The level of DHE fluorescence in cells not treated with antimycin A (solid white bar) was significantly lower than the fluorescence in antimycin A-treated cells (grey bar+PBS) indicating higher superoxide levels in antimycin A-treated cells. Following antimycin A exposure, treatment with PEG-HCCs (grey bars+PEG-HCCs) or pl/SWNTs (grey bars+pl/SWNTs) reduced the level of ROS in a dose dependent manner (doses for antioxidant treatments are located below the bars). Following antimycin A exposure, treatment with PEGylated SOD (grey bar+SOD) or PBN (grey bar+PBN) at similar concentrations by weight to the dose of the maximally effective nanomaterials had no statistically significant effect. However, pretreatment with a higher dose (40 U/L PEGylated SOD and 1100 mg/L PBN, striped grey bars) along with the standard treatment at that same elevated dose reduced the level of ROS. All statistics are compared to the bar with an arrow (+PBS grey bar). *p-value<0.05; p-value<0.01; *p-value<0.001.

Having established that the PEG-HCCs were not toxic to b.End3 cells, their ability to quench intracellular ROS was evaluated. Since the pl/SWNTs did not cause cell death in the first 6 h, they were included in the assay for comparison. The b.End3 cells were treated with antimycin A, an electron transport chain blocker known to increase mitochondrial superoxide production. After 15 min, the cells were treated with either PEG-HCCs, pl/SWNTs, PEGylated SOD, PBN or PBS. The cells were then stained with DHE and the intensity of the resulting fluorescence was measured to monitor the production of the ROS superoxide. All samples were normalized relative to the fluorescence measured for the control cells without DHE or antimycin A treatment. Controls were performed that demonstrated that the nanomaterials neither had appreciable fluorescence on their own nor interfered with the DHE fluorescence at the concentrations employed. See FIG. 27. Both the PEG-HCCs and pl/SWNTs reduced, in a dose-dependent manner, the ROS levels in b.End3 cells that were stressed with antimycin A. See FIGS. 28-29. In fact, both the PEG-HCCs and pl/SWNTs reduced ROS levels in these stressed cells to the level observed in b.End3 cells not treated with antimycin A. For comparison, two known antioxidants, PEGylated SOD and PBN, were used in concentrations similar to the nanomaterials and were administered using the same protocol that was used for the nanomaterials. Under these conditions, PEGylated SOD and PBN showed minimal efficacy, possibly because they were not internalized by the cells due to the short duration of exposure. When larger doses of PEGylated SOD and PBN were used and the treatment was given both 14 h prior and 15 min after exposure to antimycin A, then a decrease in ROS was achieved that was equivalent to that observed for treatment with the nanomaterials after administration of antimycin A.

Figure 30:
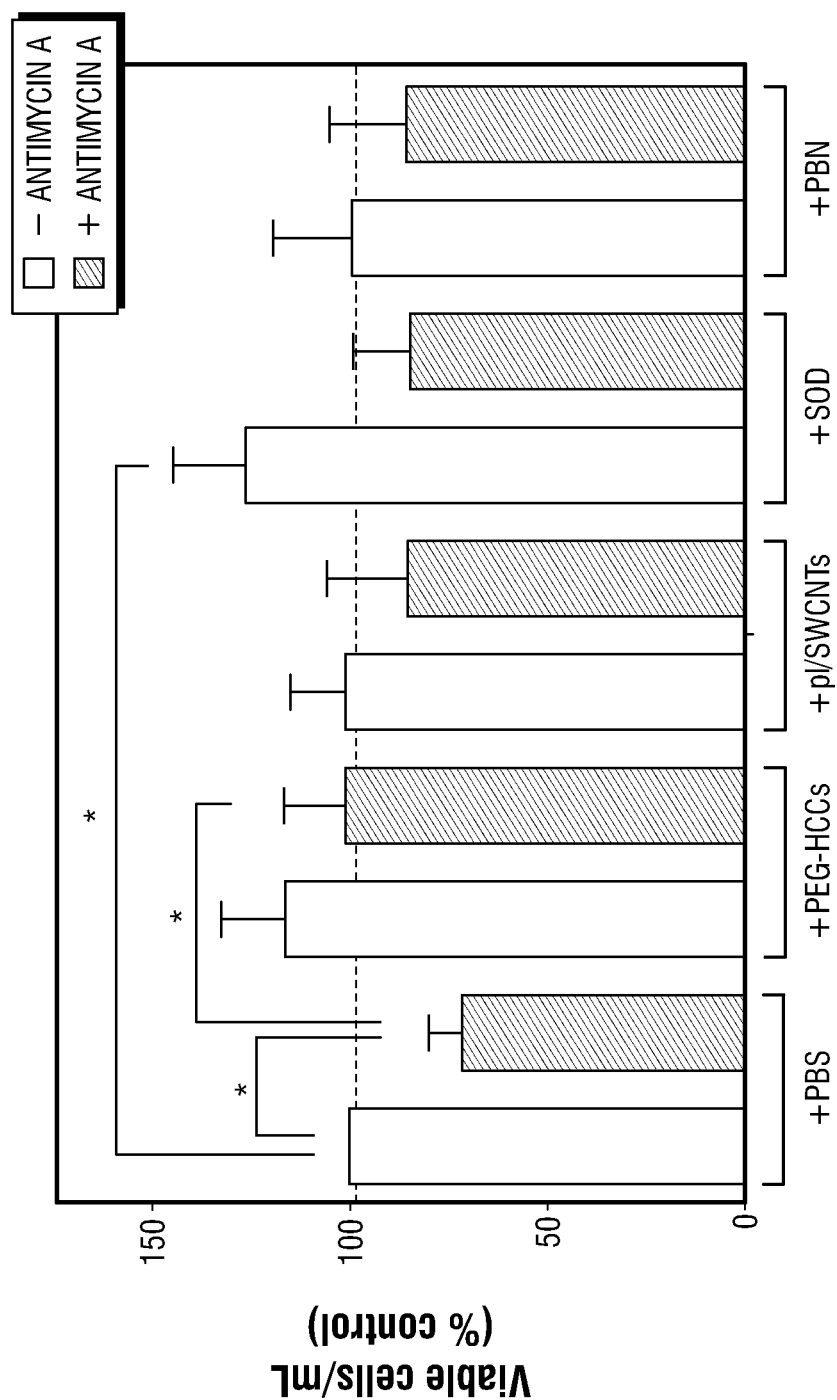
FIG. 30 shows cell survival relative to control for b.End3 cells given different treatments. The cells were either cultured in the presence of PEG-HCCs, pl/SWNTs, PEGylated SOD or PBN alone (white bars). Alternatively, the cells were first treated with a dose of antimycin A titrated to kill 30% of the cells followed by treatment with PEG-HCCs, pl/SWNTs, PEGylated SOD or PBN (grey bars). The PEG-HCCs were most effective at protecting the cells. Additional statistical findings are provided in FIG. 31. *p-value<0.05.
Figure 32:
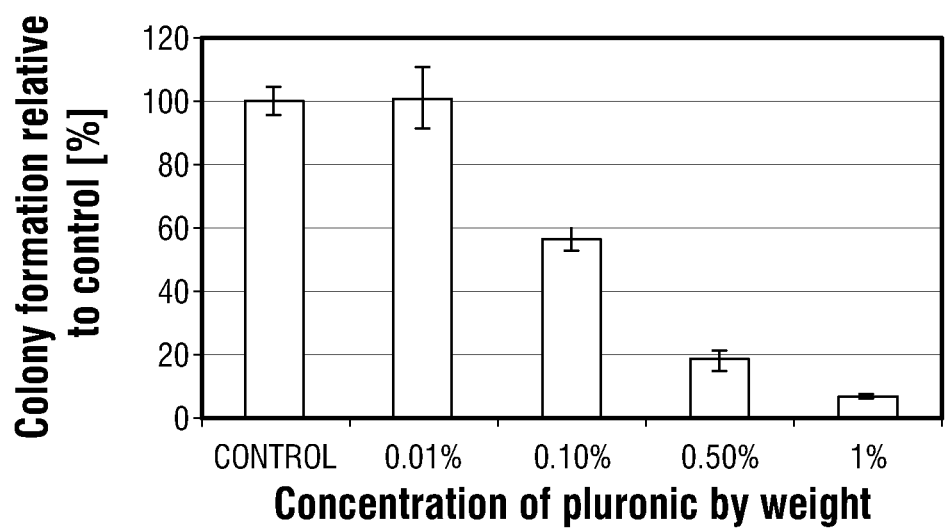
FIG. 32 provides control data indicating survival of b.end3 cells treated with various concentrations of pluronic, as measured by a clonogenic survival assay.

Since these studies indicated that both PEG-HCCs and pl/SWNTs could reduce DHE fluorescence to baseline levels in this model of oxidative stress, the two antioxidant nanomaterials were also evaluated under more severe oxidative stress models. In this experiment, the b.End3 cells were treated with a larger dose of antimycin A empirically determined to create approximately 30% reduction in cell survival. See FIGS. 30-32.

The test antioxidants were incubated with the cells for 24 h following treatment with antimycin A and cell survival was determined. Under the control conditions, in which the cells were not treated with antimycin A, PEGylated SOD increased cell survival/proliferation by 27%. A similar trend was seen with the PEG-HCCs, while PBN and pl/SWNTs did not have significant effects. However, when the cells were stressed with antimycin A and then treated with the test antioxidants, the PEG-HCCs were the more effective agents for protecting the cells. The PEG-HCC treatment resulted in cell survival equal to that of the control treatment, while treatment with pl/SWNTs, PEGylated SOD or PBN resulted in cell survival at 85% of this value.

Since PEG-SODs and PEG-HCCs had higher baseline survival/proliferation, Applicants calculated the percent recovery of each antioxidant from the antimycin A-treated cells to each antioxidants' initial baseline. By this calculation, the levels of protection were 66% for PEG-HCCs, 46% for pl/SWNT, 48% for PBN and 23% for SOD. See FIGS. 30-31.

Discussion

In this Example, Applicants demonstrated that both PEG-HCCs and pl/SWNTs are able to eliminate ROS. The ROS were generated by the metabolism of hypoxanthine by xanthine oxidase. The antioxidant ability of the nanomaterials was determined by monitoring the SOD-inhibitable reduction of ferricytochrome c.

The cytotoxicity of the nanomaterials towards b.End3 cells was also studied. PEG-HCCs showed no toxicity, even when used at a concentration 50× higher than that which showed the maximal reduction in intracellular ROS. On the other hand, the results indicated that, over a longer period of time, the pl/SWNTs were potentially toxic at 10 mg/L. Applicants further investigated this difference in toxicity by performing a clonogenic survival assay. The PEG-HCCs were once again non-toxic at all of the concentrations tested. On the other hand, Applicants found that 1% pluronic alone was highly toxic under these conditions, resulting in just 7% colony formation relative to control. Due to the magnitude of the toxicity associated with 1% pluronic, it cannot be determined in these cellular assays if the SWNTs contributed to the toxicity seen for the pl/SWNTs. The possibility still exists for applying pl/SWNTs in vivo as antioxidants, as they have been previously monitored in vivo and they showed no toxicity, as the pluronic is rapidly diluted and even displaced from the SWNTs.

Since both nanomaterials could be used safely over a short period of time, their ability to eliminate intracellular ROS was tested using a rapid assay in which b.End3 cells were stressed for 15 min with antimycin A to generate superoxide, treated for 5 min with the nanomaterials and then DHE to measure the levels of ROS. Since superoxide does not readily cross cell membranes, this assay tested the ability of these antioxidants to protect from primarily an intracellular insult. This method was selected after evaluating a variety of assays for potential interference from the carbon nanomaterials. Both the PEG-HCCs and the pl/SWNTs were able to quench the antimycin A-induced ROS in a dose-dependent manner. Again, the pl/SWNTs were more potent, as a dose of just 0.48 mg/L of the pl/SWNTs lowered the amount of ROS to the background level, while a dose of 2-4 mg/L was required for the PEG-HCCs to achieve the same effect. Interestingly, when PEGylated SOD or PBN was administered at a similar weight equivalent to the PEG-HCCs, no effect was observed. This could be the result of more rapid internalization of the nanomaterials compared to the PEGylated SOD and PBN. The rapidity of the nanomaterials' efficacy is promising for in vivo applications.

Since both PEG-HCCs and pl/SWNTs could fully eliminate the ROS from a mild oxidative stress, their effect on a cell-killing stressor was evaluated. Cells were exposed to a higher concentration of antimycin A empirically determined to kill approximately 30% of the cells and then cells were treated with pl/SWNTs, PEG-HCCs, PEGylated SOD or PBN. A set of controls was also run in which the cells were only treated with PEG-HCCs, pl/SWNTs, PEGylated SOD or PBN. Under the control conditions, in which the cells were not treated with antimycin A, both the PEG-HCCs and the SOD increased cell survival while PBN and pl/SWNTs did not have any effect. This is possibly due to the PEG-HCCs and the SOD increasing the level of antioxidants in the culture media. However, when the cells were stressed with antimycin A and then treated with the test antioxidants, the PEG-HCCs were the most effective at protecting the cells, in both an absolute and relative sense.

EXAMPLE 5

Use of PEG-HCCs to Treat Oxidative Stress Associated with Alzheimer's Disease

Alzheimer's disease (AD) is a progressive neurodegenerative disease characterized by the neuropathological accumulation of amyloid beta (AR) deposition as well as neurofibrillary tangles. Current therapies for AD primarily target the symptoms, while treatments to halt or reverse the course of the disease remain experimental. Although the potential neurotoxic effect of AR has been long established, its specific role in the cascade of events leading to memory impairments is unknown. Several reports propose a link between AR and oxidative stress to explain the downstream cognitive deficits observed in AD. Specifically, it has been shown that AR promotes oxidation in several model systems and conversely, pro-oxidants increase the production of Aβ3.

One of the major characteristics of AD is the deposition of amyloid plaques. Transgenic animals such as the Tg2576 model that over-express a mutated form of APP (Swedish mutation), exhibit increased AR levels at an early age (i.e., 6 months) followed by the development of neuritic plaques and cognitive defects by 8-9 months of age. AB peptides exhibit oxidant properties and can compromise mitochondrial function. For example, soluble AB species have been linked to an increase in hydrogen peroxide and a decrease in cytochrome C oxidase activity in the Tg2576 mouse model. Additionally, AR has been shown to enter the mitochondria and cause an amplification cascade that leads to inactivation of SOD-2 and generation of additional free radicals. Also consistent with a pathogenic interaction between A8 and mitochondria, SOD-2 knockout mice exhibit an increased plaque burden. Furthermore, SOD-2 immunohistochemistry from post-mortem human AD brain samples demonstrates a global increase in SOD-2 as a compensatory mechanism to oxidative stress associated with AD.

Applicants' prior work has established that the mitochondrial enzyme, superoxide dismutase 2 (SOD-2), is involved in the pathogenesis of AD in a mouse model. In particular, Applicants previously tested if over-expression of SOD-2 could prevent AD-related pathology and memory impairments in a mouse model of AD (Tg2576) through subsequent reduction in reactive oxygen species (ROS). *PNAS*, 2009. 106(32):13576-81. Based on such findings, Applicants envision that the impact of ROS may be a key event in the initiation of AD-related pathology and memory deficits.

However, antioxidant trials have produced conflicting results, perhaps due to lack of potency, as seen in acute injury studies and the dependence on intrinsic radical scavenging due to subsequent radical transfer. For example, superoxide dismutase, while reducing superoxide radical levels, generates hydrogen peroxide which then depends on additional enzymatic activity to reduce overall oxygen radical activity. Potential reasons for these conflicting results include the lack of potency of available antioxidants, as has been seen in acute conditions such as head trauma as well as the dependence of most of these antioxidants on subsequent radical scavenging.

Based on the above-mentioned observations, Applicants envision the use of the carbon nanomaterials of the present disclosure to effectively reduce ROS formation in AD. Applicants propose that the use of the carbon nanomaterials of the present disclosure could provide a novel approach to treat Alzheimer's Disease. Applicants' data presented herein provide support for this approach.

EXAMPLE 5A

PEG-HCCs Reduce ROS Formation in $T_2 2576$ Mice

Figure 33:
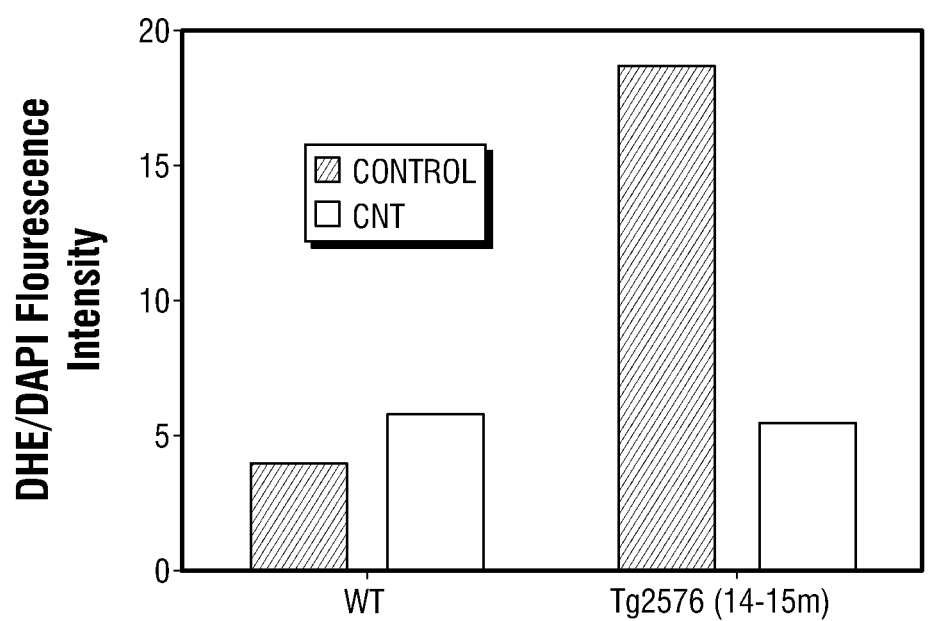
FIG. 33 shows data indicating that treatment with PEG-HCCs reduced ROS formation in the brains of 14-15Tg2576 mice. Mice were injected i.p. with vehicle (Control) or PEG-HCCs. The dose of PEG-HCCs was 200 RI of 150 mg/l solution. Mice were injected at 24 and 48 hours prior to euthanasia (DHE was administered at the 24 hour time point). Mice were euthanized and the DHE/DAPI ratio in the hippocampus was assessed. A significant increase in DHE staining in the TG2576 mice was observed, indicating increased ROS formation. However, in Tg2576 mice treated with PEG-HCCs, a normalization of the DHE staining was observed, indicating that ROS formation was reduced back to wild-type levels.

FIG. 33 shows preliminary data indicating that PEG-HCCs can reduce ROS formation in Tg2576 mice upon intraperitoneal (IP) administration. In this Example, mice were injected intraperitoneally with vehicle samples (Control) or PEG-HCCs. The dose of PEG-HCCs was 200 RI of 150 mg/I solution. Mice were injected at 24 and 48 hours prior to euthanasia (DHE was administered at the 24 hour time point). Mice were euthanized and the DHE/DAPI ratio in the hippocampus was assessed. Applicants observed a significant increase in DHE staining in the Tg2576 mice, reflective of increased ROS formation. However, in the Tg2576 mice treated with PEG-HCCs, Applicants observed a normalization of the DHE staining, indicating that ROS formation was reduced back to wildtype levels. Overall, these results demonstrate that treatment with the PEG-HCCs can reduce ROS formation in the 14-15 sections Tg2576 mouse brains.

Based on the above findings, Applicants envision that the carbon nanomaterials of the present disclosure can significantly reduce ROS formation in the Tg2576 mouse model of AD, thereby leading to significant improvements (behavioral, biochemical and physiological) similar to what Applicants observed in the Tg2576/SOD-2 mice. Additionally, based on the above results, Applicants expect behavioral, axonal transport and cerebral blood flow improvements, as well as reduced plaque formation with the functionalized PEG-HCCs and HCCs.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of treating oxidative stress in a subject, wherein the method comprises:
   administering a therapeutic composition to reduce the levels of reactive oxygen species in the subject, wherein the therapeutic composition includes a polyethylene glycol functionalized hydrophilic carbon cluster (PEG-HCC), conjugated with: (i) a plurality of aromatic domains and (ii) an adamantane derivative covalently bound to the terminus of the polyethylene glycol functionality of the PEG-HCCs.

2. The method of claim 1, wherein the anti-oxidant activity of the carbon nanomaterial corresponds to ORAC values between about 200 to about 15,000.

3. The method of claim 1, wherein the levels of reactive oxygen species in the subject are reduced by about 5% to about 75%.

4. The method of claim 1, wherein the therapeutic composition reduces the levels of one or more of the reactive oxygen species: nitric oxides, superoxides, hydroperoxyls, hydrogen peroxide, oxygen radicals, hydroxyl radicals, organic hydroperoxides, alkoxy radicals, peroxy radicals, hypochlorous acids, peroxynitrites, and combinations thereof.

5. The method of claim 1, wherein the subject is a human being.

6. The method of claim 1, wherein the administering of the therapeutic composition comprises intravenous administration.

7. The method of claim 1, wherein the administering of the therapeutic composition is for treating a disease or ischemic condition selected from the group consisting of traumatic brain injury, ischemia, anoxic encephalopathy, hypoxic or ischemic encephalopathy, cerebrovascular dysfunction, hemorrhagic shock, hypoxia, hypotension, Alzheimer's disease, Parkinson's disease, multiple sclerosis, amyotrophic lateral sclerosis, liver disease, non-alcoholic fatty liver disease, diabetes, stroke, inflammation, spinal cord injury, central nervous system injury or neuropathy, organ transplantation, and combinations thereof.

8. The method of claim 7, wherein the disease or ischemic condition is associated with traumatic brain injury.

9. The method of claim 1, wherein the oxidative stress is associated with cerebrovascular dysfunction following traumatic brain injury.

10. The method of claim 1, wherein administering of the therapeutic composition is for treating non-alcoholic fatty liver disease.

11. The method of claim 1, wherein the hydrophilic carbon cluster is selected from the group consisting of single-walled nanotubes, double-walled nanotubes, triple-walled nanotubes, multi-walled nanotubes, ultra-short nanotubes, graphene, graphene nanoribbons, graphite, graphite oxide nanoribbons, carbon black, oxidized carbon black, and combinations thereof.

12. The method of claim 1, wherein the hydrophilic carbon cluster is functionalized with a plurality of solubilizing groups.

13. The method of claim 12, wherein the solubilizing groups are selected from the group consisting of poly(ethylene glycol), poly(propylene glycol), poly(vinyl alcohol), poly(phenylene oxide), poly(ethylene imines), poly(acrylic acid), poly(vinyl amine) and combinations thereof.

14. The method of claim 1, wherein the therapeutic composition further comprises an active agent associated with the carbon nanomaterial.

15. The method of claim 14, wherein the active agent is selected from the group consisting of anti-oxidants, anti-inflammatory drugs, anti-cancer drugs, anti-diabetic drugs, siRNA, and combinations thereof.

16. The method of claim 14, wherein the active agent is non-covalently associated with the hydrophilic carbon cluster.

17. The method of claim 1, wherein the therapeutic composition further comprises a targeting agent, wherein the targeting agent has recognition activity for a marker related to oxidative stress.

18. The method of claim 17, wherein the marker is a cell surface protein that is up-regulated in response to oxidative stress.

19. The method of claim 18, wherein the cell surface protein is selected from the group consisting of p-selectin molecules, transferrin receptors, angiotensin receptors, cannabinoid receptors, epidermal growth factor receptors, adhesion molecules, channel proteins, and combinations thereof.

20. The method of claim 17, wherein the targeting agent is selected from the group consisting of antibodies, proteins, RNA, DNA, aptamers, small molecules, dendrimers, and combinations thereof.

21. The method of claim 17, wherein the targeting agent is non-covalently associated with the carbon nanomaterial.

22. The method of claim 17, wherein the targeting agent is covalently associated with the carbon nanomaterial.

23. The method of claim 1, wherein a transporter moiety selected from the group consisting of cannabinoid molecules, cannabinoid molecule derivatives, HU-210 and combinations thereof is covalently linked to the PEG-HCCs.

24. The method of claim 23, wherein the transporter moiety is an unnatural enantiomer of a cannabinoid molecule.

25. The method of claim 24, wherein the transporter moiety is HU-211.

26. A method of treating oxidative stress in a subject, wherein the method comprises: administering a therapeutic composition to reduce the levels of reactive oxygen species in the subject, wherein the therapeutic composition includes a polyethylene glycol functionalized hydrophilic carbon cluster (PEG-HCC), and wherein an adamantane derivative is covalently bound to the terminus of the polyethylene glycol functionality of the PEG-HCCs.

27. The method of claim 1 wherein the adamantane derivative is amantadine, memantine, rimantadine, dopamantin, tromantadine, vildagliptin, or karmantadin.

28. The method of claim 26 wherein the adamantane derivative is amantadine, memantine, rimantadine, dopamantin, tromantadine, vildagliptin, or karmantadin.

* * * * *